(12) United States Patent
Maurer et al.

(10) Patent No.: US 10,626,160 B2
(45) Date of Patent: *Apr. 21, 2020

(54) TRANSFECTED T-CELLS AND T-CELL RECEPTORS FOR USE IN IMMUNOTHERAPY AGAINST CANCERS

(71) Applicant: IMMATICS BIOTECHNOLOGIES GMBH, Tuebingen (DE)

(72) Inventors: Dominik Maurer, Moessingen (DE); Sebastian Bunk, Tuebingen (DE); Leonie Alten, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/403,058

(22) Filed: May 3, 2019

(65) Prior Publication Data

US 2019/0309042 A1 Oct. 10, 2019

Related U.S. Application Data

(63) Continuation of application No. 15/460,654, filed on Mar. 16, 2017.

(60) Provisional application No. 62/308,975, filed on Mar. 16, 2016.

(30) Foreign Application Priority Data

Mar. 16, 2016 (GB) .................................. 1604492.7

(51) Int. Cl.
| | | |
|---|---|---|
| *C07K 14/725* | (2006.01) | |
| *A61K 35/12* | (2015.01) | |
| *A61K 35/17* | (2015.01) | |
| *A61K 35/66* | (2015.01) | |
| *C07K 14/435* | (2006.01) | |
| *C12N 15/09* | (2006.01) | |
| *C12N 15/10* | (2006.01) | |
| *A61K 38/00* | (2006.01) | |

(52) U.S. Cl.
CPC .......... *C07K 14/7051* (2013.01); *A61K 35/12* (2013.01); *A61K 35/17* (2013.01); *A61K 35/66* (2013.01); *C07K 14/435* (2013.01); *C12N 15/09* (2013.01); *C12N 15/10* (2013.01); *A61K 38/00* (2013.01)

(58) Field of Classification Search
None
See application file for complete search history.

(56) References Cited

U.S. PATENT DOCUMENTS

2010/0034841 A1 2/2010 Nishimura
2013/0273647 A1 10/2013 Sahin et al.

FOREIGN PATENT DOCUMENTS

| EP | 1930433 A1 | 6/2008 |
|---|---|---|
| EP | 2752198 A1 | 7/2014 |
| WO | 2013/057596 A1 | 4/2013 |
| WO | 2015075939 A1 | 3/2017 |

OTHER PUBLICATIONS

Janeway et al., Immunobiology, 5th Ed., Garland Science, pp. 106-108 and 260-263, (2001) (Year: 2001).*
Manning et al., Immunity, vol. 8, 413-425, Apr. 1998. (Year: 1998).*
Piepenbrink et al., Nature, 2013; 4:1948. (Year: 2013).*
Garcia et al., Cell, vol. 122, 333-336, Aug. 12, 2005. (Year: 2005).*
Portolano et al., J Immunol. Feb. 1, 1993;150(3):880-7. (Year: 1993).*
Goyarts et al. (Mol Immunol. Jul. 1998;35(10):593-607). (Year: 1998).*
Bossi et al., 2003, OncoImmunology, 2:11, e26840. (Year: 2003).*
Popovic et al. (Blood. 2011; 118(4):946-954). (Year: 2011).*
Nakatsugawa et al., International Journal of Oncology 39: 1041-1049, 2011. (Year: 2011).*
Search Report of British Patent Application No. 1604492.7 dated Jan. 3, 2017.
Shirakura, Yoshitaka et al., "T-cell receptor gene therapy targeting melanoma-associated antigen-A4 inhibits human tumor growth in non-obese diabetic/SCID/γcellnull mice", Cancer Science, Jan. 2012, pp. 17-25, vol. 103, No. 1.
Kageyama, Shinichi et al., "Adoptive Transfer of MAGE-A4 T-cell Receptor Gene-Transduced Lymphocytes in Patients with Recurrent Esophageal Cancer", Clinical Cancer Research, May 15, 2015, pp. 2268-2277, vol. 21, No. 10.
Wu, Z.Y. et al., "Identification of a Novel CD8+ T Cell Epitope Derived from Cancer-Testis Antigen MAGE-4 in Oesophageal Carcinoma", Scandinavian Journal of Immunology, 2011, pp. 561-567, vol. 74.

(Continued)

*Primary Examiner* — Zachary S Skelding
(74) *Attorney, Agent, or Firm* — McBee Moore & Vanik IP, LLC

(57) ABSTRACT

Disclosed are T-cell receptors (TCRs) binding to tumor-associated antigens (TAAs) for targeting cancer cells, T-cells expressing same, methods for producing same, and methods for treating cancers using same. Disclosed are TCRs and their variants that bind to HLA class I or II molecules with a peptide, such as MAG-003 have the amino acid sequence of KVLEHVVRV (SEQ ID NO:1). The description further relates to peptides, proteins, nucleic acids, cells for use in immunotherapeutic methods, the immunotherapy of cancer, and tumor-associated T-cell peptide epitopes, alone or in combination with other tumor-associated peptides that can for example serve as active pharmaceutical ingredients of vaccine compositions that stimulate anti-tumor immune responses, or to stimulate T-cells ex vivo and transfer into patients. Peptides bound to molecules of the major histocompatibility complex (MHC), or peptides as such, can also be targets of antibodies, soluble T-cell receptors, and other binding molecules.

20 Claims, 16 Drawing Sheets
(16 of 16 Drawing Sheet(s) Filed in Color)
Specification includes a Sequence Listing.

(56) References Cited

OTHER PUBLICATIONS

Jia, Zheng-Cai et al., "Identification of Two Novel HLA-A*0201-Restricted CTL Epitopes Derived from MAGE-A4", Clinical & Developmental Immunology, 2010, Article ID: 567594.
PCT International Search Report for PCT/EP2017/056260, dated May 30, 2017.
Ohkuri, et al., "Identification of novel helper epitopes of MAGE-A4 tumour antigen: useful tool for the propagation of Th1 cells," (2009), vol. 100, No. 7: 1135-1143.
Database UniProt [Online], Nov. 1, 1995 (Nov. 1, 1995). UNIPROT: P43358. Database Accession No. P43358 sequence. XP055374176.

* cited by examiner

SEQUENCE LISTING

```
<160> NUMBER OF SEQ ID NOS: 101

<210> SEQ ID NO 1
<211> LENGTH: 9
<212> TYPE: PRT
<213> ORGANISM: Homo sapiens

<400> SEQUENCE: 1

Lys Val Leu Glu His Val Val Arg Val
1               5

<210> SEQ ID NO 2
<211> LENGTH: 9
<212> TYPE: PRT
<213> ORGANISM: Homo sapiens

<400> SEQUENCE: 2

Lys Val Leu Glu His Val Val Arg Leu
1               5

<210> SEQ ID NO 3
<211> LENGTH: 9
<212> TYPE: PRT
<213> ORGANISM: Homo sapiens

<400> SEQUENCE: 3

Lys Val Leu Glu His Val Val Arg Ala
1               5

<210> SEQ ID NO 4
<211> LENGTH: 9
```

<212> TYPE: PRT
<213> ORGANISM: Homo sapiens

<400> SEQUENCE: 4

Lys Val Leu Glu His Val Val Arg Ile
1               5

<210> SEQ ID NO 5
<211> LENGTH: 9
<212> TYPE: PRT
<213> ORGANISM: Homo sapiens

<400> SEQUENCE: 5

Lys Leu Leu Glu His Val Val Arg Val
1               5

<210> SEQ ID NO 6
<211> LENGTH: 9
<212> TYPE: PRT
<213> ORGANISM: Homo sapiens

<400> SEQUENCE: 6

Lys Leu Leu Glu His Val Val Arg Leu
1               5

<210> SEQ ID NO 7
<211> LENGTH: 9
<212> TYPE: PRT
<213> ORGANISM: Homo sapiens

<400> SEQUENCE: 7

Lys Leu Leu Glu His Val Val Arg Ala
1               5

<210> SEQ ID NO 8
<211> LENGTH: 9
<212> TYPE: PRT
<213> ORGANISM: Homo sapiens

<400> SEQUENCE: 8

Lys Leu Leu Glu His Val Val Arg Ile
1               5

<210> SEQ ID NO 9
<211> LENGTH: 9
<212> TYPE: PRT
<213> ORGANISM: Homo sapiens

<400> SEQUENCE: 9

Lys Ala Leu Glu His Val Val Arg Val
1               5

<210> SEQ ID NO 10
<211> LENGTH: 9
<212> TYPE: PRT
<213> ORGANISM: Homo sapiens

<400> SEQUENCE: 10

Lys Ala Leu Glu His Val Val Arg Leu
1               5

<210> SEQ ID NO 11
<211> LENGTH: 9
<212> TYPE: PRT
<213> ORGANISM: Homo sapiens

```
<400> SEQUENCE: 11

Lys Ala Leu Glu His Val Val Arg Ala
1               5

<210> SEQ ID NO 12
<211> LENGTH: 9
<212> TYPE: PRT
<213> ORGANISM: Homo sapiens

<400> SEQUENCE: 12

Lys Ala Leu Glu His Val Val Arg Ile
1               5

<210> SEQ ID NO 13
<211> LENGTH: 9
<212> TYPE: PRT
<213> ORGANISM: Homo sapiens

<400> SEQUENCE: 13

Tyr Leu Leu Glu His Val Val Arg Val
1               5

<210> SEQ ID NO 14
<211> LENGTH: 9
<212> TYPE: PRT
<213> ORGANISM: Homo sapiens

<400> SEQUENCE: 14

Tyr Leu Leu Glu His Val Val Arg Leu
1               5

<210> SEQ ID NO 15
<211> LENGTH: 9
<212> TYPE: PRT
<213> ORGANISM: Homo sapiens

<400> SEQUENCE: 15

Tyr Leu Leu Glu His Val Val Arg Ala
1               5

<210> SEQ ID NO 16
<211> LENGTH: 9
<212> TYPE: PRT
<213> ORGANISM: Homo sapiens

<400> SEQUENCE: 16

Tyr Leu Leu Glu His Val Val Arg Ile
1               5

<210> SEQ ID NO 17
<211> LENGTH: 9
<212> TYPE: PRT
<213> ORGANISM: Homo sapiens

<400> SEQUENCE: 17

Tyr Ala Leu Glu His Val Val Arg Val
1               5

<210> SEQ ID NO 18
<211> LENGTH: 9
<212> TYPE: PRT
<213> ORGANISM: Homo sapiens

<400> SEQUENCE: 18
```

Tyr Ala Leu Glu His Val Val Arg Leu
1               5

<210> SEQ ID NO 19
<211> LENGTH: 9
<212> TYPE: PRT
<213> ORGANISM: Homo sapiens

<400> SEQUENCE: 19

Tyr Ala Leu Glu His Val Val Arg Ala
1               5

<210> SEQ ID NO 20
<211> LENGTH: 9
<212> TYPE: PRT
<213> ORGANISM: Homo sapiens

<400> SEQUENCE: 20

Tyr Ala Leu Glu His Val Val Arg Ile
1               5

<210> SEQ ID NO 21
<211> LENGTH: 9
<212> TYPE: PRT
<213> ORGANISM: Homo sapiens

<400> SEQUENCE: 21

Tyr Val Leu Glu His Val Val Arg Val
1               5

<210> SEQ ID NO 22
<211> LENGTH: 9
<212> TYPE: PRT
<213> ORGANISM: Homo sapiens

<400> SEQUENCE: 22

Tyr Val Leu Glu His Val Val Arg Leu
1               5

<210> SEQ ID NO 23
<211> LENGTH: 9
<212> TYPE: PRT
<213> ORGANISM: Homo sapiens

<400> SEQUENCE: 23

Tyr Val Leu Glu His Val Val Arg Ala
1               5

<210> SEQ ID NO 24
<211> LENGTH: 9
<212> TYPE: PRT
<213> ORGANISM: Homo sapiens

<400> SEQUENCE: 24

Tyr Val Leu Glu His Val Val Arg Ile
1               5

<210> SEQ ID NO 25
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be Lys or Tyr

```
<220> FEATURE:
<221> NAME/KEY: misc_feature
<222> LOCATION: (2)..(2)
<223> OTHER INFORMATION: Xaa can be Val, Leu or Ala
<220> FEATURE:
<221> NAME/KEY: misc_feature
<222> LOCATION: (9)..(9)
<223> OTHER INFORMATION: Xaa can be Val, Leu, Ala or Ile

<400> SEQUENCE: 25

Xaa Xaa Leu Glu His Val Val Arg Xaa
1               5

<210> SEQ ID NO 26
<211> LENGTH: 36
<212> TYPE: DNA
<213> ORGANISM: Homo sapiens

<400> SEQUENCE: 26
ggaattccat atgagtcaac aaggagaaga agatcc                      36

<210> SEQ ID NO 27
<211> LENGTH: 36
<212> TYPE: DNA
<213> ORGANISM: Homo sapiens

<400> SEQUENCE: 27
ttgtcagtcg acttagagtc tctcagctgg tacacg                      36

<210> SEQ ID NO 28
<211> LENGTH: 36
<212> TYPE: DNA
<213> ORGANISM: Homo sapiens

<400> SEQUENCE: 28
tctctcatat ggatggtgga attactcaat ccccaa                      36

<210> SEQ ID NO 29
<211> LENGTH: 32
<212> TYPE: DNA
<213> ORGANISM: Homo sapiens

<400> SEQUENCE: 29
tagaaaccgg tggccaggca caccagtgtg gc                          32

<210> SEQ ID NO 30
<211> LENGTH: 9
<212> TYPE: PRT
<213> ORGANISM: Homo sapiens

<400> SEQUENCE: 30

Ala Val Leu Glu His Val Val Arg Val
1               5

<210> SEQ ID NO 31
<211> LENGTH: 9
<212> TYPE: PRT
<213> ORGANISM: Homo sapiens

<400> SEQUENCE: 31

Lys Ala Leu Glu His Val Val Arg Val
1               5

<210> SEQ ID NO 32
<211> LENGTH: 9
```

```
<212> TYPE: PRT
<213> ORGANISM: Homo sapiens

<400> SEQUENCE: 32

Lys Val Ala Glu His Val Val Arg Val
1               5

<210> SEQ ID NO 33
<211> LENGTH: 9
<212> TYPE: PRT
<213> ORGANISM: Homo sapiens

<400> SEQUENCE: 33

Lys Val Leu Ala His Val Val Arg Val
1               5

<210> SEQ ID NO 34
<211> LENGTH: 9
<212> TYPE: PRT
<213> ORGANISM: Homo sapiens

<400> SEQUENCE: 34

Lys Val Leu Glu Ala Val Val Arg Val
1               5

<210> SEQ ID NO 35
<211> LENGTH: 9
<212> TYPE: PRT
<213> ORGANISM: Homo sapiens

<400> SEQUENCE: 35

Lys Val Leu Glu His Ala Val Arg Val
1               5

<210> SEQ ID NO 36
<211> LENGTH: 9
<212> TYPE: PRT
<213> ORGANISM: Homo sapiens

<400> SEQUENCE: 36

Lys Val Leu Glu His Val Ala Arg Val
1               5

<210> SEQ ID NO 37
<211> LENGTH: 9
<212> TYPE: PRT
<213> ORGANISM: Homo sapiens

<400> SEQUENCE: 37

Lys Val Leu Glu His Val Val Ala Val
1               5

<210> SEQ ID NO 38
<211> LENGTH: 9
<212> TYPE: PRT
<213> ORGANISM: Homo sapiens

<400> SEQUENCE: 38

Lys Val Leu Glu His Val Val Arg Ala
1               5

<210> SEQ ID NO 39
<211> LENGTH: 274
<212> TYPE: PRT
<213> ORGANISM: Homo sapiens
```

<400> SEQUENCE: 39

```
Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln Asp Pro Gly Lys Gly
50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
            85                  90                  95

Thr Ala Pro Lys Pro Glu Asp Ser Ala Thr Tyr Leu Cys Ala Val Gln
            100                 105                 110

Gly Glu Asn Ser Gly Tyr Ser Thr Leu Thr Phe Gly Lys Gly Thr Met
            115                 120                 125

Leu Leu Val Ser Pro Asp Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 40
<211> LENGTH: 21
<212> TYPE: PRT
<213> ORGANISM: Homo sapiens

<400> SEQUENCE: 40

```
Met Glu Lys Met Leu Glu Cys Ala Phe Ile Val Leu Trp Leu Gln Leu
1               5                   10                  15

Gly Trp Leu Ser Gly
            20
```

<210> SEQ ID NO 41
<211> LENGTH: 112
<212> TYPE: PRT
<213> ORGANISM: Homo sapiens

<400> SEQUENCE: 41

Met Glu Lys Met Leu Glu Cys Ala Phe Ile Val Leu Trp Leu Gln Leu

```
                1               5                  10                 15
            Gly Trp Leu Ser Gly Glu Asp Gln Val Thr Gln Ser Pro Glu Ala Leu
                               20                 25                 30
            Arg Leu Gln Glu Gly Glu Ser Ser Leu Asn Cys Ser Tyr Thr Val
                               35                 40                 45
            Ser Gly Leu Arg Gly Leu Phe Trp Tyr Arg Gln Asp Pro Gly Lys Gly
                50                        55                 60
            Pro Glu Phe Leu Phe Thr Leu Tyr Ser Ala Gly Glu Glu Lys Glu Lys
            65                        70                 75                 80
            Glu Arg Leu Lys Ala Thr Leu Thr Lys Lys Glu Ser Phe Leu His Ile
                               85                 90                 95
            Thr Ala Pro Lys Pro Glu Asp Ser Ala Thr Tyr Leu Cys Ala Val Gln
                               100                105                110
```

<210> SEQ ID NO 42
<211> LENGTH: 6
<212> TYPE: PRT
<213> ORGANISM: Homo sapiens

<400> SEQUENCE: 42

```
Val Ser Gly Leu Arg Gly
1               5
```

<210> SEQ ID NO 43
<211> LENGTH: 3
<212> TYPE: PRT
<213> ORGANISM: Homo sapiens

<400> SEQUENCE: 43

```
Leu Tyr Ser
1
```

<210> SEQ ID NO 44
<211> LENGTH: 15
<212> TYPE: PRT
<213> ORGANISM: Homo sapiens

<400> SEQUENCE: 44

```
Cys Ala Val Gln Gly Glu Asn Ser Gly Tyr Ser Thr Leu Thr Phe
1               5                   10                  15
```

<210> SEQ ID NO 45
<211> LENGTH: 19
<212> TYPE: PRT
<213> ORGANISM: Homo sapiens

<400> SEQUENCE: 45

```
Asn Ser Gly Tyr Ser Thr Leu Thr Phe Gly Lys Gly Thr Met Leu Leu
1               5                   10                  15

Val Ser Pro
```

<210> SEQ ID NO 46
<211> LENGTH: 141
<212> TYPE: PRT
<213> ORGANISM: Homo sapiens

<400> SEQUENCE: 46

```
Asp Ile Gln Asn Pro Asp Pro Ala Val Tyr Gln Leu Arg Asp Ser Lys
1               5                   10                  15
Ser Ser Asp Lys Ser Val Cys Leu Phe Thr Asp Phe Asp Ser Gln Thr
                20                  25                  30
```

```
Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
 50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
130                 135                 140

<210> SEQ ID NO 47
<211> LENGTH: 314
<212> TYPE: PRT
<213> ORGANISM: Homo sapiens

<400> SEQUENCE: 47

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
             20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
 50                  55                  60

Ile Tyr Tyr Ser Met Asn Val Glu Val Thr Asp Lys Gly Asp Val Pro
 65                  70                  75                  80

Glu Gly Tyr Lys Val Ser Arg Lys Glu Lys Arg Asn Phe Pro Leu Ile
                 85                  90                  95

Leu Glu Ser Pro Ser Pro Asn Gln Thr Ser Leu Tyr Phe Cys Ala Ser
                100                 105                 110

Ser Leu Gly Pro Gly Leu Ala Ala Tyr Asn Glu Gln Phe Phe Gly Pro
            115                 120                 125

Gly Thr Arg Leu Thr Val Leu Glu Asp Leu Lys Asn Val Phe Pro Pro
130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
                180                 185                 190

Thr Asp Pro Gln Pro Leu Lys Glu Gln Pro Ala Leu Asn Asp Ser Arg
            195                 200                 205

Tyr Cys Leu Ser Ser Arg Leu Arg Val Ser Ala Thr Phe Trp Gln Asn
210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
```

```
                260                 265                 270
Tyr Gln Gln Gly Val Leu Ser Ala Thr Ile Leu Tyr Glu Ile Leu Leu
            275                 280                 285
Gly Lys Ala Thr Leu Tyr Ala Val Leu Val Ser Ala Leu Val Leu Met
        290                 295                 300
Ala Met Val Lys Arg Lys Asp Ser Arg Gly
305                 310

<210> SEQ ID NO 48
<211> LENGTH: 19
<212> TYPE: PRT
<213> ORGANISM: Homo sapiens

<400> SEQUENCE: 48

Met Gly Pro Gln Leu Leu Gly Tyr Val Val Leu Cys Leu Leu Gly Ala
1               5                   10                  15

Gly Pro Leu

<210> SEQ ID NO 49
<211> LENGTH: 114
<212> TYPE: PRT
<213> ORGANISM: Homo sapiens

<400> SEQUENCE: 49

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Leu

<210> SEQ ID NO 50
<211> LENGTH: 5
<212> TYPE: PRT
<213> ORGANISM: Homo sapiens

<400> SEQUENCE: 50

Met Asn His Glu Tyr
1               5

<210> SEQ ID NO 51
<211> LENGTH: 6
<212> TYPE: PRT
<213> ORGANISM: Homo sapiens

<400> SEQUENCE: 51

Ser Met Asn Val Glu Val
1               5

<210> SEQ ID NO 52
```

<211> LENGTH: 16
<212> TYPE: PRT
<213> ORGANISM: Homo sapiens

<400> SEQUENCE: 52

Cys Ala Ser Ser Leu Gly Pro Gly Leu Ala Ala Tyr Asn Glu Gln Phe
1               5                   10                  15

<210> SEQ ID NO 53
<211> LENGTH: 15
<212> TYPE: PRT
<213> ORGANISM: Homo sapiens

<400> SEQUENCE: 53

Tyr Asn Glu Gln Phe Phe Gly Pro Gly Thr Arg Leu Thr Val Leu
1               5                   10                  15

<210> SEQ ID NO 54
<211> LENGTH: 179
<212> TYPE: PRT
<213> ORGANISM: Homo sapiens

<400> SEQUENCE: 54

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 55
<211> LENGTH: 272
<212> TYPE: PRT
<213> ORGANISM: Homo sapiens

<400> SEQUENCE: 55

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Tyr Ser Ser Ala Ser Lys Ile Ile Phe Gly Ser Gly Thr Arg Leu Ser
        115                 120                 125

Ile Arg Pro Asn Ile Gln Asn Pro Asp Pro Ala Val Tyr Gln Leu Arg
        130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 56
<211> LENGTH: 21
<212> TYPE: PRT
<213> ORGANISM: Homo sapiens

<400> SEQUENCE: 56

Met Lys Thr Phe Ala Gly Phe Ser Phe Leu Phe Leu Trp Leu Gln Leu
1               5                   10                  15

Asp Cys Met Ser Arg
            20

<210> SEQ ID NO 57
<211> LENGTH: 112
<212> TYPE: PRT
<213> ORGANISM: Homo sapiens

<400> SEQUENCE: 57

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

```
Arg Leu Thr Val Leu Leu Asn Lys Lys Asp Lys His Leu Ser Leu Arg
                85                  90                  95
Ile Ala Asp Thr Gln Thr Gly Asp Ser Ala Ile Tyr Phe Cys Ala Glu
            100                 105                 110
```

<210> SEQ ID NO 58
<211> LENGTH: 6
<212> TYPE: PRT
<213> ORGANISM: Homo sapiens

<400> SEQUENCE: 58

```
Asp Ser Ser Ser Thr Tyr
1               5
```

<210> SEQ ID NO 59
<211> LENGTH: 3
<212> TYPE: PRT
<213> ORGANISM: Homo sapiens

<400> SEQUENCE: 59

```
Ile Phe Ser
1
```

<210> SEQ ID NO 60
<211> LENGTH: 12
<212> TYPE: PRT
<213> ORGANISM: Homo sapiens

<400> SEQUENCE: 60

```
Cys Ala Glu Tyr Ser Ser Ala Ser Lys Ile Ile Phe
1               5                   10
```

<210> SEQ ID NO 61
<211> LENGTH: 19
<212> TYPE: PRT
<213> ORGANISM: Homo sapiens

<400> SEQUENCE: 61

```
Tyr Ser Ser Ala Ser Lys Ile Ile Phe Gly Ser Gly Thr Arg Leu Ser
1               5                   10                  15
Ile Arg Pro
```

<210> SEQ ID NO 62
<211> LENGTH: 141
<212> TYPE: PRT
<213> ORGANISM: Homo sapiens

<400> SEQUENCE: 62

```
Asn Ile Gln Asn Pro Asp Pro Ala Val Tyr Gln Leu Arg Asp Ser Lys
1               5                   10                  15
Ser Ser Asp Lys Ser Val Cys Leu Phe Thr Asp Phe Asp Ser Gln Thr
            20                  25                  30
Asn Val Ser Gln Ser Lys Asp Ser Asp Val Tyr Ile Thr Asp Lys Thr
        35                  40                  45
Val Leu Asp Met Arg Ser Met Asp Phe Lys Ser Asn Ser Ala Val Ala
    50                  55                  60
Trp Ser Asn Lys Ser Asp Phe Ala Cys Ala Asn Ala Phe Asn Asn Ser
65                  70                  75                  80
Ile Ile Pro Glu Asp Thr Phe Phe Pro Ser Pro Glu Ser Ser Cys Asp
                85                  90                  95
```

```
Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Lys Val Ala
            115                 120                 125

Gly Phe Asn Leu Leu Met Thr Leu Arg Leu Trp Ser Ser
            130                 135                 140

<210> SEQ ID NO 63
<211> LENGTH: 310
<212> TYPE: PRT
<213> ORGANISM: Homo sapiens

<400> SEQUENCE: 63

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Arg Ala Asn Thr Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 64
```

<211> LENGTH: 19
<212> TYPE: PRT
<213> ORGANISM: Homo sapiens

<400> SEQUENCE: 64

Met Gly Ser Trp Thr Leu Cys Cys Val Ser Leu Cys Ile Leu Val Ala
1               5                   10                  15

Lys His Thr

<210> SEQ ID NO 65
<211> LENGTH: 113
<212> TYPE: PRT
<213> ORGANISM: Homo sapiens

<400> SEQUENCE: 65

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser

<210> SEQ ID NO 66
<211> LENGTH: 5
<212> TYPE: PRT
<213> ORGANISM: Homo sapiens

<400> SEQUENCE: 66

Ser Gly His Asp Tyr
1               5

<210> SEQ ID NO 67
<211> LENGTH: 6
<212> TYPE: PRT
<213> ORGANISM: Homo sapiens

<400> SEQUENCE: 67

Phe Asn Asn Asn Val Pro
1               5

<210> SEQ ID NO 68
<211> LENGTH: 12
<212> TYPE: PRT
<213> ORGANISM: Homo sapiens

<400> SEQUENCE: 68

Cys Ala Ser Arg Ala Asn Thr Gly Glu Leu Phe Phe
1               5                   10

<210> SEQ ID NO 69
<211> LENGTH: 16
<212> TYPE: PRT

<213> ORGANISM: Homo sapiens

<400> SEQUENCE: 69

Asn Thr Gly Glu Leu Phe Phe Gly Glu Gly Ser Arg Leu Thr Val Leu
1               5                   10                  15

<210> SEQ ID NO 70
<211> LENGTH: 179
<212> TYPE: PRT
<213> ORGANISM: Homo sapiens

<400> SEQUENCE: 70

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 71
<211> LENGTH: 277
<212> TYPE: PRT
<213> ORGANISM: Homo sapiens

<400> SEQUENCE: 71

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Asp Ser Ala Val Tyr Phe Cys
            100                 105                 110

Ala Leu Ser Glu Gly Asn Ser Asn Thr Pro Leu Val Phe Gly Lys
            115                 120                 125

Gly Thr Arg Leu Ser Val Ile Ala Asn Ile Gln Asn Pro Asp Pro Ala
        130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
                180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
        210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser
            275

<210> SEQ ID NO 72
<211> LENGTH: 20
<212> TYPE: PRT
<213> ORGANISM: Homo sapiens

<400> SEQUENCE: 72

Met Leu Thr Ala Ser Leu Leu Arg Ala Val Ile Ala Ser Ile Cys Val
1               5                   10                  15

Val Ser Ser Met
            20

<210> SEQ ID NO 73
<211> LENGTH: 116
<212> TYPE: PRT
<213> ORGANISM: Homo sapiens

<400> SEQUENCE: 73

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110

Ala Leu Ser Glu
            115

<210> SEQ ID NO 74
<211> LENGTH: 7
<212> TYPE: PRT
<213> ORGANISM: Homo sapiens

<400> SEQUENCE: 74

Thr Arg Asp Thr Thr Tyr Tyr
1               5

<210> SEQ ID NO 75
<211> LENGTH: 4
<212> TYPE: PRT
<213> ORGANISM: Homo sapiens

<400> SEQUENCE: 75

Arg Asn Ser Phe
1

<210> SEQ ID NO 76
<211> LENGTH: 15
<212> TYPE: PRT
<213> ORGANISM: Homo sapiens

<400> SEQUENCE: 76

Cys Ala Leu Ser Glu Gly Asn Ser Gly Asn Thr Pro Leu Val Phe
1               5                   10                  15

<210> SEQ ID NO 77
<211> LENGTH: 19
<212> TYPE: PRT
<213> ORGANISM: Homo sapiens

<400> SEQUENCE: 77

Asn Ser Gly Asn Thr Pro Leu Val Phe Gly Lys Gly Thr Arg Leu Ser
1               5                   10                  15

Val Ile Ala

<210> SEQ ID NO 78
<211> LENGTH: 141
<212> TYPE: PRT
<213> ORGANISM: Homo sapiens

<400> SEQUENCE: 78

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser

<210> SEQ ID NO 79
<211> LENGTH: 313
<212> TYPE: PRT
<213> ORGANISM: Homo sapiens

<400> SEQUENCE: 79

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Ser Ser Gly Ser His Gln Glu Thr Gln Tyr Phe Gly Pro Gly
        115                 120                 125

Thr Arg Leu Leu Val Leu Glu Asp Leu Lys Asn Val Phe Pro Pro Glu
130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310

<210> SEQ ID NO 80
<211> LENGTH: 19
<212> TYPE: PRT
<213> ORGANISM: Homo sapiens

<400> SEQUENCE: 80

Met Gly Ile Arg Leu Leu Cys Arg Val Ala Phe Cys Phe Leu Ala Val

<210> SEQ ID NO 81
<211> LENGTH: 114
<212> TYPE: PRT
<213> ORGANISM: Homo sapiens

<400> SEQUENCE: 81

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu

<210> SEQ ID NO 82
<211> LENGTH: 5
<212> TYPE: PRT
<213> ORGANISM: Homo sapiens

<400> SEQUENCE: 82

Met Asp His Glu Asn
1               5

<210> SEQ ID NO 83
<211> LENGTH: 6
<212> TYPE: PRT
<213> ORGANISM: Homo sapiens

<400> SEQUENCE: 83

Ser Tyr Asp Val Lys Met
1               5

<210> SEQ ID NO 84
<211> LENGTH: 16
<212> TYPE: PRT
<213> ORGANISM: Homo sapiens

<400> SEQUENCE: 84

Cys Ala Ser Ser Leu Ser Ser Gly Ser His Gln Glu Thr Gln Tyr Phe
1               5                   10                  15

<210> SEQ ID NO 85
<211> LENGTH: 15
<212> TYPE: PRT
<213> ORGANISM: Homo sapiens

<400> SEQUENCE: 85

Gln Glu Thr Gln Tyr Phe Gly Pro Gly Thr Arg Leu Leu Val Leu
1               5                   10                  15

<210> SEQ ID NO 86
<211> LENGTH: 179
<212> TYPE: PRT
<213> ORGANISM: Homo sapiens

<400> SEQUENCE: 86

Glu Asp Leu Lys Asn Val Phe Pro Pro Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 87
<211> LENGTH: 20
<212> TYPE: PRT
<213> ORGANISM: Homo sapiens

<400> SEQUENCE: 87

Val Ile Gly Phe Arg Ile Leu Leu Leu Lys Val Ala Gly Phe Asn Leu
1               5                   10                  15

Leu Met Thr Leu
            20

<210> SEQ ID NO 88
<211> LENGTH: 23
<212> TYPE: PRT
<213> ORGANISM: Homo sapiens

<400> SEQUENCE: 88

Thr Ile Leu Tyr Glu Ile Leu Leu Gly Lys Ala Thr Leu Tyr Ala Val
1               5                   10                  15

Leu Val Ser Ala Leu Val Leu
            20

<210> SEQ ID NO 89
<211> LENGTH: 274
<212> TYPE: PRT
<213> ORGANISM: Homo sapiens

<400> SEQUENCE: 89

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
                35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
                100                 105                 110

Pro Thr Ser Gly Gly Ser Tyr Ile Pro Thr Phe Gly Arg Gly Thr Ser
            115                 120                 125

Leu Ile Val His Pro Tyr Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 90
<211> LENGTH: 311
<212> TYPE: PRT
<213> ORGANISM: Homo sapiens

<400> SEQUENCE: 90

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
        50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95
```

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Gly Glu Gly Ser Arg
        115                 120                 125

Leu Thr Val Leu Glu Asp Leu Lys Asn Val Phe Pro Pro Glu Val Ala
130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 91
<211> LENGTH: 9
<212> TYPE: PRT
<213> ORGANISM: Homo sapiens

<400> SEQUENCE: 91

Phe Leu Leu Glu Thr Val Val Arg Val
1               5

<210> SEQ ID NO 92
<211> LENGTH: 9
<212> TYPE: PRT
<213> ORGANISM: Homo sapiens

<400> SEQUENCE: 92

Ile Leu Asp Glu His Val Gln Arg Val
1               5

<210> SEQ ID NO 93
<211> LENGTH: 9
<212> TYPE: PRT
<213> ORGANISM: Homo sapiens

<400> SEQUENCE: 93

Ile Val Met Glu His Val Val Phe Leu
1               5

<210> SEQ ID NO 94
<211> LENGTH: 9
<212> TYPE: PRT
<213> ORGANISM: Homo sapiens

<400> SEQUENCE: 94

Lys Ile Leu Glu Asp Val Val Gly Val
1               5

<210> SEQ ID NO 95
<211> LENGTH: 9
<212> TYPE: PRT
<213> ORGANISM: Homo sapiens

<400> SEQUENCE: 95

Lys Leu Leu Asp Leu Gln Val Arg Val
1               5

<210> SEQ ID NO 96
<211> LENGTH: 9
<212> TYPE: PRT
<213> ORGANISM: Homo sapiens

<400> SEQUENCE: 96

Lys Val Leu Asp Lys Val Phe Arg Ala
1               5

<210> SEQ ID NO 97
<211> LENGTH: 9
<212> TYPE: PRT
<213> ORGANISM: Homo sapiens

<400> SEQUENCE: 97

Lys Val Leu Glu Ile Leu His Arg Val
1               5

<210> SEQ ID NO 98
<211> LENGTH: 9
<212> TYPE: PRT
<213> ORGANISM: Homo sapiens

<400> SEQUENCE: 98

Lys Val Leu Glu Arg Val Asn Ala Val
1               5

<210> SEQ ID NO 99
<211> LENGTH: 9
<212> TYPE: PRT
<213> ORGANISM: Homo sapiens

<400> SEQUENCE: 99

Lys Val Leu Glu Thr Leu Val Thr Val
1               5

<210> SEQ ID NO 100
<211> LENGTH: 9
<212> TYPE: PRT
<213> ORGANISM: Homo sapiens

<400> SEQUENCE: 100

Lys Val Leu Gly Ile Val Val Gly Val
1               5

```
<210> SEQ ID NO 101
<211> LENGTH: 9
<212> TYPE: PRT
<213> ORGANISM: Homo sapiens

<400> SEQUENCE: 101

Ser Leu Leu Met Trp Ile Thr Gln Val
1               5
```

TRANSFECTED T-CELLS AND T-CELL RECEPTORS FOR USE IN IMMUNOTHERAPY AGAINST CANCERS

CROSS REFERENCE TO RELATED APPLICATIONS

This application is a Continuation application of U.S. patent application Ser. No. 15/460,654, filed Mar. 16, 2017, which claims the benefit of U.S. Provisional Application Ser. No. 62/308,975, filed 16 Mar. 2016, and Great Britain Application No. 1604492.7, filed 16 Mar. 2016, the content of each of these applications is herein incorporated by reference in their entirety.

This application also is related to PCT/EP2017/056260 filed 16 Mar. 2017, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000058-002002_Sequence_Listing_ST25.txt" created on 15 Apr. 2019, and 49,190 bytes in size) is submitted concurrently with the instant application, and the entire contents of the Sequence Listing are incorporated herein by reference.

BACKGROUND

T-cell based immunotherapy targets peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are expressed and, as compared to unaltered cells of the same origin, usually up-regulated in cells of the respective tumor.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

MAGEA4 is a member of the MAGEA gene family. Expression of the MAGEA4 protein and mRNA has been linked to the development and prognosis of various cancers. MAG-003 peptide, i.e., KVLEHVVRV (SEQ ID NO:1), is an HLA-A*0201-restricted cytotoxic T lymphocyte (CTL) epitope of MAGEA4 (amino acids 286-294). (Jia et al. 2010; Wu et al. 2011), the contents of which are hereby incorporated by reference in their entirety. MAG-003 elicits peptide-specific CTLs both in vitro from HLA-A*0201-positive PBMCs and in HLA-A*0201/Kb transgenic mice. MAG-003-induced CTLs lyse target-cells in an HLA-A*0201-restricted fashion, demonstrating that MAG-003 is an HLA-A*0201-restricted CTL epitope.

There are two classes of MHC-molecules, MHC class I and MHC class II. Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. Since both types of response, CD8 and CD4 dependent, contribute jointly and synergistically to the anti-tumor effect, the identification and characterization of tumor-associated antigens and corresponding T cell receptors is important in the development of cancer immunotherapies such as vaccines and cell therapies.

In the MHC class I dependent immune reaction, peptides not only have to be able to bind to certain MHC class I molecules expressed by tumor cells, they subsequently also have to be recognized by T-cells bearing specific T-cell receptors (TCR). Therefore, TAAs are a starting point for the development of a T-cell based therapy including but not limited to tumor vaccines and cell therapies.

In the case of targeting peptide-MHC by specific TCRs (e.g., soluble TCRs or cell-surface TCRs) and antibodies or other binding molecules (complexes) according to the description, the immunogenicity of the underlying peptides is secondary. In these cases, the presentation is a determining factor.

While advances have been made in the development of molecular-targeting drugs for cancer therapy, there remains a need in the art to develop new anti-cancer agents that specifically target molecules highly specific to cancer cells. The present description addresses that need by providing novel MAG-003 TCRs, nucleic acids, vectors and host cells which specifically bind MAG-003; and methods of using such molecules in the treatment of cancer.

SUMMARY

The present description relates to T-cell receptors (TCRs) comprising an alpha chain and/or a beta chain ("alpha/beta TCRs"). In another embodiment, the present description relates to TCRs comprising a gamma chain and/or delta chain ("gamma/delta TCRs").

The present description further relates to TCRs, individual TCR subunits (alone or in combination), and subdomains thereof, soluble TCRs (sTCRs), for example, soluble alpha/beta dimeric TCRs having at least one disulfide interchain bond between constant domain residues that are not present in native TCRs, and cloned TCRs, said TCRs engineered into autologous or allogeneic T-cells or T-cell progenitor cells, and methods of making same, as well as other cells bearing said TCR.

The present description further relates to a TCR that specifically binds to a MAG-003 peptide-HLA molecule complex, wherein the MAG-003 peptide is selected from KVLEHVVRV (SEQ ID NO:1) and variants thereof, such as those shown in SEQ ID NO:2 to SEQ ID NO:24. In an embodiment the HLA molecule is HLA-A*02.

The present description further relates to TCRs comprising, a TCR alpha variable domain that has at least 75%, 80%, 90%, 95%, 98%, or 99% sequence identity, preferably 90% sequence identity, to a TCR alpha variable domain shown in Table 2; and the TCR beta variable domain has at least at least 75%, 80%, 90%, 95%, 98%, or 99% sequence identity, preferably 90% sequence identity, to a TCR beta variable domain shown in Table 2.

In an embodiment, the TCR alpha variable domain has at least one mutation relative to a TCR alpha domain shown in Table 2; and/or the TCR beta variable domain has at least one mutation relative to a TCR alpha domain shown in Table 2. In an embodiment, a TCR comprising at least one mutation in the TCR alpha variable domain and/or TCR beta variable domain has a binding affinity for, and/or a binding half-life for, a MAG-003 peptide-HLA molecule complex, which is at least double that of a TCR comprising the unmutated TCR alpha domain and/or unmutated TCR beta variable domain.

The TCR alpha chains of the present description may further comprise a TCR alpha constant domain that has at least 70%, 75%, 80%, 90%, 95%, 98%, or 99% sequence identity to a TCR alpha constant domain shown in Table 2. The TCR beta chains of the present description may further comprise a TCR beta constant domain that has at least 70%, 75%, 80%, 90%, 95%, 98%, or 99% sequence identity to a TCR beta constant domain shown in Table 2.

The TCR alpha chains of the present description may further comprise a TCR alpha transmembrane domain and/or a TCR alpha intracellular domain. The TCR beta chains of the present description may further comprise a TCR beta transmembrane domain and/or a TCR beta intracellular domain.

The description further relates to TCR alpha chains comprising one or more alpha chain complementarity determining regions (CDRs) disclosed in Table 2, and variants thereof having one, two, three or four substitutions relative to the CDRs shown in Table 2. Further described are TCR alpha chains comprising at least one CDR selected from a CDR1, CDR2 and CDR3 shown in Table 2. Further described are TCR alpha chains comprising an alpha chain CDR3 shown in Table 2.

The description further relates to TCR beta chains comprising one or more beta chain complementarity determining regions (CDRs) disclosed in Table 2, and variants thereof having one, two, three or four substitutions relative to the CDRs shown in Table 2. Further described are TCR beta chains comprising at least one CDR selected from a beta chain CDR1, CDR2 and CDR3 shown in Table 2. Further described are TCR beta chains comprising a beta chain CDR3 shown in Table 2.

The description further relates to an isolated or recombinant nucleic acid comprising a nucleotide sequence encoding a TCR of the present description. In an embodiment, nucleic acids of the description encode a TCR alpha chain and/or a TCR beta chain as shown in Table 2.

The description further relates to a recombinant expression vector comprising a nucleic acid encoding a TCR alpha chain, beta chain, or both, as described herein.

The description further relates to an isolated host cell comprising a recombinant expression vector expressing a nucleic acid encoding the TCR alpha chain, beta chain, or both, as described herein.

The description further relates to an isolated host cell comprising a recombinant expression vector according to the present description, preferably wherein the cell is a human cell, preferably a peripheral blood lymphocyte (PBL), more preferably a CD4 or CD8 positive T lymphocyte.

The description further relates to an isolated PBL comprising the recombinant expression vector of the description, wherein the PBL is a CD8+ T-cell or a CD4+ T-cell.

The description further relates to a population of cells comprising at least one host cell described herein.

The description further relates to TCRs and host cells of the present description for use in the treatment of proliferative diseases, such as, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

In an aspect, the host cell is a CD8+ T-cell or a CD4+ T-cell transfected with a nucleic acid encoding at least one TCR according to the description, wherein the TCR comprises at least one amino acid sequence disclosed in Table 2. In another aspect such host cells are used in the immunotherapy of small cell lung cancer, non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably non-small cell lung cancer.

The description further relates to methods of killing or reducing the number of cancer cells comprising contacting the cancer cells with a TCR, nucleic acid, vector or host cell as described herein. Also provided are methods of treating cancer comprising administering to a subject in need thereof a TCR, nucleic acid, vector or host cell as described herein.

In another aspect, the present description relates to a MAG-003 peptide, for example an isolated peptide, comprising an amino acid sequence according to the following general formula I:

Formula I $$X_1X_2LEHVVRX_3 \quad \text{(SEQ ID NO: 25)}$$

wherein $X_1$ is selected from the amino acids K and Y, $X_2$ is selected from the amino acids V, L and A, and $X_3$ is selected from V, L, A, and I, wherein said peptide binds to an HLA class I or class II molecule and/or induces T-cells cross-reacting with said peptide, or a pharmaceutically acceptable salt thereof. In an aspect, said peptide is not the underlying full-length polypeptide.

Preferred is a sequence selected from the group consisting of SEQ ID NO:1 or a variant sequence thereof which is at least 66%, preferably at least 77%, and more preferably at least 88% homologous (preferably at least 77% or at least 88% identical) to SEQ ID NO:1, wherein said variant binds to an HLA class I or class II molecule and/or induces T-cells cross-reacting with said peptide, or a pharmaceutically acceptable salt thereof, wherein said peptide is not the underlying full-length polypeptide.

The present description further relates to a peptide of the present description comprising a sequence that is selected from the group consisting of SEQ ID NO:1 or a variant thereof, which is at least 66%, preferably at least 77%, and more preferably at least 88% homologous (preferably at least 77% or at least 88% identical) to SEQ ID NO:1, wherein said peptide or variant thereof has an overall length of between 8 and 100, preferably between 8 and 30, and most preferably of between 8 and 14 amino acids.

The following tables show example peptides according to the present description, and their respective SEQ ID NOs. In an aspect, the peptides in Table 1 may bind to HLA-A*02. In another aspect, TCRs described herein are capable of binding or specifically binding to one or more peptides in Table 1.

TABLE 1

Peptides according to the present description

| SEQ ID NO: | Sequence |
|---|---|
| 1 | KVLEHVVRV |
| 2 | KVLEHVVRL |
| 3 | KVLEHVVRA |
| 4 | KVLEHVVRI |
| 5 | KLLEHVVRV |
| 6 | KLLEHVVRL |
| 7 | KLLEHVVRA |
| 8 | KLLEHVVRI |
| 9 | KALEHVVRV |
| 10 | KALEHVVRL |
| 11 | KALEHVVRA |
| 12 | KALEHVVRI |
| 13 | YLLEHVVRV |
| 14 | YLLEHVVRL |
| 15 | YLLEHVVRA |
| 16 | YLLEHVVRI |
| 17 | YALEHVVRV |
| 18 | YALEHVVRL |
| 19 | YALEHVVRA |
| 20 | YALEHVVRI |
| 21 | YVLEHVVRV |
| 22 | YVLEHVVRL |
| 23 | YVLEHVVRA |
| 24 | YVLEHVVRI |

In an aspect, the present description relates to the treatment of proliferative diseases, such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer by utilizing one or more peptides described herein.

Particularly preferred are the peptides—alone or in combination—according to the present description selected from the group consisting of SEQ ID NO:1 to SEQ ID NO:24. More preferred are the peptides—alone or in combination—selected from the group consisting of SEQ ID NO:1 to SEQ ID NO:24 (see Table 1), and their uses in the immunotherapy of non-small cell lung cancer, small cell lung cancer, renal cell cancer, brain cancer, gastric cancer, colorectal cancer, hepatocellular cancer, head and neck cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably non-small cell lung cancer.

In an aspect, the present description relates to peptides according to the present description that have the ability to bind to a molecule of HLA class-I or—in a longer form, such as a length-variant—HLA class-II.

In an aspect, the present description relates to the peptides according to the present description wherein said peptides (each) comprise, consist of, or consist essentially of an amino acid sequence according to SEQ ID NO:1 to SEQ ID NO:24.

The present description further relates to the peptides according to the present description, wherein said peptide is modified and/or includes non-peptide bonds.

The present description further relates to the peptides according to the present description, wherein said peptide is part of a fusion protein, in particular fused to the N-terminal amino acids of the HLA-DR antigen-associated invariant chain (Ii), preferably the 80 N-terminal amino acids thereof, or fused to (or into the sequence of) an antibody, such as, for example, an antibody that is specific for dendritic cells.

The description further relates to a nucleic acid encoding the peptides according to the description. The description further relates to the nucleic acid according to the description that is DNA, cDNA, PNA, RNA or combinations thereof.

The description further relates to an expression vector capable of expressing and/or expressing a nucleic acid according to the description.

The description further relates to a peptide according to the description, a nucleic acid according to the description or an expression vector according to the description for use in the treatment of diseases and in medicine, in particular in the treatment of cancer.

The description further relates to antibodies that specifically bind the peptides according to the present description or complexes of said peptides according to the description with MHC, and methods of making such antibodies.

The description further relates to a host cell comprising a nucleic acid according to the description or an expression vector as described before.

The description further relates to the host cell according to the description that is an antigen presenting cell, and preferably is a dendritic cell.

The description further relates to a method for producing a peptide according to the description, the method comprising culturing the host cell according to the description, and isolating the peptide from said host cell or its culture medium.

The description further relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The description further relates to the method according to the description, wherein the antigen-presenting cell comprises an expression vector capable of expressing or expressing said peptide containing SEQ ID NO:1 to SEQ ID NO:24, preferably containing SEQ ID NO:1 to SEQ ID NO:24, or a variant amino acid sequence thereof.

The description further relates to activated T-lymphocytes, produced by the method according to the description, wherein a T-cell selectively recognizes a cell which expresses a polypeptide comprising an amino acid sequence according to the description.

The description further relates to methods of killing cancer and/or suppressing cells in a patient which cancer cells aberrantly express a polypeptide comprising any amino acid sequence according to the description, the methods comprising administering to the patient an effective number of T-cells as produced according to the description.

The description further relates to the use of any peptide described herein, nucleic acids according described herein, expression vectors described herein, cells described herein, activated T lymphocyte described herein, T-cell receptors, antibodies, or other peptide- and/or peptide-MHC-binding molecules according to the present description as a medicament or in the manufacture of a medicament. In an aspect, the medicament is active against cancer.

Preferably, said medicament is a cellular therapy, a vaccine or a protein based on a TCR, a soluble TCR or antibody.

The present description further relates to a use according to the present description, wherein the cancer cells are non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably non-small cell lung cancer.

The present description further relates to biomarkers based on the peptides according to the present description, herein called "targets," that can be used in the diagnosis of cancer, preferably non-small cell lung cancer. The marker can be the over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC. Optionally the antibody or soluble TCR carries a further effector function such as an immune stimulating domain or toxin.

The present description further relates to the use of these novel targets for the identification of TCRs that recognize at least one of said targets, and preferably the identification of said TCRs that activate T-cells.

The present description also relates to the use of these novel targets in the context of cancer treatment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
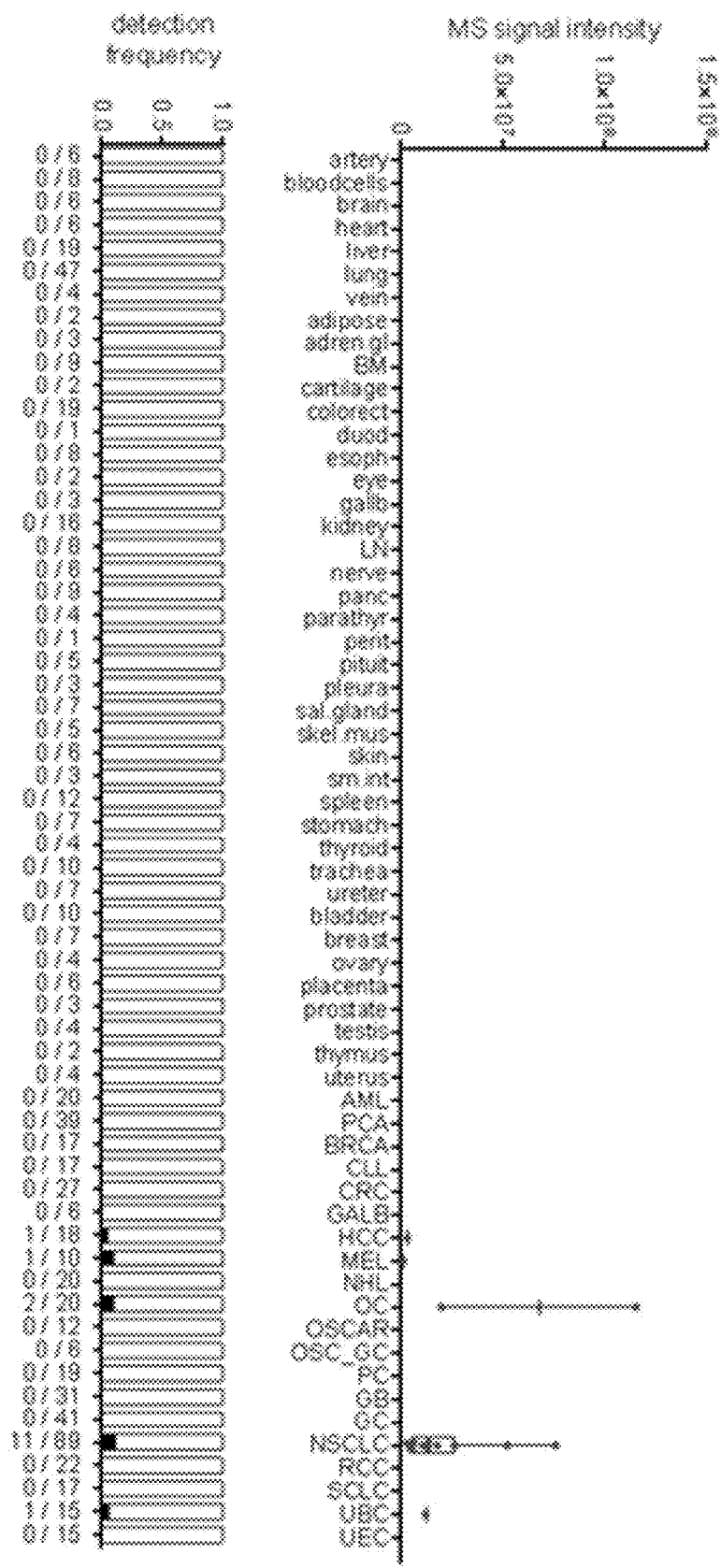
FIG. 1 shows MAG-003 peptide presentation in healthy tissues and cancers.

The present description relates to T-cell receptors (TCRs) comprising an alpha chain and/or a beta chain ("alpha/beta TCRs"). Also provided are MAG-003 peptides capable of binding to TCRs and antibodies when presented by an MHC molecule. The present description also relates to nucleic acids, vectors and host cells for expressing TCRs and peptides of the present description; and methods of using the same.

The object of the invention is therefore solved in a first aspect by an antigen recognizing construct comprising at least one complementary determining region (CDR) 3 having at least 50%, 60%, 70%, 80%, 90%, 95%, 98%, 99%, or preferably 100% sequence identity to an amino acid sequence selected from SEQ ID NOs. 44, 52, 60, 68, 76, and 84.

The antigen recognizing construct according to the invention is preferably selected from an antibody, or derivative or fragment thereof, or a T cell receptor (TCR), or derivative or fragment thereof. A derivative or fragment of an antibody or TCR of the invention shall preferably retain the antigen binding/recognizing ability of the parent molecule, in particular its specificity and/or selectivity as explained above. Such binding functionality may be retained by the presence of a CDR3 region as defined herein.

In an embodiment of the invention, the inventive TCRs are able to recognize TAA antigens in a major histocompatibility complex (MHC) class I-dependent manner. "MHC class I-dependent manner," as used herein, means that the TCR elicits an immune response upon binding to TAA antigens within the context of an MHC class I molecule. The MHC class I molecule can be any MHC class I molecule known in the art, e.g., HLA-A molecules. In a preferred embodiment of the invention, the MHC class I molecule is an HLA-A*02 molecule.

The invention provides both single chain antigen recognizing construct and double chain recognizing constructs.

In an embodiment, the TCR alpha variable domain has at least one mutation relative to a TCR alpha domain shown in Table 2; and/or the TCR beta variable domain has at least one mutation relative to a TCR alpha domain shown in Table 2. In an embodiment, a TCR comprising at least one mutation in the TCR alpha variable domain and/or TCR beta variable domain has a binding affinity for, and/or a binding half-life for, an TAA peptide-HLA molecule complex, which is at least double that of a TCR comprising the unmutated TCR alpha domain and/or unmutated TCR beta variable domain.

The TCR alpha chains of the present description may further comprise a TCR alpha transmembrane domain and/or a TCR alpha intracellular domain. The TCR beta chains of the present description may further comprise a TCR beta transmembrane domain and/or a TCR beta intracellular domain.

The invention in particular provides a TCR as antigen recognizing construct, or fragment or derivative thereof. The TCR preferably is of human, which is understood as being generated from a human TCR locus and therefore comprising human TCR sequences. Furthermore, the TCR of the invention may be characterized in that it is of human origin and specifically recognizes a TAA antigen of the invention as mentioned in table 1.

Another embodiment of the invention additionally or alternatively provides the antigen recognizing construct described above, which induces an immune response, preferably wherein the immune response is characterized by an increase in interferon (IFN) γ levels.

TCRs of the invention may be provided as single chain α or β, or γ and δ, molecules, or alternatively as double chain constructs composed of both the α and β chain, or γ and δ chain.

Most preferably, in some additional embodiments, wherein the disclosure refers to antigen recognizing constructs comprising any one, two or all of the CDR1 to CDR3 regions of the herein disclosed TCR chains (see Table 1), such antigen recognizing constructs may be preferred, which comprise the respective CDR sequence of the invention with not more than three, two, and preferably only one, modified amino acid residues. A modified amino acid residue may be selected from an amino acid insertion, deletion or substitution. Most preferred is that the three, two, preferably only one modified amino acid residue is the first or last amino acid residue of the respective CDR sequence. If the modification is a substitution then it is preferable in some embodiments that the substitution is a conservative amino acid substitution.

The inventive TCRs may further comprise a constant region derived from any suitable species, such as any mammal, e.g., human, rat, monkey, rabbit, donkey, or mouse. In an embodiment of the invention, the inventive TCRs further comprise a human constant region. In some preferred embodiments, the constant region of the TCR of the invention may be slightly modified, for example, by the introduction of heterologous sequences, preferably mouse sequences, which may increase TCR expression and stability.

In an embodiment of the invention, chimeric TCR are provided, wherein the TCR chains comprise sequences from multiple species. Preferably, a TCR of the invention may comprise an α chain comprising a human variable region of an α chain and, for example, a murine constant region of a murine TCR α chain.

In one embodiment, the TCR of the invention is a human TCR comprising human variable regions according to the above embodiments and human constant regions.

In some embodiments the antigen recognizing construct is murinized or humanized. These terms are used when amino acid sequences from a foreign species are introduced into a construct of the invention.

The TCR of the invention may be provided as a single chain TCR (scTCR). A scTCR according to the invention shall comprise in one polypeptide chain a full or partial alpha chain sequence and a full or partial beta chain sequence, preferably connected via a peptide linker.

A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide, which joins together two single chains, as described herein. Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, or other interconnecting molecule/linker, and wherein said scTCRs are interconnected by biotin-streptavidin interaction to allow the formation of said multimeric complex. Similar approaches known in the art for the generation of multimeric TCR are also possible and included in this disclosure. Also provided are multimeric complexes of a higher order, comprising more than two scTCR of the invention.

For the purposes of the present invention, a TCR is a moiety having at least one TCR alpha or gamma and/or TCR beta or delta variable domain. Generally, they comprise both a TCR alpha variable domain and a TCR beta variable domain, alternatively both a TCR gamma variable domain and a TCR delta variable domain. They may be αβ/γδ heterodimers or may be in single chain format. For use in adoptive therapy, an αβ or γδ heterodimeric TCR may, for example, be transfected as full length chains having both cytoplasmic and transmembrane domains. If desired, an introduced disulfide bond between residues of the respective constant domains may be present.

In a preferred embodiment, the antigen recognizing construct is a human TCR, or fragment or derivative thereof. A human TCR or fragment or derivative thereof is a TCR, which comprises over 50% of the corresponding human TCR sequence. Preferably, only a small part of the TCR sequence is of artificial origin or derived from other species. It is known, however, that chimeric TCRs, e.g. derived from human origin with murine sequences in the constant domains, are advantageous. Particularly preferred are, therefore, TCRs in accordance with the present invention, which contains murine sequences in the extracellular part of their constant domains.

Thus, it is also preferred that the inventive antigen recognizing construct is able to recognize its antigen in a human leucocyte antigen (HLA) dependent manner, preferably in a HLA-A02 dependent manner. The term "HLA dependent manner" in the context of the present invention means that the antigen recognizing construct binds to the antigen only in the event that the antigenic peptide is presented by said HLA.

The antigen recognizing construct in accordance with the invention in one embodiment preferably induces an immune response, preferably wherein the immune response is characterized by the increase in interferon (IFN) γ levels.

Also provided by the invention is a polypeptide comprising a functional portion of any of the TCRs (or functional variants thereof) described herein, for examples, of any one of the TCRs as provided in the example section and table 2. The term "poly-peptide" as used herein includes oligopeptides and refers to a single chain of amino acids connected by one or more peptide bonds. With respect to the inventive polypeptides, the functional portion can be any portion comprising contiguous amino acids of the TCR (or functional variant thereof), of which it is a part, provided that the functional portion specifically binds to the TAA antigen, preferably as disclosed herein in Table 1. The term "functional portion" when used in reference to a TCR (or functional variant thereof) refers to any part or fragment of the TCR (or functional variant thereof) of the invention, which part or fragment retains the biological activity of the TCR (or functional variant thereof), of which it is a part (the parent TCR or parent functional variant thereof). Functional portions encompass, for example, those parts of a TCR (or functional variant thereof) that retain the ability to specifically bind to the TAA antigen (in an HLA dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR variable sequences (or functional variant thereof).

The functional portion can comprise additional amino acids at the amino or carboxy terminus of the portion, or at both termini, in which additional amino acids are not found in the amino acid sequence of the parent TCR or functional variant thereof. Desirably, the additional amino acids do not interfere with the biological function of the functional portion, e.g., specifically binding to the TAA antigens; and/or having the ability to detect cancer, treat or prevent cancer, etc. More desirably, the additional amino acids enhance the biological activity, as compared to the biological activity of the parent TCR or functional variant thereof.

In some instances, the construct of the invention may comprise one or two polypeptide chains comprising a sequences according to any of the SEQ ID NO: 39 to 86 (CDR sequences, constant and variable regions and full length sequences), or functional fragments thereof, and further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide may include any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. In some embodiments of the invention, the TCRs (and functional portions and functional variants thereof), polypeptides, and proteins of the invention may be expressed as a single protein comprising a linker peptide linking the α chain and the β chain, and linking the γ chain and the δ chain. In this regard, the TCRs (and functional variants and functional portions thereof), polypeptides, and proteins of the invention comprising the amino acid sequences of the variable regions of the TCR of the invention and may further comprise a linker pep-tide. The linker peptide may advantageously facilitate the expression of a recombinant TCR (including functional portions and functional variants thereof), polypeptide, and/or protein in a host cell. The linker peptide may comprise any suitable amino acid sequence. Linker sequences for single chain TCR constructs are well known in the art. Such a single chain construct may further comprise one, or two, constant domain sequences. Upon expression of the construct including the linker peptide by a host cell, the linker peptide may also be cleaved, resulting in separated α and β chains, and separated γ and δ chain.

As already mentioned above, the binding functionality of the TCR of the invention may be provided in the framework of an antibody. For example, CDR sequences of the TCR of the invention, possibly including additional 3, 2 or 1 N and/or C terminal framework residues, may be directly grafted into an antibody variable heavy/light chain sequence. The term "antibody" in its various grammatical forms is used herein to refer to immunoglobulin molecules and immunologically active portions of immunoglobulin molecules, i.e., molecules that contain an antigen-binding site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or pol-ymeric form.

The term "antibody" includes, but is not limited to, genetically engineered or otherwise modified forms of immunoglobulins, such as intrabodies, chimeric antibodies, fully human antibodies, humanized antibodies (e.g. generated by "CDR-grafting"), antibody fragments, and heteroconjugate antibodies (e.g., bispecific antibodies, diabodies, triabodies, tetra-bodies, etc.). The term "antibody" includes cys-diabodies and minibodies. Thus, each and every embodiment provided herein in regard to "antibodies", or "antibody like constructs" is also envisioned as, bi-specific antibodies, diabodies, scFv fragments, chimeric antibody receptor (CAR) constructs, diabody and/or minibody embodiments, unless explicitly denoted otherwise. The term "antibody" includes a polypeptide of the immunoglobulin family or a polypeptide comprising fragments of an immunoglobulin that is capable of non-covalently, reversibly, and in a specific manner binding a corresponding antigen, preferably the TAA of the invention, as disclosed herein. An exemplary antibody structural unit comprises a tetramer. In some embodiments, a full length antibody can be composed of two identical pairs of polypeptide chains, each pair having one "light" and one "heavy" chain (connected through a disulfide bond). Antibody structure and isotypes are well known to the skilled artisan (for example from Janeway's Immunobiology, 9th edition, 2016).

The recognized immunoglobulin genes of mammals include the kappa, lambda, alpha, gamma, delta, epsilon, and mu constant region genes, as well as the myriad immunoglobulin variable region genes (for more information on immunoglobulin genes see the international Im-MunoGeneTics information System®, Lefranc M-P et al, Nucleic Acids Res. 2015 January; 43(Database issue):D413-22; and www.imgt.org). For full-length chains, the light chains are classified as either kappa or lambda. For full-length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this invention, an "antibody" en-compasses all variations of antibody and fragments thereof. Thus, within the scope of this concept are full length antibodies, chimeric antibodies, humanized antibodies, single chain antibodies (scFv), Fab, Fab', and multimeric versions of these fragments (e.g., F(ab')2) with the same, essentially the same or similar binding specificity. In some embodiments, the antibody binds specifically to a peptide TAA of the invention. Preferred antigen recognizing constructs according to the invention include an antibody heavy chain, preferably the variable domain thereof, or an antigen binding fragment thereof, and/or an antibody light chain, preferably the variable domain thereof, or an antigen binding fragment thereof. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles). In some instances, the TCR CDR3 sequence may be slightly modified, but preferably by not more than 3 amino acid residues, preferably only two and most preferably only one amino acid position, as compared to the CDR3 sequences provided in SEQ ID Nos: 44, 52, 60, 68, 76, and 84. Preferably, the antibodies comprise the CDR3, preferably all of CDR1 to CDR3 regions in the combination, as indicated for the TCR of the invention in table 2, in each case independently, optionally with not more than three or two, preferably one, amino acid substitution(s), insertion(s) and/ or deletion(s) compared to these sequences.

Suitable methods of making antibodies are known in the art. For instance, standard hybridoma methods are described in, e.g., Kohler and Milstein, Eur. J. Immunol, 5, 511-519 (1976), Harlow and Lane (eds.), Antibodies: A Laboratory Manual, CSH Press (1988), and C. A. Janeway et al. (eds.), Immunobiology, 8 Ed., Garland Publishing, New York, N.Y. (2011)). Alternatively, other methods, such as EBV-hybridoma methods (Haskard and Archer, J. Immunol. Methods, 74(2), 361-67 (1984), and Roder et al, Methods Enzymol, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266.

Some embodiments of the invention also pertain to TCRs, or functional fragments and polypeptides thereof, which are soluble TCRs. As used herein, the term "soluble T-cell receptor" refers to heterodimeric truncated variants of native TCRs, which comprise extracellular portions of the TCR α-chain and β-chain, for example linked by a disulfide bond, but which lack the transmembrane and cytosolic domains of the native protein. The terms "soluble T-cell receptor α-chain sequence and soluble T-cell receptor β-chain sequence" refer to TCR α-chain and β-chain sequences that lack the transmembrane and cytosolic domains. The sequence (amino acid or nucleic acid) of the soluble TCR α-chain and β-chains may be identical to the corresponding sequences in a native TCR or may comprise variant soluble TCR α-chain and β-chain sequences, as compared to the corresponding native TCR sequences. The term "soluble T-cell receptor" as used herein encompasses soluble TCRs with variant or non-variant soluble TCR α-chain and β-chain sequences. The variations may be in the variable or constant regions of the soluble TCR α-chain and β-chain sequences and can include, but are not limited to, amino acid deletion, insertion, substitution mutations as well as changes to the nucleic acid sequence, which do not alter the amino acid sequence. Soluble TCR of the invention in any case retain the binding functionality of their parent molecules.

Definitions

As used herein and except as noted otherwise all terms are defined as given below.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule.

The term "T-cell response" means the specific proliferation and activation of effector functions induced by a peptide in vitro or in vivo. For MHC class I restricted cytotoxic T-cells, effector functions may be lysis of peptide-pulsed, peptide-precursor pulsed or naturally peptide-presenting target-cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 or longer, and in case of MHC class II peptides (longer variants of the peptides of the description) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present description differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the description, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the description as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present description), if it is capable of inducing an immune response. In the case of the present description, immunogenicity is more specifically defined as the ability to induce a T-cell response. Thus, an "immunogen" would be a molecule that is capable of inducing an immune response, and in the case of the present description, a molecule capable of inducing a T-cell response. In another aspect, the immunogen can be the peptide, the complex of the peptide with MHC, oligopeptide, and/or protein that is used to raise specific antibodies or TCRs against it.

A class I T-cell "epitope" requires a short peptide that is bound to a class I MHC receptor, forming a ternary complex (MHC class I alpha chain, beta-2-microglobulin, and peptide) that can be recognized by a T-cell bearing a matching T-cell receptor binding to the MHC/peptide complex with appropriate affinity. Peptides binding to MHC class I molecules are typically 8-14 amino acids in length, and most typically 9 amino acids in length.

The nucleotide sequence coding for a particular peptide, oligopeptide, or polypeptide may be naturally occurring or they may be synthetically constructed. Generally, DNA segments encoding the peptides, polypeptides, and proteins of this description are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein the term "a nucleotide coding for (or encoding) a TCR" refers to one or more nucleotide sequences coding for the TCR including artificial (man-made) start and stop codons compatible for the biological system the sequence is to be expressed by, for example, T-cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. In an aspect, such polynucleotides are part of a vector and/or such polynucleotides or polypeptides are part of a composition, and still are isolated in that such vector or composition is not part of its natural environment.

The polynucleotides, and recombinant or immunogenic polypeptides, disclosed in accordance with the present description may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present description, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present description can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present description, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

$$\text{percent identity} = 100[1-(C/R)]$$

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iv) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

In the description, the term "homologous" refers to the degree of identity (see percent identity above) between sequences of two amino acid sequences, i.e., peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T-cells induced by a variant of a specific peptide will be able to cross-react with the peptide itself (Appay et al., 2006; Colombetti et al., 2006; Fong et al., 2001; Zaremba et al., 1997).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide having the given amino acid sequence selected from the group consisting of SEQ ID NO:1 to SEQ ID NO:24. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T-lymphocytes. Similarly, a TCR may be modified so that it at least maintains, if not improves, the ability to interact with and bind to a suitable MHC molecule/KVLEHVVRV (SEQ ID NO:1) complex, such as HLA-A*02 or -DR, and in that way it at least maintains, if not improves, the ability to activate T-cells.

These T-cells can subsequently cross-react with cells and kill cells that express a polypeptide that contains the natural amino acid sequence of the cognate peptide, such as KVLEHVVRV (SEQ ID NO:1), as defined in the aspects of the description. As can be derived from the scientific literature and databases (Rammensee et al., 1999; Godkin et al., 1997), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. In an aspect, one skilled in the art would have the ability given the teachings of the description to modify the amino acid sequence of a TCR, by maintaining the known anchor residues, and would be able to determine whether such TCR variants maintain the ability to bind MHC class I or II molecules/KVLEHVVRV (SEQ ID NO:1) complexes. The TCR variants of the description retain the ability to bind MHC class I or II molecules/KVLEHVVRV (SEQ ID NO:1) complexes. T-cells expressing the TCR variants of the description can subsequently kill cells that express a polypeptide containing the natural amino acid sequence of the cognate peptide, such as KVLEHVVRV (SEQ ID NO:1).

In an aspect, the peptides or TCRs disclosed herein can be modified by the substitution of one or more residues at different, possibly selective, sites within the peptide chain, if not otherwise stated. Preferably those substitutions are located at the end of the amino acid chain of said peptide. For TCRs, preferably those substitutions are located at variable domains of TCR alpha chain and TCR beta chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

In an aspect, such substitutions may involve structures other than the common L-amino acids. Thus, D-amino acids might be substituted for the L-amino acids commonly found in the antigenic peptides of the description and yet still be encompassed by the disclosure herein. In addition, non-standard amino acids (i.e., other than the common naturally occurring proteinogenic amino acids) may also be used for substitution purposes to produce immunogens and immunogenic polypeptides according to the present description.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

As used herein, the term "murine" or "human," when referring to an antigen recognizing construct, or a TCR, or any component of a TCR described herein (e.g., complementarity determining region (CDR), variable region, constant region, α chain, and/or β chain), means a TCR (or component thereof), which is derived from a mouse or a human unrearranged TCR locus, respectively.

T-Cell Receptors (TCRs)

In a preferred embodiment, the description relates a TCR comprising a TCR alpha chain shown in Table 2, and variants thereof; and a TCR beta chain shown in Table 2, and variants thereof. In an aspect, a TCR described herein has the ability to bind or specifically bind to a molecule of the human major histocompatibility complex (MHC) class-I/KVLEHVVRV (SEQ ID NO:1)/complex or to class II/KVLEHVVRV (SEQ ID NO:1)/complex.

TABLE 2

Representative TCRs according to present description

| TCR ID | Description | Sequence |
|---|---|---|
| R20P1H7 alpha chain | alpha chain | MEKMLECAFIVLWLQLGWLSGEDQVTQSPEALRLQEG ESSSLNCSYTVSGLRGLFVVYRQDPGKGPEFLFTLYSA GEEKEKERLKATLTKKESFLHITAPKPEDSATYLCAVQG ENSGYSTLTFGKGTMLLVSPDIQNPDPAVYQLRDSKSS DKSVCLFTDFDSQTNVSQSKDSDVYITDKTVLDMRSMD FKSNSAVAWSNKSDFACANAFNNSIIPEDTFFPSPESSC DVKLVEKSFETDTNLNFQNLSVIGFRILLLKVAGFNLLMT LRLWSS (SEQ ID NO: 39) |
| | L segment (TRAV20) | MEKMLECAFIVLWLQLGWLSG (SEQ ID NO: 40) |
| | V chain (TRAV20) | MEKMLECAFIVLWLQLGWLSGEDQVTQSPEALRLQEG ESSSLNCSYTVSGLRGLFVVYRQDPGKGPEFLFTLYSA GEEKEKERLKATLTKKESFLHITAPKPEDSATYLCAVQ (SEQ ID NO: 41) |
| | CDR1 | VSGLRG (SEQ ID NO: 42) |
| | CDR2 | LYS (SEQ ID NO: 43) |
| | CDR3 | CAVQGENSGYSTLTF (SEQ ID NO: 44) |
| | J segment (TRAJ11) | NSGYSTLTFGKGTMLLVSP (SEQ ID NO: 45) |
| | Constant region (TRAC) | DIQNPDPAVYQLRDSKSSDKSVCLFTDFDSQTNVSQSK DSDVYITDKTVLDMRSMDFKSNSAVAWSNKSDFACAN AFNNSIIPEDTFFPSPESSCDVKLVEKSFETDTNLNFQN LSVIGFRILLLKVAGFNLLMTLRLWSS (SEQ ID NO: 46) |
| R20P1H7 beta chain | beta chain | MGPQLLGYVVLCLLGAGPLEAQVTQNPRYLITVTGKKL TVTCSQNMNHEYMSVVYRQDPGLGLRQIYYSMNVEVT DKGDVPEGYKVSRKEKRNFPLILESPSPNQTSLYFCAS SLGPGLAAYNEQFFGPGTRLTVLEDLKNVFPPEVAVFE PSEAEISHTQKATLVCLATGFYPDHVELSVVWVNGKEVH SGVSTDPQPLKEQPALNDSRYCLSSRLRVSATFWQNP RNHFRCQVQFYGLSENDEVVTQDRAKPVTQIVSAEAWG RADCGFTSESYQQGVLSATILYEILLGKATLYAVLVSALV LMAMVKRKDSRG (SEQ ID NO: 47) |
| | L segment (TRBV27) | MGPQLLGYVVLCLLGAGPL (SEQ ID NO: 48) |
| | V chain (TRBV27) | MGPQLLGYVVLCLLGAGPLEAQVTQNPRYLITVTGKKL TVTCSQNMNHEYMSVVYRQDPGLGLRQIYYSMNVEVT DKGDVPEGYKVSRKEKRNFPLILESPSPNQTSLYFCAS SL (SEQ ID NO: 49) |
| | CDR1 | MNHEY (SEQ ID NO: 50) |
| | CDR2 | SMNVEV (SEQ ID NO: 51) |
| | CDR3 | CASSLGPGLAAYNEQF (SEQ ID NO: 52) |
| | J chain (TRBJ2-1) | YNEQFFGPGTRLTVL (SEQ ID NO: 53) |
| | constant region (TRBC2) | EDLKNVFPPEVAVFEPSEAEISHTQKATLVCLATGFYPD HVELSVVWVNGKEVHSGVSTDPQPLKEQPALNDSRYCL SSRLRVSATFWQNPRNHFRCQVQFYGLSENDEVVTQD RAKPVTQIVSAEAWGRADCGFTSESYQQGVLSATILYEI LLGKATLYAVLVSALVLMAMVKRKDSRG (SEQ ID NO: 54) |

TABLE 2-continued

Representative TCRs according to present description

| TCR ID | Description | Sequence |
|---|---|---|
| R7P1D5 alpha chain | alpha chain | MKTFAGFSFLFLWLQLDCMSRGEDVEQSLFLSVREGD SSVINCTYTDSSSTYLYVVYKQEPGAGLQLLTYIFSNMD MKQDQRLTVLLNKKDKHLSLRIADTQTGDSAIYFCAEYS SASKIIFGSGTRLSIRPNIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRLW SS (SEQ ID NO: 55) |
|  | L segment | MKTFAGFSFLFLWLQLDCMSR (SEQ ID NO: 56) |
|  | V chain (TRAV5) | MKTFAGFSFLFLWLQLDCMSRGEDVEQSLFLSVREGD SSVINCTYTDSSSTYLYVVYKQEPGAGLQLLTYIFSNMD MKQDQRLTVLLNKKDKHLSLRIADTQTGDSAIYFCAE (SEQ ID NO: 57) |
|  | CDR1 | DSSSTY (SEQ ID NO: 58) |
|  | CDR2 | IFS (SEQ ID NO: 59) |
|  | CDR3 | CAEYSSASKIIF ((SEQ ID NO: 60) |
|  | J segment (TRAJ3) | YSSASKIIFGSGTRLSIRP (SEQ ID NO: 61) |
|  | Constant region (TRAC) | NIQNPDPAVYQLRDSKSSDKSVCLFTDFDSQTNVSQSK DSDVYITDKTVLDMRSMDFKSNSAVAWSNKSDFACAN AFNNSIIPEDTFFPSPESSCDVKLVEKSFETDTNLNFQN LSVIGFRILLLKVAGFNLLMTLRLWSS (SEQ ID NO: 62) |
| R7P1D5 beta chain | beta chain | MGSVVTLCCVSLCILVAKHTDAGVIQSPRHEVTEMGQEV TLRCKPISGHDYLFVVYRQTMMRGLELLIYFNNNVPIDDS GMPEDRFSAKMPNASFSTLKIQPSEPRDSAVYFCASRA NTGELFFGEGSRLTVLEDLKNVFPPEVAVFEPSEAEISH TQKATLVCLATGFYPDHVELSVVWVNGKEVHSGVSTDP QPLKEQPALNDSRYCLSSRLRVSATFWQNPRNHFRCQ VQFYGLSENDEVVTQDRAKPVTQIVSAEAWGRADCGFT SESYQQGVLSATILYEILLGKATLYAVLVSALVMAMVK RKDSRG (SEQ ID NO: 63) |
|  | L segment (TRBV12-4) | MGSVVTLCCVSLCILVAKHT (SEQ ID NO: 64) |
|  | V chain (TRBV12-4) | MGSVVTLCCVSLCILVAKHTDAGVIQSPRHEVTEMGQEV TLRCKPISGHDYLFVVYRQTMMRGLELLIYFNNNVPIDDS GMPEDRFSAKMPNASFSTLKIQPSEPRDSAVYFCAS (SEQ ID NO: 65) |
|  | CDR1 | SGHDY (SEQ ID NO: 66) |
|  | CDR2 | FNNNVP (SEQ ID NO: 67) |
|  | CDR3 | CASRANTGELFF (SEQ ID NO: 68) |
|  | J chain (TRBJ2-1) | NTGELFFGEGSRLTVL (SEQ ID NO: 69) |
|  | constant region (TRBC2) | EDLKNVFPPEVAVFEPSEAEISHTQKATLVCLATGFYPD HVELSVVWVNGKEVHSGVSTDPQPLKEQPALNDSRYCL SSRLRVSATFWQNPRNHFRCQVQFYGLSENDEVVTQD RAKPVTQIVSAEAWGRADCGFTSESYQQGVLSATILYEI LLGKATLYAVLVSALVMAMVKRKDSRG (SEQ ID NO: 70) |
| R10P2G12 alpha chain | alpha chain | MLTASLLRAVIASICVVSSMAQKVTQAQTEISVVEKEDV TLDCVYETRDTTYYLFVVYKQPPSGELVFLIRRNSFDEQ NEISGRYSWNFQKSTSSFNFTITASQVVDSAVYFCALSE GNSGNTPLVFGKGTRLSVIANIQNPDPAVYQLRDSKSS DKSVCLFTDFDSQTNVSQSKDSDVYITDKTVLDMRSMD FKSNSAVAWSNKSDFACANAFNNSIIPEDTFFPSPESSC DVKLVEKSFETDTNLNFQNLSVIGFRILLLKVAGFNLLMT LRLWSS (SEQ ID NO: 71) |
|  | L segment (TRAV19) | MLTASLLRAVIASICVVSSM (SEQ ID NO: 72) |
|  | V chain (TRAV19) | MLTASLLRAVIASICVVSSMAQKVTQAQTEISVVEKEDV TLDCVYETRDTTYYLFVVYKQPPSGELVFLIRRNSFDEQ NEISGRYSWNFQKSTSSFNFTITASQVVDSAVYFCALSE (SEQ ID NO: 73) |
|  | CDR1 | TRDTTYY (SEQ ID NO: 74) |
|  | CDR2 | RNSF (SEQ ID NO: 75) |
|  | CDR3 | CALSEGNSGNTPLVF (SEQ ID NO: 76) |
|  | J segment (TRAJ29) | NSGNTPLVFGKGTRLSVIA (SEQ ID NO: 77) |
|  | Constant region (TRAC) | NIQNPDPAVYQLRDSKSSDKSVCLFTDFDSQTNVSQSK DSDVYITDKTVLDMRSMDFKSNSAVAWSNKSDFACAN AFNNSIIPEDTFFPSPESSCDVKLVEKSFETDTNLNFQN LSVIGFRILLLKVAGFNLLMTLRLWSS (SEQ ID NO: 78) |

TABLE 2-continued

Representative TCRs according to present description

| TCR ID | Description | Sequence |
|---|---|---|
| R10P2G12 beta chain | beta chain | MGIRLLCRVAFCFLAVGLVDVKVTQSSRYLVKRTGEKV FLECVQDMDHENMFVVYRQDPGLGLRLIYFSYDVKMKE KGDIPEGYSVSREKKERFSLILESASTNQTSMYLCASSL SSGSHQETQYFGPGTRLLVLEDLKNVFPPEVAVFEPSE AEISHTQKATLVCLATGFYPDHVELSVVWVNGKEVHSG VSTDPQPLKEQPALNDSRYCLSSRLRVSATFWQNPRN HFRCQVQFYGLSENDEVVTQDRAKPVTQIVSAEAWGRA DCGFTSESYQQGVLSATILYEILLGKATLYAVLVSALVLM AMVKRKDSRG (SEQ ID NO: 79) |
|  | L segment (TRBV28) | MGIRLLCRVAFCFLAVGLV (SEQ ID NO: 80) |
|  | V chain (TRBV28) | MGIRLLCRVAFCFLAVGLVDVKVTQSSRYLVKRTGEKV FLECVQDMDHENMFVVYRQDPGLGLRLIYFSYDVKMKE KGDIPEGYSVSREKKERFSLILESASTNQTSMYLCASSL (SEQ ID NO: 81) |
|  | CDR1 | MDHEN (SEQ ID NO: 82) |
|  | CDR2 | SYDVKM (SEQ ID NO: 83) |
|  | CDR3 | CASSLSSGSHQETQYF (SEQ ID NO: 84) |
|  | J chain (TRBJ2-5) | QETQYFGPGTRLLVL (SEQ ID NO: 85) |
|  | constant region (TRBC2) | EDLKNVFPPEVAVFEPSEAEISHTQKATLVCLATGFYPD HVELSVVWVNGKEVHSGVSTDPQPLKEQPALNDSRYCL SSRLRVSATFWQNPRNHFRCQVQFYGLSENDEVVTQD RAKPVTQIVSAEAWGRADCGFTSESYQQGVLSATILYEI LLGKATLYAVLVSALVLMAMVKRKDSRG (SEQ ID NO: 86) |

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchors the alpha and beta chains to the cell membrane.

In the present description, the term "TCR alpha variable domain" therefore refers to the concatenation of the TCR alpha V (TRAV) region without leader region (L), and the TCR alpha J (TRAJ) region; and the term "TCR alpha constant domain" refers to the extracellular TRAC region, or to a C-terminal truncated TRAC sequence, and optionally an alpha transmembrane domain (VIGFRILLLKVAGFN-LLMTL (SEQ ID NO:87)).

Likewise the term "TCR beta variable domain" refers to the concatenation of the TCR beta V (TRBV) region without leader region (L), and the TCR beta D/J (TRBD/TRBJ) region; and the term TCR beta constant domain refers to the extracellular TRBC region, or to a C-terminal truncated TRBC sequence, and optionally a beta transmembrane domain (TILYEILLGKATLYAVLVSALVL (SEQ ID NO:88)).

With respect to gamma/delta TCRs, the term "TCR gamma variable domain" as used herein refers to the concatenation of the TCR gamma V (TRGV) without leader region (L), and TCR gamma J (TRGJ) regions; and the term TCR gamma constant domain refers to the extracellular TRGC region, or to a C-terminal truncated TRGC sequence. Likewise the term "TCR delta variable domain" refers to the concatenation of the TCR delta V (TRDV) without leader region (L), and TCR delta D/J (TRDD/TRDJ) regions; and the term TCR delta constant domain refers to the extracellular TRDC region, or to a C-terminal truncated TRDC sequence.

In an embodiment, a TCR of the present description comprises or consists of a TCR alpha chain at least 75%, 80%, 90%, 91%, 92%, 93%, 94%, 95%, 96%, 97%, 98%, or 99% identical, preferably 90%, 95%, 96%, 97%, 98%, or 99% identical, to a TCR alpha chain shown in Table 2. The TCR alpha chains shown in Table 2 contain a leader (L) segment; a V chain; three complimentary determining regions (CDR1, CDR2 and CDR3); a joining region (J) and a constant region, as defined in Table 2.

In an embodiment, a TCR of the present description comprises or consists of a TCR alpha variable domain at least 75%, 80%, 90%, 91%, 92%, 93%, 94%, 95%, 96%, 97%, 98%, or 99% identical, preferably 90%, 95%, 96%, 97%, 98%, or 99% identical, to a TCR alpha variable domain shown in Table 2.

In an embodiment, a TCR of the present description comprises or consists of, a TCR alpha constant domain at least 75%, 80%, 90%, 91%, 92%, 93%, 94%, 95%, 96%, 97%, 98%, or 99% identical, preferably 75% identical, to a TCR alpha constant domain shown in Table 2.

In an embodiment, a TCR of the present description comprises, or consists of, a TCR alpha variable domain comprising at least one alpha chain complementarity determining region (CDR) selected from the group consisting of an alpha chain CDR1, CDR2 and CDR3 shown in Table 2. In a preferred embodiment, the TCR alpha variable domain comprises an alpha chain CDR3 shown in Table 2. In another preferred embodiment, the TCR alpha variable domain comprises an alpha chain CDR1, CDR2 and CDR3 shown in Table 2.

In a particularly preferred embodiment, a TCR of the present description comprises, or consists of, a TCR alpha variable domain having at least 90% sequence identity to a TCR alpha variable domain of Table 2, and comprises CDR1, CDR2 and CDR3 of the same alpha variable domain of Table 2.

In an embodiment, a TCR of the present description comprises, or consists of, a TCR beta chain at least 75%, 80%, 90%, 91%, 92%, 93%, 94%, 95%, 96%, 97%, 98%, or 99% identical, preferably 90%, 95%, 96%, 97%, 98%, or 99% identical, to a TCR beta chain shown in Table 2. The TCR beta chains shown in Table 2 contain a leader (L) segment; a V chain; three complimentary determining regions (CDR1, CDR2 and CDR3); a joining region (J) and a constant region, as defined in Table 2.

In an embodiment, a TCR of the present description comprises, or consists of, a TCR beta variable domain at least 75%, 80%, 90%, 91%, 92%, 93%, 94%, 95%, 96%, 97%, 98%, or 99% identical, preferably 90%, 95%, 96%, 97%, 98%, or 99% identical, to a TCR beta variable domain shown in Table 2.

In an embodiment, a TCR of the present description comprises, or consists of, a TCR beta constant domain at least 75%, 80%, 90%, 91%, 92%, 93%, 94%, 95%, 96%, 97%, 98%, or 99% identical, preferably 75% identical, to a TCR beta constant domain shown in Table 2.

In an embodiment, a TCR of the present description comprises, or consists of, a TCR beta variable domain comprising at least one beta chain complementarity determining region (CDR) selected from the group consisting of a beta chain CDR1, CDR2 and CDR3 shown in Table 2. In a preferred embodiment, the TCR beta variable domain comprises a beta chain CDR3 shown in Table 2. In another preferred embodiment, the TCR beta variable domain comprises a beta chain CDR1, CDR2 and CDR3 shown in Table 2.

In a particularly preferred embodiment, a TCR of the present description comprises, or consists of, a TCR beta variable domain having at least 90% or 95% sequence identity to a TCR beta variable domain of Table 2, and comprises CDR1, CDR2 and CDR3 of the same TCR beta variable domain of Table 2.

The alpha chain variable domain may comprise one or more alpha CDR domains having one, two, three or four amino acid substitutions relative to the corresponding CDR sequence shown in Table 2. Likewise, the beta chain variable domain may comprise one or more beta CDR domains having one, two, three or four amino acid substitutions relative to the corresponding beta CDR sequence shown in Table 2.

The TCR alpha chain and TCR beta chain may be fused to form a single chain TCR. Alternatively, the TCR alpha and beta chains may be expressed as separate proteins which can be assembled into a heterodimer.

In one embodiment, any TCR alpha chain of Table 2 is paired with any TCR beta chain of Table 2 to produce a TCR that specifically binds to a MAG-003 peptide-HLA molecule complex.

TCR R20P1H7

In one embodiment, a TCR of the present description comprises, or consists of, the alpha chain and/or beta chain of TCR R20P1H7, corresponding to SEQ ID NOs:39 and 47, respectively.

The TCR alpha variable domain of TCR R20P1H7 comprises, or alternatively consists of, amino acids 22 to 133 of SEQ ID NO:39; the TCR alpha constant domain of TCR R20P1H7 comprises, or alternatively consists of, amino acids 134-275 of SEQ ID NO:39; the TCR beta variable domain of TCR R20P1H7 comprises, or alternatively consists of, amino acids 20 to 135 of SEQ ID NO:47; and the TCR beta constant domain comprises, or alternatively consists of, amino acids 136 to 315 of SEQ ID NO:47.

In a particular embodiment, a TCR of the present description comprises a TCR alpha chain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha chain of SEQ ID NO:39.

In another embodiment, a TCR of the present description comprises a TCR alpha variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha variable domain of SEQ ID NO:39.

In an embodiment, a TCR of the present description comprises a TCR alpha constant domain at least 75%, 80%, 90%, 91%, 92%, 93%, 94%, 95%, 96%, 97%, 98%, or 99% identical, preferably 75% identical, to the TCR alpha constant domain of SEQ ID NO:39.

In an embodiment, a TCR of the present description comprises a TCR alpha variable domain comprising at least one alpha chain complementarity determining region (CDR) selected from the group consisting of the alpha chain CDR1, CDR2 and CDR3 of SEQ ID NO:39. In a preferred embodiment, the TCR alpha variable domain comprises the alpha chain CDR3 of SEQ ID NO:39. In another preferred embodiment, the TCR alpha variable domain comprises the alpha chain CDR1, CDR2 and CDR3 of SEQ ID NO:39.

In a particularly preferred embodiment, a TCR of the present description comprises a TCR alpha variable domain having at least 90% or 95% sequence identity to the TCR alpha variable domain of SEQ ID NO:39, and comprises the CDR1, CDR2 and CDR3 of SEQ ID NO:39.

In another particular embodiment, a TCR of the present description comprises a TCR beta chain at least 75%, 80%, 90%, 91%, 92%, 93%, 94%, 95%, 96%, 97%, 98%, or 99% identical, preferably 90%, 95%, 96%, 97%, 98%, or 99% identical, to the TCR beta chain of SEQ ID NO:47.

In an embodiment, a TCR of the present description comprises a TCR beta variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR beta variable domain of SEQ ID NO:47.

In an embodiment, a TCR of the present description comprises a TCR beta constant domain at least 75%, 80%, 90%, 91%, 92%, 93%, 94%, 95%, 96%, 97%, 98%, or 99% identical, preferably 75% identical, to the TCR beta constant domain of SEQ ID NO:47.

In an embodiment, a TCR of the present description comprises a TCR beta variable domain comprising at least one beta chain complementarity determining region (CDR) selected from the group consisting of the beta chain CDR1, CDR2 and CDR3 of SEQ ID NO:47. In a preferred embodiment, the TCR beta variable domain comprises the beta chain CDR3 of SEQ ID NO:47. In another preferred embodiment, the TCR beta variable domain comprises the beta chain CDR1, CDR2 and CDR3 of SEQ ID NO:47.

In a particularly preferred embodiment, a TCR of the present description comprises a TCR beta variable domain having at least 90% or 95% sequence identity to the TCR beta variable domain of SEQ ID NO:47, and comprises CDR1, CDR2 and CDR3 of SEQ ID NO:47.

The alpha chain variable domain may comprise one or more alpha CDR domains having one, two, three or four amino acid substitutions relative to the corresponding CDR sequence of SEQ ID NO:39. Likewise, the beta chain variable domain may comprise one or more beta CDR domains having one, two, three or four amino acid substitutions relative to the corresponding beta CDR sequence of SEQ ID NO:47.

TCR R7P1D5

In one embodiment, a TCR of the present description comprises, or consists of, the alpha chain and/or beta chain of TCR R7P1D5, corresponding to SEQ ID NOs:55 and 63, respectively.

The TCR alpha variable domain of TCR R7P1D5 comprises, or alternatively consists of, amino acids 22 to 131 of SEQ ID NO:55; the TCR alpha constant domain of TCR R7P1D5 comprises, or alternatively consists of, amino acids 132 to 272 of SEQ ID NO:55; the TCR beta variable domain of TCR R7P1D5 comprises, or alternatively consists of, amino acids 20 to 131 of SEQ ID NO:63; and the TCR beta constant domain comprises, or alternatively consists of, amino acids 132 to 310 of SEQ ID NO:63.

In a particular embodiment, a TCR of the present description comprises a TCR alpha chain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha chain of SEQ ID NO:55.

In another embodiment, a TCR of the present description comprises a TCR alpha variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha variable domain of SEQ ID NO:55.

In an embodiment, a TCR of the present description comprises a TCR alpha constant domain at least 75%, 80%, 90%, 91%, 92%, 93%, 94%, 95%, 96%, 97%, 98%, or 99% identical, preferably 75% identical, to the TCR alpha constant domain of SEQ ID NO:55.

In an embodiment, a TCR of the present description comprises a TCR alpha variable domain comprising at least one alpha chain complementarity determining region (CDR) selected from the group consisting of the alpha chain CDR1, CDR2 and CDR3 of SEQ ID NO:55. In a preferred embodiment, the TCR alpha variable domain comprises the alpha chain CDR3 of SEQ ID NO:55. In another preferred embodiment, the TCR alpha variable domain comprises the alpha chain CDR1, CDR2 and CDR3 of SEQ ID NO:55.

In a particularly preferred embodiment, a TCR of the present description comprises a TCR alpha variable domain having at least 90% or 95% sequence identity to the TCR alpha variable domain of SEQ ID NO:55, and comprises the CDR1, CDR2 and CDR3 of SEQ ID NO:55.

In another particular embodiment, a TCR of the present description comprises a TCR beta chain at least 75%, 80%, 90%, 91%, 92%, 93%, 94%, 95%, 96%, 97%, 98%, or 99% identical, preferably 90% or 95% identical, to the TCR beta chain of SEQ ID NO:63.

In an embodiment, a TCR of the present description comprises a TCR beta variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR beta variable domain of SEQ ID NO:63.

In an embodiment, a TCR of the present description comprises a TCR beta constant domain at least 75%, 80%, 90%, 91%, 92%, 93%, 94%, 95%, 96%, 97%, 98%, or 99% identical, preferably 75% identical, to the TCR beta constant domain of SEQ ID NO:63.

In an embodiment, a TCR of the present description comprises a TCR beta variable domain comprising at least one beta chain complementarity determining region (CDR) selected from the group consisting of the beta chain CDR1, CDR2 and CDR3 of SEQ ID NO:63. In a preferred embodiment, the TCR beta variable domain comprises the beta chain CDR3 of SEQ ID NO:63. In another preferred embodiment, the TCR beta variable domain comprises the beta chain CDR1, CDR2 and CDR3 of SEQ ID NO:63.

In a particularly preferred embodiment, a TCR of the present description comprises a TCR beta variable domain having at least 90% or 95% sequence identity to the TCR beta variable domain of SEQ ID NO:63, and comprises CDR1, CDR2 and CDR3 of SEQ ID NO:63.

The alpha chain variable domain may comprise one or more alpha CDR domains having one, two, three or four amino acid substitutions relative to the corresponding CDR sequence of SEQ ID NO:55. Likewise, the beta chain variable domain may comprise one or more beta CDR domains having one, two, three or four amino acid substitutions relative to the corresponding beta CDR sequence of SEQ ID NO:63.

TCR R10P2G12

In one embodiment, a TCR of the present description comprises, or consists of, the alpha chain and/or beta chain of TCR R10P2G12, corresponding to SEQ ID NOs:71 and 79, respectively.

The TCR alpha variable domain of TCR R10P2G12 comprises, or alternatively consists of, amino acids 21 to 136 of SEQ ID NO:71; the TCR alpha constant domain of TCR R10P2G12 comprises, or alternatively consists of, amino acids 137 to 277 of SEQ ID NO:71; the TCR beta variable domain of TCR R10P2G12 comprises, or alternatively consists of, amino acids 20 to 134 of SEQ ID NO:79; and the TCR beta constant domain comprises, or alternatively consists of, amino acids 135 to 313 of SEQ ID NO:79.

In a particular embodiment, a TCR of the present description comprises a TCR alpha chain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha chain of SEQ ID NO:71.

In another embodiment, a TCR of the present description comprises a TCR alpha variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha variable domain of SEQ ID NO:71.

In an embodiment, a TCR of the present description comprises a TCR alpha constant domain at least 75%, 80%, 90%, 91%, 92%, 93%, 94%, 95%, 96%, 97%, 98%, or 99% identical, preferably 75% identical, to the TCR alpha constant domain of SEQ ID NO:71.

In an embodiment, a TCR of the present description comprises a TCR alpha variable domain comprising at least one alpha chain complementarity determining region (CDR) selected from the group consisting of the alpha chain CDR1, CDR2 and CDR3 of SEQ ID NO:71. In a preferred embodiment, the TCR alpha variable domain comprises the alpha chain CDR3 of SEQ ID NO:71. In another preferred embodiment, the TCR alpha variable domain comprises the alpha chain CDR1, CDR2 and CDR3 of SEQ ID NO:71.

In a particularly preferred embodiment, a TCR of the present description comprises a TCR alpha variable domain having at least 90% or 95% sequence identity to the TCR alpha variable domain of SEQ ID NO:71, and comprises the CDR1, CDR2 and CDR3 of SEQ ID NO:71.

In another particular embodiment, a TCR of the present description comprises a TCR beta chain at least 75%, 80%, 90%, 91%, 92%, 93%, 94%, 95%, 96%, 97%, 98%, or 99% identical, preferably 90%, 95%, 96%, 97%, 98%, or 99% identical, to the TCR beta chain of SEQ ID NO:79.

In an embodiment, a TCR of the present description comprises a TCR beta variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR beta variable domain of SEQ ID NO:79.

In an embodiment, a TCR of the present description comprises a TCR beta constant domain at least 75%, 80%, 90%, 91%, 92%, 93%, 94%, 95%, 96%, 97%, 98%, or 99% identical, preferably 75% identical, to the TCR beta constant domain of SEQ ID NO:79.

In an embodiment, a TCR of the present description comprises a TCR beta variable domain comprising at least one beta chain complementarity determining region (CDR) selected from the group consisting of the beta chain CDR1, CDR2 and CDR3 of SEQ ID NO:79. In a preferred embodiment, the TCR beta variable domain comprises the beta chain CDR3 of SEQ ID NO:79. In another preferred embodiment, the TCR beta variable domain comprises the beta chain CDR1, CDR2 and CDR3 of SEQ ID NO:79.

In a particularly preferred embodiment, a TCR of the present description comprises a TCR beta variable domain having at least 90% or 95% sequence identity to the TCR beta variable domain of SEQ ID NO:79, and comprises CDR1, CDR2 and CDR3 of SEQ ID NO:79.

The alpha chain variable domain may comprise one or more alpha CDR domains having one, two, three or four amino acid substitutions relative to the corresponding CDR sequence of SEQ ID NO:71. Likewise, the beta chain variable domain may comprise one or more beta CDR domains having one, two, three or four amino acid substitutions relative to the corresponding beta CDR sequence of SEQ ID NO:79.

In a further preferred embodiment, a TCR of the present description specifically binds to a MAG-003 peptide-HLA molecule complex, wherein the MAG-003 peptide is selected from KVLEHVVRV (SEQ ID NO:1) and variants thereof, such as those shown in SEQ ID NO:2 to SEQ ID NO:24. In an embodiment the HLA molecule is a class I MHC molecule selected from the group consisting of HLA-A, HLA-B, and HLA-C molecules. In one embodiment the HLA molecule is HLA-A*02. In another embodiment, the HLA molecule is a class II MHC molecule selected from the group consisting of HLA-DP, HLA-DQ, and HLA-DR.

TCRs of the present description preferably bind to a MAG-003 peptide-HLA molecule complex with a binding affinity ($K_D$) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Nonlimiting examples of preferred binding affinity ranges for TCRs of the present description include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity ($K_D$) for a MAG003 peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, a MAG-003 peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens (Aleksic et al. 2012; Kunert et al. 2013). It is now known, although tumor antigens have the potential to be immunogenic, because tumors arise from the individual's own cells only mutated proteins or proteins with altered translational processing will be seen as foreign by the immune system. Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance (Xing et al. 2012; Ruella et al. 2014; Sharpe et al. 2015), meaning that only T-cells with low-affinity TCRs for self-antigens remain. Therefore, affinity of TCRs or variants of the present description to MAG-003 have been enhanced by methods well known in the art as described below.

MAG-003 Peptides

The description provides a peptide comprising a sequence that is selected from the group of consisting of SEQ ID NO:1 to SEQ ID NO:24 or a variant thereof which is 88% homologous to SEQ ID NO:1 to SEQ ID NO:24, or a variant thereof that will induce T-cells cross-reacting with a peptide described herein. In an aspect, the peptides of the description have the ability to bind to a molecule of the human major histocompatibility complex (MHC) class-I or longer versions of a peptide described herein to class II. In an aspect, a TCR described herein is capable of binding to or specifically binding to a peptide described herein.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

Table 3: Expression frequencies F of HLA-A*02 and HLA-A*24 and the most frequent HLA-DR serotypes. Frequencies are deduced from haplotype frequencies Gf within the American population adapted from Mori et al. (Mori et al., 1997) employing the Hardy-Weinberg formula $F=1-(1-Gf)^2$. Combinations of A*02 or A*24 with certain HLA-DR alleles might be enriched or less frequent than expected from their single frequencies due to linkage disequilibrium. For details refer to Chanock et al. (Chanock et al., 2004).

TABLE 3

| Allele | Population | Calculated phenotype from allele frequency |
|---|---|---|
| A*02 | Caucasian (North America) | 49.1% |
| A*02 | African American (North America) | 34.1% |
| A*02 | Asian American (North America) | 43.2% |
| A*02 | Latin American (North American) | 48.3% |
| DR1 | Caucasian (North America) | 19.4% |
| DR2 | Caucasian (North America) | 28.2% |
| DR3 | Caucasian (North America) | 20.6% |
| DR4 | Caucasian (North America) | 30.7% |
| DR5 | Caucasian (North America) | 23.3% |
| DR6 | Caucasian (North America) | 26.7% |
| DR7 | Caucasian (North America) | 24.8% |
| DR8 | Caucasian (North America) | 5.7% |
| DR9 | Caucasian (North America) | 2.1% |
| DR1 | African (North) American | 13.20% |
| DR2 | African (North) American | 29.80% |
| DR3 | African (North) American | 24.80% |
| DR4 | African (North) American | 11.10% |
| DR5 | African (North) American | 31.10% |
| DR6 | African (North) American | 33.70% |
| DR7 | African (North) American | 19.20% |
| DR8 | African (North) American | 12.10% |
| DR9 | African (North) American | 5.80% |
| DR1 | Asian (North) American | 6.80% |
| DR2 | Asian (North) American | 33.80% |
| DR3 | Asian (North) American | 9.20% |
| DR4 | Asian (North) American | 28.60% |
| DR5 | Asian (North) American | 30.00% |
| DR6 | Asian (North) American | 25.10% |
| DR7 | Asian (North) American | 13.40% |
| DR8 | Asian (North) American | 12.70% |
| DR9 | Asian (North) American | 18.60% |
| DR1 | Latin (North) American | 15.30% |
| DR2 | Latin (North) American | 21.20% |
| DR3 | Latin (North) American | 15.20% |
| DR4 | Latin (North) American | 36.80% |
| DR5 | Latin (North) American | 20.00% |
| DR6 | Latin (North) American | 31.10% |
| DR7 | Latin (North) American | 20.20% |
| DR8 | Latin (North) American | 18.60% |
| DR9 | Latin (North) American | 2.10% |
| A*24 | Philippines | 65% |
| A*24 | Russia Nenets | 61% |
| A*24: 02 | Japan | 59% |
| A*24 | Malaysia | 58% |
| A*24: 02 | Philippines | 54% |
| A*24 | India | 47% |
| A*24 | South Korea | 40% |
| A*24 | Sri Lanka | 37% |
| A*24 | China | 32% |
| A*24: 02 | India | 29% |
| A*24 | Australia West | 22% |
| A*24 | USA | 22% |
| A*24 | Russia Samara | 20% |
| A*24 | South America | 20% |
| A*24 | Europe | 18% |

MAGEA4 Gene

This gene is a member of the MAGEA gene family. The members of this family encode proteins with 50 to 80% sequence identity to each other. The promoters and first exons of the MAGEA genes show considerable variability, suggesting that the existence of this gene family enables the same function to be expressed under different transcriptional controls. The MAGEA genes are clustered at chromosomal location Xq28. They have been implicated in some hereditary disorders, such as dyskeratosis congenita. At least four variants encoding the same protein have been found for this gene. (Provided by RefSeq, July 2008).

MAGEA4 localization has been described as cytoplasmic (Kim et al., 2015). However, MAGEA4 staining has also been detected in nuclei, with differential distribution between nucleus and cytoplasm in well-differentiated versus less differentiated cancers (Sarcevic et al., 2003).

MAGEA4 is used as a male germ cell marker. It is not expressed in gonocytes, but expressed in pre-spermatogonia and mature germ cells (Mitchell et al., 2014).

TABLE 4

| General cancer target | |
|---|---|
| Antigen properties | Evaluation |
| Over-expression in [cancer of interest] reported in literature | |
| Over-expression in other cancers reported in literature | + |
| T-cell responses against source protein-derived targets described | + |
| Oncofetal expression pattern | + |
| Expression by cancer stem cells | (−) |
| Roles in cell cycle progression and tumor cell proliferation | (−) |
| Involvement in tumor invasion, migration and metastasis | |
| Link to cancer-associated signaling pathways[1] | |
| Anti-apoptotic effects | (−) |
| Pro-angiogenic effects/Neovascularisation | |
| Over-expression linked to poor prognosis in cancer | + |
| Over-expression associated with advanced cancer stages | + |
| General cancer target | |
| Sub-cellular localization[2] | CY |
| Characterization of source protein in literature (−, +, ++, +++) | + |
| Cell type association[3] | TU |

[1]TGF = Transforming growth factor;
PI3K = Phosphatidylinositide 3-kinases;
p53 = cellular tumor antigen p53;
EGFR = epithelial growth factor receptor;
FGF2 = fibroblast growth factor 2;
Wnt = Wnt/beta-catenin pathway (embryogenesis);
Ras = Rat sarcoma proto-oncogene;
NF-kB = Nuclear factor Kappa B (eukaryotic transcription factor)
[2]CY = cytoplasmic;
[3]TU = tumor cells pMHC as Target A phase I clinical trial investigated adoptive transfer of TCR-engineered autologous CTLs reactive towards MAGEA4(143-151) bound to HLA-A*24:02 in esophageal cancer patients. Patients were given TCR-transduced lymphocytes once, without preconditioning treatment, followed by subcutaneous immunizations with MAGEA4 peptide after 2 and 4 weeks. No objective tumor regression was observed, possibly due to the lack of lymphodepleting regimen and administration of IL2 (Kageyama et al., 2015). Preclinical studies in mice had demonstrated that transferred T-cells inhibited growth of MAGEA4-expressing tumor cell lines inoculated in the mice, and that additional peptide vaccination enhanced this antitumor activity (Shirakura et al., 2012).

Targeting MAGEA4 with adoptive CTL transfer is proposed as a treatment option of EBV-negative Hodgkin and non-Hodgkin lymphoma. Infused CTLs targeting EBV-derived peptides have been described to induce complete remissions in EBV(+) lymphoma patients. Therefore, targeting other antigens expressed by lymphoma, including MAGEA4, is being explored as a possible treatment option (Cruz et al., 2011; Gerdemann et al., 2011).

Several studies have demonstrated the generation of MAGEA4 specific CD4(+) T-cells from healthy donors and cancer patients after incubation with autologous antigen-presenting cells pulsed with overlapping peptide pools (Cesson et al., 2011; Gerdemann et al., 2011; Ohkuri et al., 2009).

MAG-003 peptide, i.e., KVLEHVVRV (SEQ ID NO:1), is a HLA-A*0201-restricted cytotoxic T lymphocyte (CTL) epitope of MAGEA4 (amino acids 286-294). (Jia et al. 2010; Wu et al. 2011), the contents of which are hereby incorporated by reference in their entirety. In an aspect, MAG-003 elicits peptide-specific CTLs both in vitro from HLA-A*0201-positive PBMCs and in HLA-A*0201/Kb transgenic mice. In another aspect, the induced CTLs lyse target-cells in an HLA-A*0201-restricted fashion, demonstrating that MAG-003 is HLAA*0201-restricted CTL epitope and serve as a target for therapeutic antitumoral vaccination (Jia et al. 2010), the content of which is hereby incorporated by reference in its entirety.

FIG. 1 shows MAG-003 peptide presentation in healthy tissues and cancers. The results are summarized in Table 5. Specifically, about 4,000 and 2,000 copies of MAG-003 per cell are estimated in tumor tissues from ovarian cancer (OC) and non-small cell lung cancer (NSCLC), respectively.

TABLE 5

MAG-003 presentation in healthy tissues and cancers.

| A*02 | Samples | Mean intensity | jScore |
|---|---|---|---|
| Healthy | 0 of 245 | — | — |
| Cancer | 14 of 397 | 1.1e+07 | 0.000 |
| HCC | 1 of 16 | 2.9e+06 | 0.000 |
| MEL | 0 of 3 | 0.0e+00 | |
| OC | 2 of 20 | 4.0e+07 | 0.000 |
| pNSCLC | 11 of 91 | 1.0e+07 | 0.000 |

Expression Profiling of Genes Encoding the Peptides of the Description

Over-presentation or specific presentation of TAAs on tumor cells compared to healthy cells is sufficient for its usefulness in immunotherapy, and some peptides are tumor-specific despite their source protein occurring also in healthy tissues. Still, mRNA expression profiling adds an additional level of safety in selection of peptide targets for immunotherapies. Especially for therapeutic options with high safety risks, such as affinity-matured TCRs, the ideal target peptide will be derived from a protein that is unique to the tumor and not found on healthy tissues.

RNA Sources and Preparation

Surgically removed tissue specimens were provided as indicated above after written informed consent had been obtained from each patient. Tumor tissue specimens were snap-frozen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

RNAseq Experiments

Gene expression analysis of tumor and healthy tissue RNA samples was performed by next generation sequencing (RNAseq) by CeGaT (Tübingen, Germany). Sequencing libraries are prepared using the Illumina HiSeq v4 reagent kit according to the provider's protocol (Illumina Inc, San Diego, Calif., USA), which includes RNA fragmentation, cDNA conversion and addition of sequencing adaptors. Libraries derived from multiple samples are mixed equimolarly and sequenced on the Illumina HiSeq 2500 sequencer according to the manufacturer's instructions, generating 50 bp single end reads. Processed reads are mapped to the human genome (GRCh38) using the STAR software. Expression data are provided on transcript level as RPKM (Reads Per Kilobase per Million mapped reads, generated by the software Cufflinks) and on exon level (total reads, generated by the software Bedtools), based on annotations of the ensembl sequence database (Ensembl77). Exon reads are normalized for exon length and alignment size to obtain RPKM values.

Figure 2:
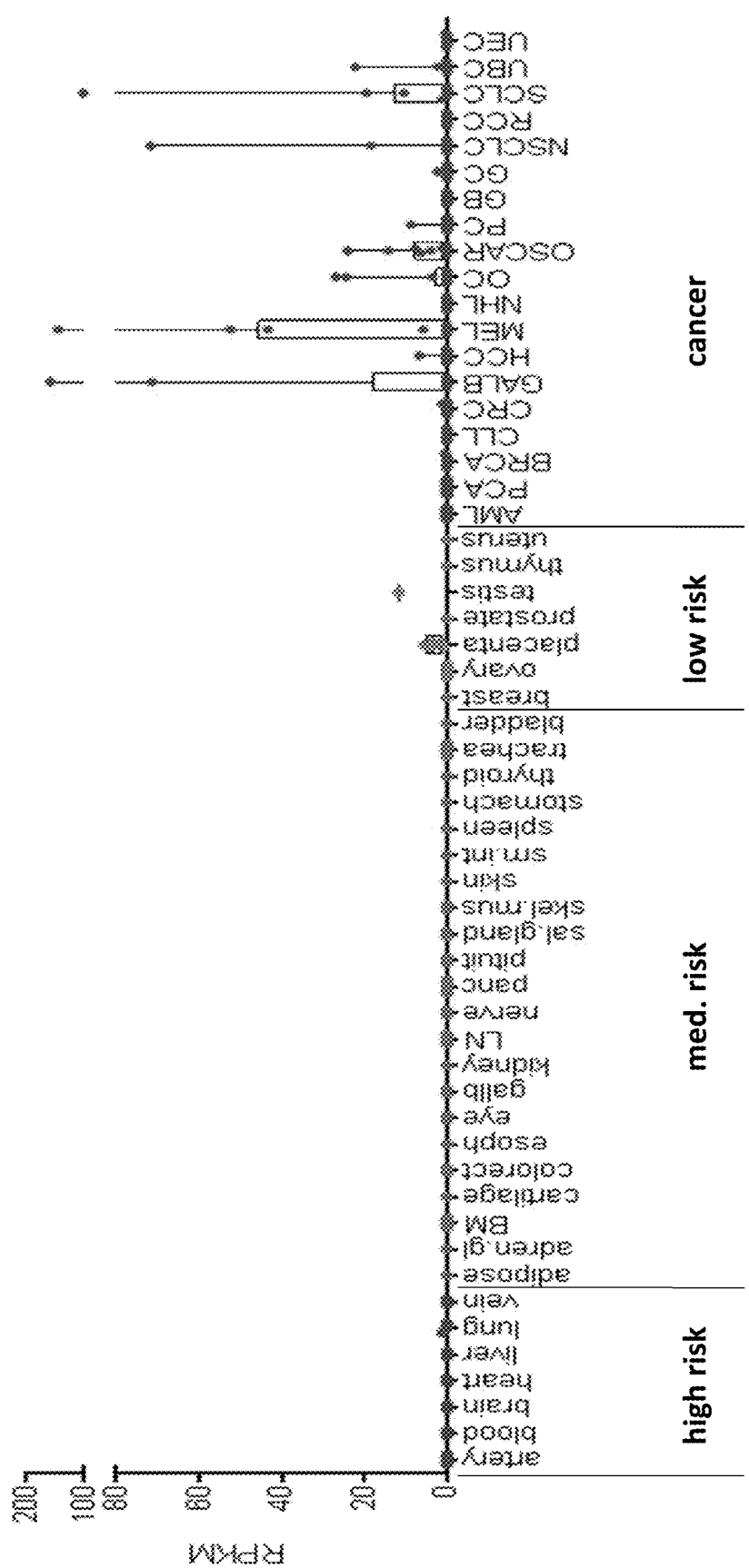
FIG. 2 shows MAG-003 expression in cancer and healthy tissues.
Figure 3:
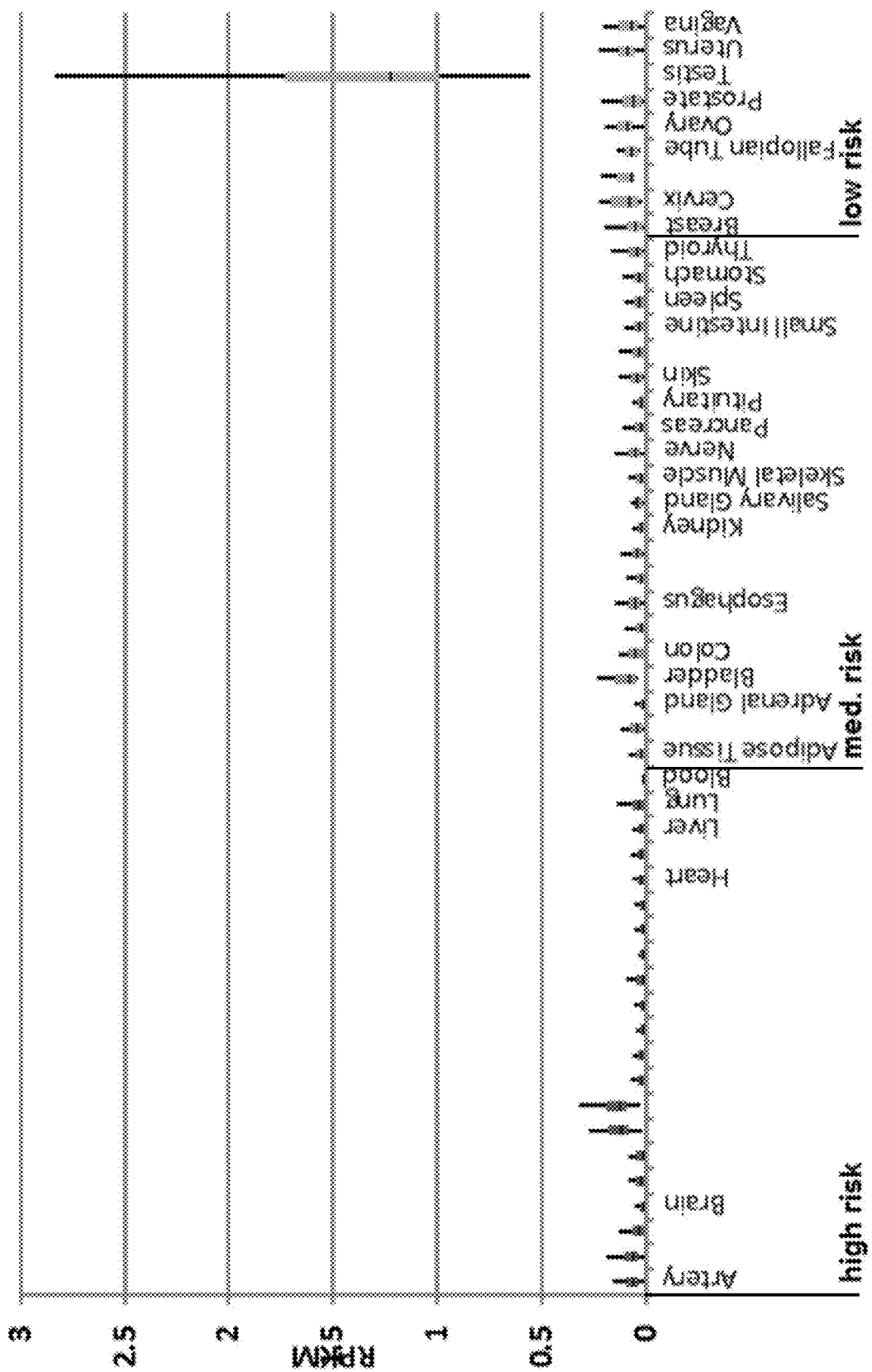
FIG. 3 shows MAG-003 expression in cancer and healthy tissues.
Figure 4:
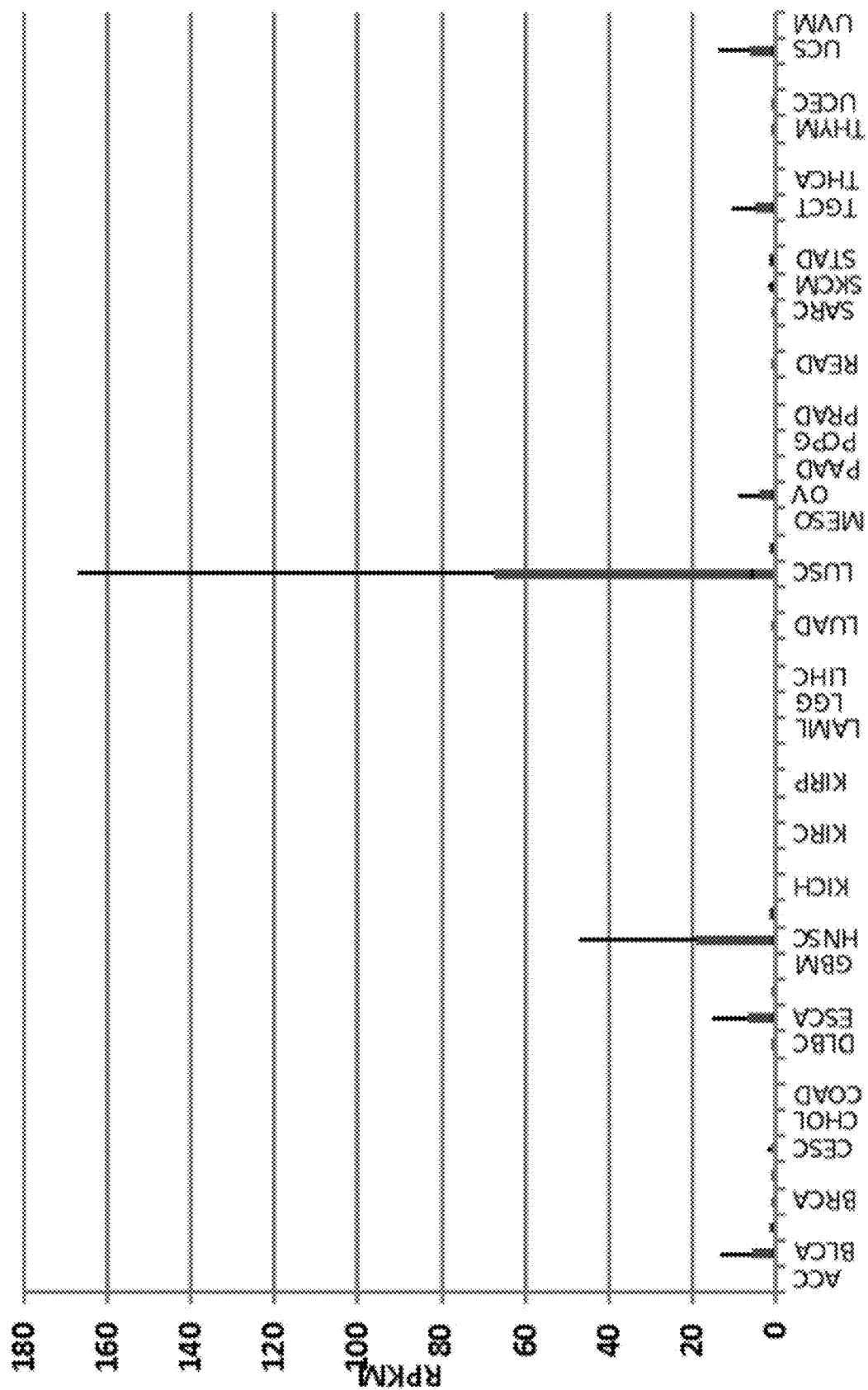
FIG. 4 shows MAG-003 expression in cancer and healthy tissues.

As shown in FIGS. 2-4, MAG-003 is highly expressed in cancer tissues and in low risk healthy tissues, such as testis, as compared with that is high risk and medium risk healthy tissues.

Tables 6-8 show RNASeq data (expression scores) of MAG-003 expression in various cancers

TABLE 6

RNASeq Score 1

| Tumor type | tgScore | exonScore (27242) | exonScore (317034) | exonScore (593984) |
|---|---|---|---|---|
| BRCA | 1.57 | 1.23 | 1.23 | 1.51 |
| CRC | 1.65 | 1.00 | 1.00 | 1.76 |
| HCC | 12.10 | 11.98 | 11.97 | 6.15 |
| OC | 56.60 | 18.45 | 18.44 | 57.74 |
| OSCAR | 58.42 | 3.49 | 3.49 | 60.40 |
| PC | 12.10 | 10.78 | 10.77 | 4.74 |
| pGB | 0.88 | 0.95 | 0.95 | 0.74 |
| pNSCLC | 100.83 | 1.52 | 1.52 | 98.57 |
| RCC | 0.93 | 0.95 | 0.95 | 0.77 |
| SCLC | 56.41 | 28.32 | 28.30 | 152.27 |

TABLE 7

RNASeq Score 3

| Tumor type | tgScore | exonScore (27242) | exonScore (317034) | exonScore (593984) |
|---|---|---|---|---|
| BRCA | 7.48 | 5.11 | 5.11 | 6.01 |
| CRC | 8.35 | 1.05 | 1.05 | 7.90 |
| HCC | 123.03 | 210.33 | 210.30 | 42.22 |
| OC | 612.59 | 333.74 | 333.69 | 447.29 |
| OSCAR | 632.95 | 47.41 | 47.40 | 468.45 |
| PC | 122.95 | 187.07 | 187.05 | 31.15 |
| pGB | 0.31 | 0.18 | 0.18 | 0.25 |
| pNSCLC | 1100.05 | 10.26 | 10.25 | 768.23 |
| RCC | 0.78 | 0.18 | 0.18 | 0.43 |
| SCLC | 611.00 | 524.23 | 524.17 | 1190.36 |

TABLE 8

Tumor expression

| Tumor type | tgtumor40 | Exontumor40 (27242) | Exontumor40 (317034) | Exontumor40 (593984) |
|---|---|---|---|---|
| BRCA | 0.12 | 0.04 | 0.04 | 0.17 |
| CRC | 0.14 | 0.01 | 0.01 | 0.22 |
| HCC | 2.05 | 1.82 | 1.82 | 1.18 |
| OC | 11.19 | 3.16 | 3.16 | 13.72 |
| OSCAR | 10.89 | 0.42 | 0.42 | 13.11 |
| PC | 2.09 | 1.65 | 1.65 | 0.89 |
| pGB | 0.00 | 0.00 | 0.00 | 0.01 |
| pNSCLC | 19.25 | 0.09 | 0.09 | 22.58 |
| RCC | 0.01 | 0.00 | 0.00 | 0.01 |
| SCLC | 10.18 | 4.53 | 4.53 | 33.35 |

In an aspect, a peptide consisting essentially of the amino acid sequence as indicated herein can have one or two non-anchor amino acids (see below regarding the anchor motif) exchanged without that the ability to bind to a molecule of the human major histocompatibility complex (MHC) class-I or —II is substantially changed or is negatively affected, when compared to the non-modified peptide. In another embodiment, in a peptide consisting essentially of the amino acid sequence as indicated herein, one or two amino acids can be exchanged with their conservative exchange partners (see herein below) without that the ability to bind to a molecule of the human major histocompatibility complex (MHC) class-I or —II is substantially changed, or is negatively affected, when compared to the non-modified peptide.

The amino acid residues that do not substantially contribute to interactions with the TCR can be modified by replacement with other amino acids whose incorporation do not substantially affect T-cell reactivity and does not eliminate binding to the relevant MHC. Thus, apart from the proviso given, the peptide of the description may be any peptide (by which term the inventors include oligopeptide or polypeptide), which includes the amino acid sequences or a portion or variant thereof as given.

TABLE 9

Variants and motif of the peptides

| Position | 1 | 2 | 3 | 4 | 5 | 6 | 7 | 8 | 9 |
|---|---|---|---|---|---|---|---|---|---|
| SEQ ID NOs:1-24 | K | V | L | E | H | V | V | R | V |
| Variants |   |   |   |   |   |   |   |   | L |
|   |   |   |   |   |   |   |   |   | A |
|   |   |   |   |   |   |   |   |   | I |
|   |   |   | L |   |   |   |   |   |   |
|   |   |   | L |   |   |   |   |   | L |
|   |   |   | L |   |   |   |   |   | A |
|   |   |   | L |   |   |   |   |   | I |
|   |   |   | A |   |   |   |   |   |   |
|   |   |   | A |   |   |   |   |   | L |
|   |   |   | A |   |   |   |   |   | A |
|   |   |   | A |   |   |   |   |   | I |
|   | Y |   | L |   |   |   |   |   |   |
|   | Y |   | L |   |   |   |   |   | L |
|   | Y |   | L |   |   |   |   |   | A |
|   | Y |   | L |   |   |   |   |   | I |
|   | Y |   | A |   |   |   |   |   |   |
|   | Y |   | A |   |   |   |   |   | L |
|   | Y |   | A |   |   |   |   |   | A |
|   | Y |   | A |   |   |   |   |   | I |
|   | Y |   |   |   |   |   |   |   |   |
|   | Y |   |   |   |   |   |   |   | L |
|   | Y |   |   |   |   |   |   |   | A |
|   | Y |   |   |   |   |   |   |   | I |

Longer peptides may also be suitable in an aspect. It is possible that MHC class I epitopes, although usually the actual epitope are residues that do not substantially affect proteolytic cleavage necessary to expose the actual epitope during processing.

In an aspect, peptides of the description can be elongated by up to 1, 2, 3, or 4 amino acids, that is 1, 2, 3 or 4 amino acids can be added to either end of the peptide in any combination between 8 and 11 amino acids long. It is preferred that the residues that flank between 4:0 and 0:4. Combinations of the elongations according to the description can be found in Table 10.

TABLE 10

Combinations of the elongations of peptides of the description

| C-terminus | N-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

| N-terminus | C-terminus |
|---|---|
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation/extension can be the peptides of the original sequence of the protein or any other amino acid(s). The elongation can be used to enhance the stability or solubility of the peptides.

Thus, the epitopes of the present description may be identical to naturally occurring tumor-associated or tumor-specific epitopes or may include epitopes that differ by no more than four residues from the reference peptide, as long as they have substantially identical antigenic activity.

In an alternative embodiment, the peptide is elongated on either or both sides by more than 4 amino acids, preferably to a total length of up to 30 amino acids. In an aspect, this elongation leads to MHC class II binding peptides. Binding to MHC class II can be tested by methods known in the art.

Accordingly, the present description provides peptides and variants of MHC class I epitopes, wherein the peptide or variant has an overall length of between 8 and 100, preferably between 8 and 30, and most preferred between 8 and 14, namely 8, 9, 10, 11, 12, 13, 14 amino acids, in case of the longer class II binding peptides the length can also be 15, 16, 17, 18, 19, 20, 21 or 22 amino acids.

In an aspect, the peptide or variant according to the present description will have the ability to bind to a molecule of the human major histocompatibility complex (MHC) class I or II. Binding of a peptide or a variant to a MHC complex may be tested by methods known in the art.

Preferably, when the T-cells specific for a peptide according to the present description are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 pM. It is also preferred that the substituted peptide be recognized by T-cells from more than one individual, at least two, and more preferably three individuals.

As used herein, the term "complex" refers to a molecule that specifically binds to an (e.g., antigenic) determinant. In one embodiment, a complex is able to direct the entity to which it is attached (e.g., a (second) antigen binding moiety) to a target site, for example to a specific type of tumor cell or tumor stroma bearing the antigenic determinant (e.g., the complex of a peptide with MHC, according to the application at hand). In another embodiment a complex is able to activate signaling through its target antigen, for example a T-cell receptor complex antigen. Complexes include but are not limited to antibodies and fragments thereof, antigen binding domains of an antibody, comprising an antibody heavy chain variable region and an antibody light chain variable region, binding proteins comprising at least one ankyrin repeat motif and single domain antigen binding (SDAB) molecules, aptamers, (soluble) TCRs and (modified) cells such as allogenic or autologous T-cells. To assess whether a molecule is a complex binding to a target, binding assays can be performed.

"Specific" binding means that the complex (e.g. TCR) binds the peptide-MHC-complex of interest better than other naturally occurring peptide-MHC-complexes, to an extent that a complex armed with an active molecule that is able to kill a cell bearing the specific target is not able to kill another cell without the specific target but presenting other peptide-MHC complex(es). Binding to other peptide-MHC complexes is irrelevant if the peptide of the cross-reactive peptide-MHC is not naturally occurring, i.e., not derived from the human HLApeptidome. Tests to assess target-cell killing are well known in the art. They should be performed using target-cells (primary cells or cell lines) with unaltered peptide-MHC presentation, or cells loaded with peptides such that naturally occurring peptide-MHC levels are reached.

Each complex can comprise a labelling which provides that the bound complex can be detected by determining the presence or absence of a signal provided by the label. For example, the complex can be labeled with a fluorescent dye or any other applicable cellular marker molecule. Such marker molecules are well known in the art. For example a fluorescence-labelling, for example provided by a fluorescence dye, can provide a visualization of the bound aptamer by fluorescence or laser scanning microscopy or flow cytometry.

Each complex can be conjugated with a second active molecule such as for example IL-21, anti-CD3, and anti-CD28.

Further information on polypeptide complexes may be found, for example, in the background section of WO 2014/071978A1, which is incorporated by reference in its entirety.

A "pharmaceutical composition" is a composition suitable for administration to a human being in a medical setting. Preferably, a pharmaceutical composition is sterile and produced according to GMP guidelines.

Pharmaceutical compositions of the present description also include at least one TCR, soluble TCR, nucleic acid, and/or host cell expressing a TCR of the present description, in a pharmaceutically acceptable carrier.

Pharmaceutical compositions of the present description may also include pharmaceutically acceptable excipients and/or stabilizers.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomateous or cancerous diseases. Exemplary formulations can be found in, for example, EP2112253, which is herein incorporated by reference in its entirety.

A further aspect of the description provides nucleic acids (for example polynucleotides) encoding a peptide, peptide variants, TCRs and TCR variants of the description. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the description provides an expression vector capable of expressing a polypeptide according to the description.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the description employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

TCR chains introduced into a peripheral T-cell may compete with endogenous TCR chains for association with the CD3 complex, which is necessary for TCR surface expression. Because a high level of TCR surface expression is essential to confer appropriate sensitivity for triggering by cells expressing the target tumor antigen (Cooper et al., 2000; Labrecque et al., 2001), strategies that enhance TCR-alpha and TCR-beta gene expression levels are an important consideration in TCR gene therapy.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter (Cooper et al., 2004; Jones et al., 2009), elongation factor (EF)-1a (Tsuji et al., 2005) and the spleen focus-forming virus (SFFV) promoter (Joseph et al., 2008). In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bicistronic constructs in a single vector, which has been shown to be capable of overcoming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

The DNA (or in the case of retroviral vectors, RNA) may then be expressed in a suitable host to produce a polypeptide comprising the peptide or variant of the description. Thus, the DNA encoding the peptide or variant of the description may be used in accordance with known techniques, appropriately modified in view of the teachings contained herein, to construct an expression vector, which is then used to transform an appropriate host cell for the expression and production of the polypeptide of the description. Such techniques include those disclosed, for example, in U.S. Pat. Nos. 4,440,859, 4,530,901, 4,582,800, 4,677,063, 4,678,751, 4,704,362, 4,710,463, 4,757,006, 4,766,075, and 4,810,648, which are herein incorporated by reference in their entirety.

The DNA (or in the case of retroviral vectors, RNA) encoding the polypeptide constituting the compound of the description may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the description are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant-cells, animal cells and insect-cells. Preferably, the system can be mammalian cells such as CHO cells available from the ATCC Cell Biology Collection.

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent-cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the description are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present description also relates to a host cell transformed with a polynucleotide vector construct of the present description. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect-cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present description is accomplished by well-known methods that typically depend on the type of vector used. With regard to transformation of prokaryotic host cells, see, for example, Cohen et al. (Cohen et al., 1972) and (Green and Sambrook, 2012). Transformation of yeast-cells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast-cell, bacterial cells, insect-cells and vertebrate cells.

Successfully transformed cells, i.e., cells that contain a DNA construct of the present description, can be identified by well-known techniques such as PCR. Alternatively, the presence of the protein in the supernatant can be detected using antibodies.

It will be appreciated that certain host cells of the description are useful in the preparation of the peptides of the description, for example bacterial, yeast and insect-cells. However, other host cells may be useful in certain therapeutic methods. For example, antigen-presenting cells, such as dendritic cells, may usefully be used to express the peptides of the description such that they may be loaded into appropriate MHC molecules. Thus, the current description provides a host cell comprising a nucleic acid or an expression vector according to the description.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the description provides a method of producing a peptide or its variant, the method comprising culturing a host cell and isolating the peptide from the host cell or its culture medium.

In another embodiment the TCRs, the nucleic acid or the expression vector of the description are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g., between 50 μg and 1.5 mg, preferably 125 μg to 500 μg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g., Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Nonviral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T-cells for the respective opposite CDR as noted above.

The present description further relates to aptamers. Aptamers (see for example WO 2014/191359 and the literature as cited therein which are herein incorporated by reference in their entirety) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. In an aspect, at least one or more aptamers are taken up by tumor cells and thus can function as molecular vehicles for the targeted delivery of anti-cancer agents such as siRNA into tumor cells.

Aptamers can be selected against complex targets such as cells and tissues and complexes of the peptides or the TCRs comprising, preferably consisting of, a sequence according to any of SEQ ID NO 25 to SEQ ID NO 26, according to the description at hand with the MHC molecule, using the cell-SELEX (Systematic Evolution of Ligands by Exponential enrichment) technique.

In one embodiment the description provides a method of producing a TCR as described herein, the method comprising culturing a host cell capable of expressing the TCR under conditions suitable to promote expression of the TCR.

The present description further relates to a method of identifying and isolating a TCR according to the present description, said method comprising incubating PBMCs from HLA-A*02-negative healthy donors with A2/MAG-003 monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising incubating PBMCs from HLA-A*02-negative healthy donors with A2/p286-1Y2L monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising incubating PBMCs from HLA-A*02-negative healthy donors with A2/p286-1Y2L9L monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with MAG-003, incubating PBMCs obtained from the transgenic mice with tetramer-phycoerythrin (PE), and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L, incubating PBMCs obtained from the transgenic mice with tetramer-phycoerythrin (PE), and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L9L, incubating PBMCs obtained from the transgenic mice with tetramer-phycoerythrin (PE), and isolating the high avidity T-cells by fluorescence activated cell sorting (FACS)-Calibur analysis.

The present description further relates to the method according to the description, wherein the T-cell comprises an expression vector capable of expressing A TCR according to the present description.

The present description further relates to a method of killing target-cells in a patient which target-cells aberrantly express MAG-003, the method comprising administering to the patient an effective number of TCRs, soluble TCRs and/or T-cells as according to the present description.

The present description further relates to the use of any TCR described, a nucleic acid according to the present description, an expression vector according to the present description, a cell according to the present description, or an activated cytotoxic T lymphocyte according to the present description as a medicament or in the manufacture of a medicament. The present description further relates to a use according to the present description, wherein the medicament is active against cancer.

The present description further relates to a use according to the description, wherein said cancer cells are non-small cell lung cancer cells or other solid or haematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

The present description further relates to a method of killing cancer cells comprising contact the cancer cells with a host cell of the present description. In one embodiment, the host cell expresses a TCR of the present description. In one embodiment the host cell is a T-cell or T-cell progenitor. In one embodiment, In a preferred embodiment the cancer cells are selected from non-small cell lung cancer cells or other solid or haematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer. In some embodiments, the TCR is conjugated to a therapeutically active agent. In certain embodiments the therapeutically active agent is selected from the group consisting of a radionuclide, a chemotherapeutic agent, and a toxin.

The present invention further relates to a method of treating cancer comprising administering to a subject in need thereof a host cell of the present invention. In one embodiment, the host cell expresses a TCR of the present description. In one embodiment the host cell is a T-cell or T-cell progenitor. In one embodiment the host cell is autologous to the subject to be treated. In another embodiment the host cell is allogeneic to the subject to be treated. In a preferred embodiment the cancer cells are selected from non-small cell lung cancer cells or other solid or haematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

In some embodiments, the TCR is conjugated to a therapeutically active agent. As used herein, the term "therapeutically active agent" means a compound used to treat or prevent a disease or undesirable medical condition. In one embodiment, the therapeutically active agent is used to treat or prevent cancer. In certain embodiments the therapeutically active agent is selected from the group consisting of a radionuclide, a chemotherapeutic agent, and a toxin.

TCRs, nucleic acids and host cells of the present description, and pharmaceutical compositions thereof, may be administered to a subject in need thereof by routes known in the art, and may vary depending on the type of cancer to be treated. Routes of administration include, for example, local administration (such as intratumoral) and parenteral administration such as subcutaneous, intraperitoneal, intramuscular, intravenous, intraportal and intrahepatic. In a preferred embodiment, TCRs, nucleic acids or host cells of the present description, or pharmaceutical compositions thereof, are administered to a subject by local infusion, for example using an infusion pump and/or catheter system, to a site to be treated, such as a solid tumor. In one embodiment, a composition of the present description is infused into a solid tumor, a blood vessel that feeds a solid tumor, and/or the area surrounding a solid tumor.

In preferred embodiments, compositions of the present description are administered to a subject using a dosing regimen of at least two administrations separated by at least 24 hours. Dosing regimens suitable for administering compositions of the present description include, for example, once a day, once every two days, and once every three days. More preferred dosing regimens include once a week, twice a week, once every other week, once a month, and twice a month. In particular embodiments, a dose escalation regimen is used, wherein a series of increasing doses is administered to a subject over a period of days, weeks or months.

Effective doses of host cells expressing TCRs of the present invention include, for example at least about $10^4$, at least about $10^5$, at least about $10^6$, at least about $10^7$, at least about $10^8$, at least about $10^9$, and at least $10^{10}$ host cells per dose. In one embodiment, host cells of the present description are administered in a dose of between about $10^4$ to about $10^{10}$ cells per dose, preferably in a dose of between about $10^5$ to about $10^9$ cells per dose. In preferred embodiments, doses are administered in a dosing regimen over the course of at least two or more dosing cycles.

The present invention also relates to a method of treating cancer comprising administering a TCR, a nucleic acid, or a host cell of the present description in combination with at least one chemotherapeutic agent and/or radiation therapy.

Also provided is a method of treating cancer in a subject in need thereof, comprising:
a) isolating a cell from said subject;
b) transforming the cell with at least one vector encoding a TCR of the present description to produce a transformed cell;
c) expanding the transformed cell to produce a plurality of transformed cells; and
d) administering the plurality of transformed cells to said subject.

Also provided is a method of treating cancer in a subject in need thereof, comprising:
a) isolating a cell from a healthy donor;
b) transforming the cell with a vector encoding a TCR of the present description to produce a transformed cell;
c) expanding the transformed cell to produce a plurality of transformed cells; and
d) administering the plurality of transformed cells to said subject.

Also provided is a method of detecting cancer in a biological sample comprising:
a) contacting the biological sample with a TCR of the present description;
b) detecting binding of the TCR to the biological sample.

In some embodiments the method of detecting cancer is carried out in vitro, in vivo or in situ.

The present description further relates to particular marker proteins and biomarkers based on the peptides according to the present description, herein called "targets" that can be used in the diagnosis and/or prognosis of non-small cell lung cancer. The present description also relates to the use of these novel targets for cancer treatment.

It is a further aspect of the description to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g., by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), domains recruiting effector cells such as an anti-CD3 domain, etc., in order to execute particular functions on target-cells. In another aspect, it is expressed in T-cells used for adoptive transfer. See, for example, WO 2004/033685A1, WO 2004/

074322A1, and WO 2013/057586A1, the contents of which are incorporated by reference in their entirety.

In addition, the peptides and/or the TCRs or antibodies or other binding molecules of the present description can be used to verify a pathologist's diagnosis of a cancer based on a biopsied sample.

The antibodies or TCRs may also be used for in vivo diagnostic assays. Generally, the antibody or TCR is labeled with a radionucleotide (such as $^{111}$In, $^{99}$Tc, $^{14}$C, $^{131}$I, $^{3}$H, $^{32}$P or $^{35}$S)) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies or TCRs for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies and/or TCRs may be directly or indirectly labeled with said probes. Attachment of probes to the antibodies and/or TCRs includes covalent attachment of the probe, incorporation of the probe into the antibody or TCR, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

The invention further pertains to the following items:

Item 1. A TCR comprising an alpha chain and a beta chain, wherein the alpha chain comprises a TCR alpha variable domain at least 90% identical to the amino acid sequence of any of SEQ ID NO:39, SEQ ID NO:55 and SEQ ID NO:71; and the beta chain comprises a TCR beta variable domain at least 90% identical to any of SEQ ID NO:47, SEQ ID NO:63 and SEQ ID NO:79, and wherein the TCR specifically binds to a MAG-003 peptide-MHC molecule complex.

Item 2. The TCR of item 1, further comprising a TCR alpha constant domain and a TCR beta constant domain, wherein the TCR alpha constant domain is at least 70% identical to a TCR alpha constant domain of any of SEQ ID NO:39, SEQ ID NO:55 and SEQ ID NO:71, and the beta constant domain is at least 70% identical to a TCR beta constant domain of any of SEQ ID NO:47, SEQ ID NO:63 and SEQ ID NO:79.

Item 3. The TCR of any of items 1 or 2, wherein the alpha constant domain comprises the alpha transmembrane domain VIGFRILLLKVAGFNLLMTL (SEQ ID NO:97) and the beta constant domain comprises the beta transmembrane domain TILYEILLGKATLYAVLVSALVL (SEQ ID NO:88).

Item 4. The TCR of any of items 1 to 3, wherein the TCR alpha variable domain consists of the amino acid sequence of SEQ ID NO:39; and the TCR beta variable domain consists of the amino acid sequence of SEQ ID NO:47.

Item 5. The TCR of any of items 1 to 3, wherein the TCR alpha variable domain consists of the amino acid sequence of SEQ ID NO:55; and the TCR beta variable domain consists of the amino acid sequence of SEQ ID NO:63.

Item 6. The TCR of any of items 1 to 3, wherein the TCR alpha variable domain consists of the amino acid sequence of SEQ ID NO:71; and the TCR beta variable domain consists of the amino acid sequence of SEQ ID NO:79.

Item 7. The TCR of any of items 1 to 6, wherein the TCR alpha constant domain consists of the TCR alpha constant domain of SEQ ID NO:39, and the TCR beta constant domain consists of the TCR beta constant domain of SEQ ID NO:47.

Item 8. The TCR of any of items 1 to 6, wherein the TCR alpha constant domain consists of the TCR alpha constant domain of SEQ ID NO:55, and the TCR beta constant domain consists of the TCR beta constant domain of SEQ ID NO:63.

Item 9. The TCR of any of items 1 to 6, wherein the TCR alpha constant domain consists of the TCR alpha constant domain of SEQ ID NO:71, and the TCR beta constant domain consists of the TCR beta constant domain of SEQ ID NO:79.

Item 10. The TCR of any of items 1 to 9, comprising an alpha chain consisting of SEQ ID NO:39 and a beta chain consisting of SEQ ID NO:47.

Item 11. The TCR of any of items 1 to 9, comprising an alpha chain consisting of SEQ ID NO:55 and a beta chain consisting of SEQ ID NO:63.

Item 12. The TCR of any of items 1 to 9, comprising an alpha chain consisting of SEQ ID NO:71 and a beta chain consisting of SEQ ID NO:79.

Item 13. The TCR of any of items 1 to 12, wherein the TCR alpha chain comprises at least one alpha chain complementarity determining region (CDR) selected from the group consisting of an alpha chain CDR1, CDR2 and CDR3 of SEQ ID NO:39, SEQ ID NO:55 and SEQ ID NO:71; and/or the TCR beta chain comprises at least one beta chain complementarity determining region (CDR) selected from the group consisting of a beta chain CDR1, CDR2 and CDR3 of SEQ ID NO:47, SEQ ID NO:63 and SEQ ID NO:79.

Item 14. The TCR of any of items 1 to 13, wherein the TCR alpha chain comprises all three CDRs of SEQ ID NO:39, SEQ ID NO:55 or SEQ ID NO:71.

Item 15. The TCR of any of items 1 to 13, wherein the TCR beta chain comprises all three CDRs of SEQ ID NO:47, SEQ ID NO:63 or SEQ ID NO:79.

Item 16. The TCR of any of items 1 to 15, wherein the alpha chain and beta chain are fused to form a single chain TCR.

Item 17. The TCR of any of items 1 to 16, wherein the alpha and/or beta chain comprises a detectable label.

Item 18. The TCR of item 17, wherein the detectable label is selected from the group consisting of a radionuclide, a fluorophore and biotin.

Item 19. The TCR of any of items 1 to 18, wherein the alpha and/or beta chain is conjugated to a therapeutically active agent.

Item 20. The TCR of item 19, wherein the therapeutically active agent is selected from the group consisting of a radionuclide, a chemotherapeutic agent and a toxin.

Item 21. A TCR comprising a gamma chain and a delta chain, wherein the gamma chain comprises at least one complementarity determining region (CDR) selected from the group consisting of an alpha chain CDR1, CDR2 and CDR3 of SEQ ID NO:39, SEQ ID NO:55 and SEQ ID NO:71; and/or the TCR delta chain comprises at least one complementarity determining region (CDR) selected from the group consisting of a beta chain CDR1, CDR2 and CDR3 of SEQ ID NO:47, SEQ ID NO:63 and SEQ ID NO:79, and wherein the TCR specifically binds to a MAG-003 peptide-MHC molecule complex.

Item 22. The TCR of any of items 1 to 21, wherein the TCR specifically binds to a MAG003 peptide-MHC molecule complex, wherein the MAG-003 peptide is selected from the group consisting of SEQ ID NOs:1-24, and the MHC molecule is an HLA class I or HLA class II molecule.

Item 23. A nucleic acid encoding the alpha chain and/or beta chain of the TCR of any of items 1 to 20, or the gamma chain and/or delta chain of the TCR of item 21.

Item 24. An expression vector comprising the nucleic acid of item 23 operably linked to at least one promoter sequence.

Item 25. A host cell transformed with the expression vector of item 24.

Item 26. The host cell of item 25 which is a T cell or T cell progenitor.

Item 27. The host cell of item 26 wherein the T cell or T cell progenitor is obtained from a cancer patient.

Item 28. The host cell of item 26 wherein the T cell or T cell progenitor is obtained from a healthy donor.

Item 29. A pharmaceutical composition comprising the TCR of any of items 1 to 22, a nucleic acid of item 23, an expression vector of item 24, and/or a host cell of any one of items 25 to 28; and a pharmaceutically acceptable carrier, and optionally, pharmaceutically acceptable excipients and/or stabilizers.

Item 30. A method for producing a TCR that specifically binds to the peptide of SEQ ID NO:1 when presented by an MHC molecule, said method comprising culturing the host cell of any one of items 25 to 28 under conditions suitable to promote expression of the TCR.

Item 31. A method of treating cancer comprising administering to a subject in need thereof the TCR of any of items 1 to 22, the nucleic acid of item 23, the expression vector of item 24, the host cell of any one of items 25 to 28, and/or the pharmaceutical composition of item 29.

Item 32. The method of item 31, wherein the TCR is expressed on the surface of a host cell.

Item 33. The method of item 31, wherein the host cell is selected from the group consisting of a T cell or T cell progenitor.

Item 34. The method of item 33, wherein the T cell or T cell progenitor is autologous.

Item 35. The method of item 33, wherein the T cell or T cell progenitor is allogeneic.

Item 36. The method of item 31, wherein the TCR is conjugated to a therapeutically active agent.

Item 37. The method of item 36, wherein the therapeutically active agent is selected from the group consisting of a radionuclide, a chemotherapeutic agent and a toxin.

Item 38. The method of any of items 31 to 37, wherein the cancer is non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer, esophageal cancer, or a combination thereof.

Item 39. The method of any of items 31 to 38, further comprising administering to the subject at least one chemotherapeutic agent.

Item 40. The method of any of items 31 to 39, further comprising administering radiation therapy to the subject.

Item 41. A method of treating cancer in a subject in need thereof, comprising:
a) isolating a cell from said subject;
b) transforming the cell with a vector encoding the TCR of any of items 1 to 22 to produce a transformed cell;
c) expanding the transformed cell to produce a plurality of transformed cells; and
d) administering the plurality of transformed cells to said subject.

Item 42. The method of item 41, wherein the cell is selected from a T cell or a T cell progenitor.

Item 43. A method of treating cancer in a subject in need thereof, comprising:
a) isolating a cell from a healthy donor;
b) transforming the cell with a vector encoding the TCR of any of items 1 to 22 to produce a transformed cell;
c) expanding the transformed cell to produce a plurality of transformed cells; and
d) administering the plurality of transformed cells to said subject.

Item 44. The method of item 43, wherein the cell is selected from a T cell or a T cell progenitor.

Item 45. A method of detecting cancer in a biological sample comprising:
a) contacting the biological sample with the TCR of any of items 1 to 22, and
b) detecting binding of the TCR to the biological sample.

Item 46. The method of item 45, wherein the TCR comprises a detectable label.

Item 47. The method of item 46, wherein the detectable label is selected from the group consisting of a radionuclide, a fluorophore and biotin.

Item 48. The method of any of items 45 to 47, wherein said detecting is carried out in vitro, in vivo or in situ.

Item 49. The method of any of items 45 to 48, wherein said cancer is non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer, esophageal cancer, or a combination thereof.

Item 50. The host cell of any of items 25 to 28 wherein the T cell is a gamma/delta T cell.

Item 51. A method of killing target-cells in a patient which target-cells aberrantly express MAG-003, the method comprising administering to the patient an effective number of T-cells expressing a TCR of any of items 1 to 22, the nucleic acid of item 23, the expression vector of item 24, the host cell of any one of items 25 to 28, and/or the pharmaceutical composition of item 29.

Item 52. The TCR of any of items 1 to 22 which is a soluble TCR.

Item 53. The TCR of any of items 1 to 22, wherein the alpha chain comprises a TCR alpha variable domain at least 95% identical to the amino acid sequence of any of SEQ ID NO:39, SEQ ID NO:55 and SEQ ID NO:71; and the beta chain comprises a TCR beta variable domain at least 95% identical to any of SEQ ID NO:47, SEQ ID NO:63 and SEQ ID NO:79, and wherein the TCR specifically binds to a MAG-003 peptide-MHC molecule complex.

Item 54. The TCR of any of items 1 to 22 having at least one mutation in the alpha chain relative to SEQ ID NO:39, SEQ ID NO:55 or SEQ ID NO:71 and/or having at least one mutation in the beta chain relative to SEQ ID NO:47, SEQ ID NO:63 and SEQ ID NO:79, and wherein the TCR has a binding affinity for, and/or a binding half-life for, a MAG- 003 peptide-HLA molecule complex, which is at least double that of the unmutated TCR for the same peptide.

Item 55. The TCR of any of items 1 to 22 having at least one mutation in the alpha chain relative to SEQ ID NO:39, SEQ ID NO:55 or SEQ ID NO:71 and/or having at least one mutation in the beta chain relative to SEQ ID NO:47, SEQ ID NO:63 and SEQ ID NO:79, and wherein the TCR has modified glycosylation compared to the unmutated TCR.

Item 56. The method of any of items 31 to 44 or 51, wherein the TCR of any of items 1 to 22, the nucleic acid of item 23, the expression vector of item 24, the host cell of any of items 25 to 28 or the pharmaceutical composition of item 29 is administered in at least two administrations separated by at least 24 hours.

Item 57. The method of item 56, wherein the TCR of any of items 1 to 22, the nucleic acid of item 23, the expression vector of item 24, the host cell of any of items 25 to 28 or the pharmaceutical composition of item 29 is administered to the subject over a period of days, weeks or months.

Item 58. The method of items 56 or 57, wherein the TCR of any of items 1 to 22, the nucleic acid of item 23, the expression vector of item 24, the host cell of any of items 25 to 28 or the pharmaceutical composition of item 29 is administered by local infusion.

Item 59. The method of any of item 58, wherein the local infusion is administered by an infusion pump and/or a catheter system.

Item 60. The method of items 58 or 59, wherein said local infusion is into a solid tumor, a blood vessel that feeds a solid tumor, and/or the area surrounding a solid tumor.

Item 61. The method of any of items 31 to 44, 51 or 56 to 60, wherein the TCR of any of items 1 to 22, the nucleic acid of item 23, the expression vector of item 24, the host cell of any of items 25 to 28 or the pharmaceutical composition of item 29 is administered in a dose of about $10^4$ to about $10^{10}$ cells per dose.

Item 62. A TCR comprising at least one alpha chain complementarity determining region (CDR) selected from the group consisting of an alpha chain CDR1, CDR2 and CDR3 of SEQ ID NO:39, SEQ ID NO:55 and SEQ ID NO:71; and/or at least one beta chain complementarity determining region (CDR) selected from the group consisting of a beta chain CDR1, CDR2 and CDR3 of SEQ ID NO:47, SEQ ID NO:63 and SEQ ID NO:79, and wherein the TCR specifically binds to a MAG-003 peptide-MHC molecule complex.

EXAMPLES

Allo-reactive settings can be used to circumvent self-tolerance and yield T-cells with a higher avidity when compared to T-cells derived from autologous settings, i.e., patients. Examples of such settings include in vitro generation of allo-HLA reactive, peptide-specific T-cells (Sadovnikova et al. 1998; Savage et al. 2004; Wilde et al. 2012), and immunization of mice transgenic for human-MHC or human TCR (Stanislawski et al. 2001; Li et al. 2010).

Example 1: In Vitro Generation of Allo-HLA Reactive, Peptide-Specific T-Cells (Savage et al. 2004)

PBMCs from HLA-A*02-positive and HLA-A*02-negative healthy donors were used after obtaining informed consent. Recombinant biotinylated HLA-A2 class I monomers and A2 fluorescent tetramers containing MAG-003 were obtained from MBLI (Woburn, Mass.). PBMCs were incubated with anti-CD20SA diluted in phosphate buffered saline (PBS) for 1 hour at room temperature, washed, and incubated with the biotinylated A2/MAG-003 monomers for 30 minutes at room temperature, washed, and plated at $3\times10^6$ cells/well in 24-well plates in RPMI with 10% human AB serum. Interleukin 7 (IL-7; R&D Systems, Minneapolis, Minn.) was added on day 1 at 10 ng/mL and IL-2 (Chiron, Harefield, United Kingdom) was added at 10 U/mL on day 4. Over a 5-week period cells were restimulated weekly with fresh PBMCs, mixed with responder cells at a 1:1 ratio, and plated at $3\times10^6$/well in 24-well plates.

To obtain high avidity T-cells, approximately $10^6$ PBMCs with HLA-A2/MAG-003 tetramer-phycoerythrin (PE) (obtained from MBLI) were incubated for 30 minutes at 37° C., followed by anti-CD8-fluorescein isothiocyanate (FITC)/allophycocyanin (APC) for 20 minutes at 4° C., followed by fluorescence activated cell sorting (FACS)-Calibur analysis. Sorting was done with a FACS-Vantage (Becton Dickinson, Cowley, Oxford, United Kingdom). Sorted tetramerpositive cells were expanded in 24-well plates using, per well, $2\times10^5$ sorted cells, $2\times10^6$ irradiated A2-negative PBMCs as feeders, $2\times10^4$ CD3/CD28 beads/mL (Dynal, Oslo Norway), and IL-2 (1000 U/mL). The high avidity T-cells, thus obtained, were then used to identify and isolate TCRs using techniques known in the art, such as single cell 5' RACE (Rapid Amplification of cDNA Ends). Non-redundant TCR DNAs were then analyzed for amino acid/DNA sequences determination and cloning into expression vectors using methods well known in the art.

Example 2: Immunization of Mice Transgenic for Human-MHC or Human TCR

MAG-003 are used to immunize transgenic mice with the entire human TCRαβ gene loci (1.1 and 0.7 Mb), whose T-cells express a diverse human TCR repertoire that compensates for mouse TCR deficiency. (Li et al. 2010). To obtain high avidity T-cells, PBMCs obtained from the transgenic mice are incubated with tetramer-phycoerythrin (PE) followed by cell sorting as described above. The high avidity T-cells, thus obtained, are then used to identify and isolate TCRs for amino acid/DNA sequences determination and cloning into expression vectors using methods described in the art.

In an aspect, MAG-003 and its variants, i.e., p286-1Y2L (having 2 amino acid substitutions, SEQ ID NO:13) and p286-1Y2L9L (having 3 amino acid substitutions, SEQ ID NO:14) exhibit potent binding affinity and stability towards HLA-A*0201 molecule. In particular, p286-1Y2L9L showed the capability to induce specific CTLs which, in an aspect, lyse the target cancer cells from both PBMCs of healthy donors and HLA-A2.1 AKb transgenic mice. See, for example, (Wu et al. 2011), the content of which is hereby incorporated by reference in its entirety.

To obtain high avidity TCRs for MHC I or II/p286-1Y2L or p286-1Y2L9L complexes, these peptides can be used in methods described in Examples 1 and 2. The high avidity T-cells, thus obtained, are then used to identify and isolate TCRs for amino acid/DNA sequences determination and cloning into expression vectors using methods described are in the art.

Example 3: Cloning of TCRs

Methods of cloning TCRs are known in the art, for example, as described in U.S. Pat. No. 8,519,100, which is hereby incorporated by reference in its entirety for said methods. The alpha chain variable region sequence specific oligonucleotide A1 (ggaattccatatgagtcaacaaggagaagaagatcc SEQ ID NO:26) which encodes the restriction site NdeI, an introduced methionine for efficient initiation of expression in bacteria, and an alpha chain constant region sequence specific oligonucleotide A2 (ttgtcagtcgacttagagtctctcagctgg-tacacg SEQ ID NO:27) which encodes the restriction site SalI are used to amplify the alpha chain variable region. In the case of the beta chain, a beta chain variable region sequence specific oligonucleotide B1 (tctctcatatggatggtg-gaattactcaatccccaa SEQ ID NO:28) which encodes the restriction site NdeI, an introduced methionine for efficient initiation of expression in bacteria, and a beta chain constant region sequence specific oligonucleotide B2 (tagaaaccggtg-gccaggcacaccagtgtggc SEQ ID NO:29) which encodes the restriction site AgeI are used to amplify the beta chain variable region.

The DNA sequences encoding the TCR alpha chain cut with NdeI and SalI are ligated into pGMT7+Cα vector, which was cut with NdeI and XhoI. The DNA sequences encoding the TCR beta chain cut with NdeI and AgeI was ligated into separate pGMT7+Cβ vector, which was also cut with NdeI and AgeI. Ligated plasmids are transformed into competent *Escherichia coli* strain XL1-blue cells and plated out on LB/agar plates containing 100 µg/ml ampicillin. Following incubation overnight at 37° C., single colonies are picked and grown in 10 ml LB containing 100 µg/ml ampicillin overnight at 37° C. with shaking. Cloned plasmids are purified using a Miniprep kit (Qiagen) and the insert is sequenced using an automated DNA sequencer (Lark Technologies).

Three TCRs (R20P1H7, R7P1D5 and R10P2G12, see table 2), each encoding tumor specific TCR-alpha and TCR-beta chains, were isolated and amplified from T-cells of healthy donors.

Cells from healthy donors were in vitro stimulated according to the method described in Walter et. al. 2003. Target-specific cells were single-cell sorted using target-specific multimers for subsequent TCR isolation. TCR sequences were isolated via 5' RACE by standard methods as described by e.g. Molecular Cloning a laboratory manual fourth edition by Green and Sambrook. All three TCRs were derived from HLA-A2 positive donors. The alpha and beta variable regions of TCRs R20P1H7, R7P1D5 and R10P2G12 were sequenced.

The R20P1H7 TCR alpha variable domain was found to have an amino acid sequence corresponding to residues 22-133 of SEQ ID NO:39. The R20P1H7 TCR beta variable domain was found to have an amino acid sequence corresponding to residues 20-135 of SEQ ID NO:47.

The R7P1D5 TCR alpha variable domain has an amino acid sequence corresponding to residues 22-131 of SEQ ID NO:55. The R7P1D5 TCR beta variable domain has an amino acid sequence corresponding to residues 20-131 of SEQ ID NO:63.

The R10P2G12 TCR alpha variable domain has an amino acid sequence corresponding to residues 21-136 of SEQ ID NO:71. The R10P2G12 TCR beta variable domain has an amino acid sequence corresponding to residues 20-134 of SEQ ID NO:79.

Phage display can be used to generate libraries of TCR variants to identify high affinity mutants. The TCR phage display and screening methods described in (Li et al, (2005) Nature Biotech 23 (3): 349-354) can be applied to a reference TCR selected from the TCRs described in Table 2.

For example, all three CDR regions of the alpha chain sequence of SEQ ID NOs: 39, 55 and 71; and all three CDR regions of the beta chain sequence of SEQ ID NOs: 47, 55 and 79 can be targeted by mutagenesis, and each CDR library panned and screened separately.

Accordingly, TCRs with affinities and/or binding half-lives at least twice that of a reference TCR (and therefore impliedly at least twice that of the native TCR) are identified.

TCR heterodimers are refolded using the method including the introduced cysteines in the constant regions to provide the artificial inter-chain disulphide bond. In that way TCRs are prepared, consisting of (a) the reference TCR beta chain, together with mutated alpha chains; (b) the reference TCR alpha chain together with mutated beta chains; and (c) various combinations of beta and alpha chains including the mutant variable domains.

The interaction between high affinity soluble disulfide-linked TCRs, and TCR variants, and the native peptide KVLEHVVRV (SEQ ID NO:1) HLA-A*02 complex can be analysed using the BIAcore method.

High avidity TCR variants can also be selected from a library of CDR mutants by yeast, or T-cell display (Holler et al. 2003; Chervin et al. 2008). Candidate TCR variants, thus, provide guidance to design mutations of the TCR's CDRs to obtain high avidity TCR variants (Robbins et al. 2008; Zoete et al. 2007).

Example 4: Autologous T-Cell Engineering

T-cells can be engineered to express high avidity TCRs (so-called TCR therapies) or proteinfusion derived chimeric antigen receptors (CARs) that have enhanced antigen specificity to MHC I/MAG-003 complex or MHC II/MAG-003 complex. In an aspect, this approach overcomes some of the limitations associated with central and peripheral tolerance, and generate T-cells that will be more efficient at targeting tumors without the requirement for de novo T-cell activation in the patient.

In one aspect, to obtain T-cells expressing TCRs of the present description, nucleic acids encoding the tumor specific TCR-alpha and/or TCR-beta chains identified and isolated, as described in Examples 1-3, are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs were synthesized by techniques described in the art, e.g., in vitro transcription systems. The in vitro-synthesized TCR RNAs were then introduced into primary CD8+ T-cells obtained from healthy donors by electroporation to re-express tumor specific TCR-alpha and/or TCR-beta chains.

To determine specificity and affinity of TCRs, the transformed CD8+ T-cells were co-incubated with MAG-003-loaded target cells or with target cells loaded with homologous but unrelated peptide RABGAP1L-001 (SEQ ID NO:91), AXIN1-001 (SEQ ID NO:92), ANO5-001 (SEQ ID NO:93), TPX2-001 (SEQ ID NO:94), SYNE3-001 (SEQ ID NO:95), MIA3-001 (SEQ ID NO:96), HERC4-001 (SEQ ID NO:97), PSME2-001 (SEQ ID NO:98), HEATR5A-001 (SEQ ID NO:99) or CNOT1-003 (SEQ ID NO:100) or control peptide NYESO1-001 (SEQ ID NO:101), followed by IFN-γ release assay. Unloaded target cells and CD8+ T-cells alone served as controls. IFN-γ secretion from CD8+ T-cells is indicative of T-cell activation with cytotoxic activity.

TABLE 11

| TCR No. | TCR Code | Donor/HLA-A2 (+ or −) | IFNγ (pg/ml) | EC50 | % MAG-003 TET-positive primary CD8+ T-cells | % NYESO1-001 TET-positive primary CD8+ T-cells |
|---|---|---|---|---|---|---|
| 1 | R7P1D5 | HBC-583/(+) | 400-1050 | ~3 nM | 7.99 | 0.87 |
| 2 | R20P1H7 | HBC-689/(+) | 200-900 | ~10 nM | 5.73 | 0.87 |
| 3 | R10P2G12 | HBC-673/(+) | 200-1500 | ~10 nM | 5.38 | 0.87 |

Figure 5:
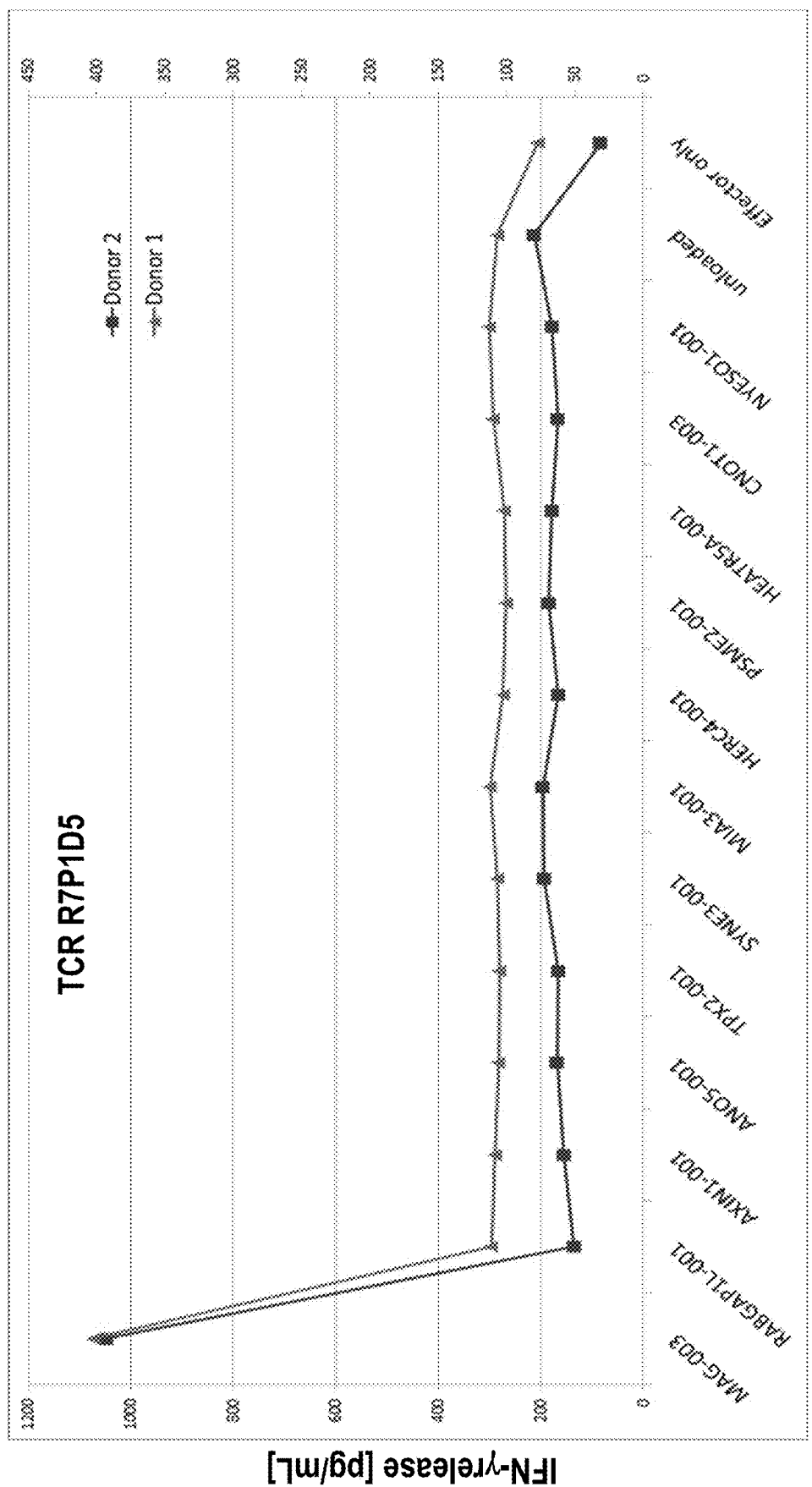
FIG. 5 shows IFNγ release from CD8+ T-cells electroporated with alpha and beta chain RNA of TCRs R7P1D5, R20P1H7 and R10P2G12 (Table 2), respectively, after co-incubation with target cells loaded with MAG-003 peptide (SEQ ID NO:1) or homologous but unrelated peptide RABGAP1L-001 (SEQ ID NO:91), AXIN1-001 (SEQ ID NO:92), ANO5-001 (SEQ ID NO:93), TPX2-001 (SEQ ID NO:94), SYNE3-001 (SEQ ID NO:95), MIA3-001 (SEQ ID NO:96), HERC4-001 (SEQ ID NO:97), PSME2-001 (SEQ ID NO:98), HEATR5A-001 (SEQ ID NO:99) or CNOT1-003 (SEQ ID NO:100) or control peptide NYESO1-001 (SEQ ID NO:101). IFNγ release data were obtained with CD8+ T-cells derived from two different donors (donor 1 on right X-axis, donor 2 on left X-axis). RNA electroporated CD8+ T-cells alone or in co-incubation with unloaded target cells served as controls.
Figure 6:
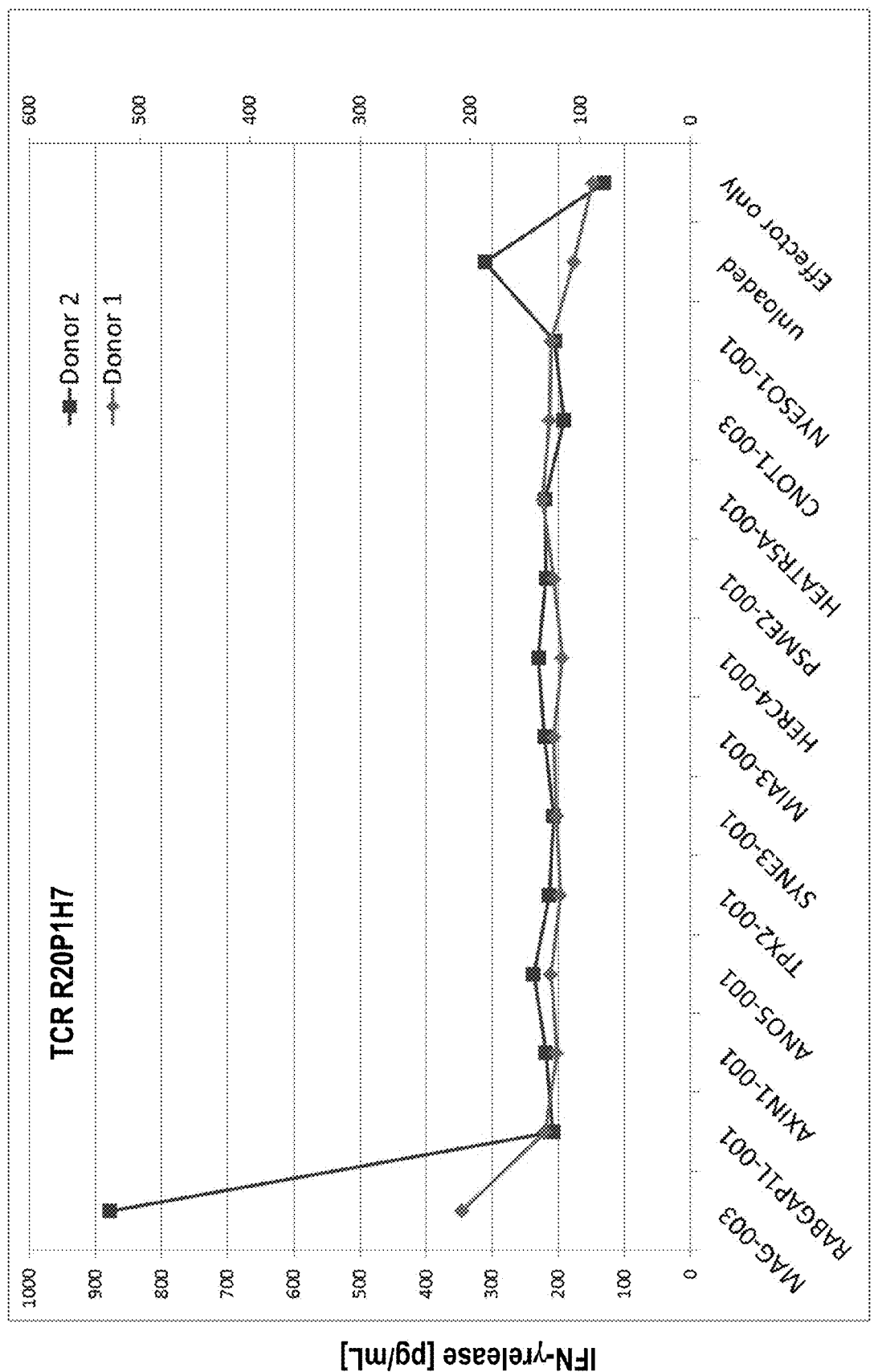
FIG. 6 shows IFNγ release from CD8+ T-cells electroporated with alpha and beta chain RNA of TCRs R7P1D5, R20P1H7 and R10P2G12 (Table 2), respectively, after co-incubation with target cells loaded with MAG-003 peptide (SEQ ID NO:1) or homologous but unrelated peptide RABGAP1L-001 (SEQ ID NO:91), AXIN1-001 (SEQ ID NO:92), ANO5-001 (SEQ ID NO:93), TPX2-001 (SEQ ID NO:94), SYNE3-001 (SEQ ID NO:95), MIA3-001 (SEQ ID NO:96), HERC4-001 (SEQ ID NO:97), PSME2-001 (SEQ ID NO:98), HEATR5A-001 (SEQ ID NO:99) or CNOT1-003 (SEQ ID NO:100) or control peptide NYESO1-001 (SEQ ID NO:101). IFNγ release data were obtained with CD8+ T-cells derived from two different donors (donor 1 on right X-axis, donor 2 on left X-axis). RNA electroporated CD8+ T-cells alone or in co-incubation with unloaded target cells served as controls.
Figure 7:
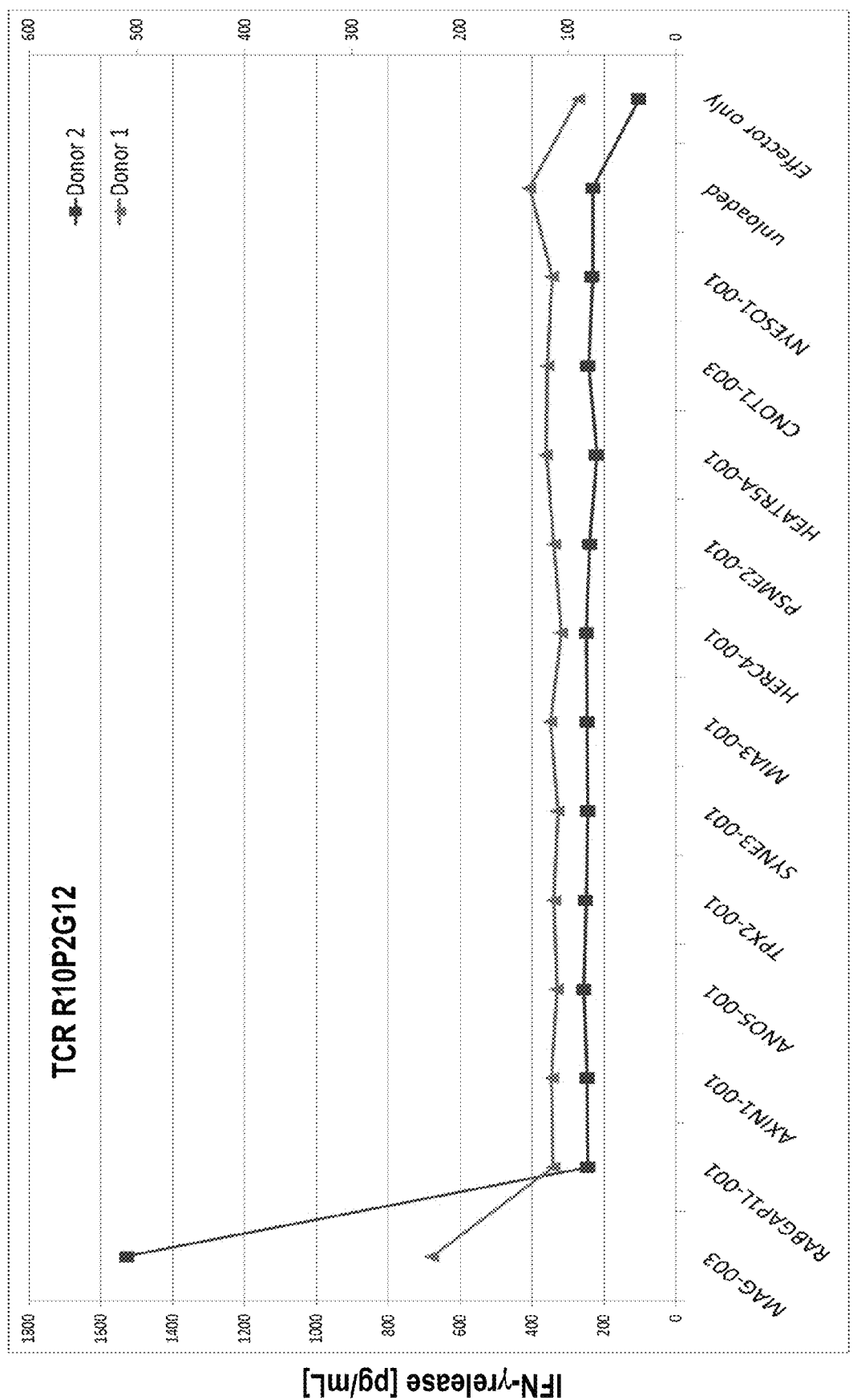
FIG. 7 shows IFNγ release from CD8+ T-cells electroporated with alpha and beta chain RNA of TCRs R7P1D5, R20P1H7 and R10P2G12 (Table 2), respectively, after co-incubation with target cells loaded with MAG-003 peptide (SEQ ID NO:1) or homologous but unrelated peptide RABGAP1L-001 (SEQ ID NO:91), AXIN1-001 (SEQ ID NO:92), ANDS-001 (SEQ ID NO:93), TPX2-001 (SEQ ID NO:94), SYNE3-001 (SEQ ID NO:95), MIA3-001 (SEQ ID NO:96), HERC4-001 (SEQ ID NO:97), PSME2-001 (SEQ ID NO:98), HEATR5A-001 (SEQ ID NO:99) or CNOT1-003 (SEQ ID NO:100) or control peptide NYESO1-001 (SEQ ID NO:101). IFNγ release data were obtained with CD8+ T-cells derived from two different donors (donor 1 on right X-axis, donor 2 on left X-axis). RNA electroporated CD8+ T-cells alone or in co-incubation with unloaded target cells served as controls.

As shown in FIGS. 5-7 all primary CD8+ T-cells transformed with TCRs of the present disclosure, after co-incubation with MAG-003-loaded target cells, released much higher levels of IFN-γ than that stimulated by unrelated peptide-loaded target cells, and the controls. Target peptide titration analysis showed EC50 ranges from about 3 nM to about 10 nM (Table 11). These results suggest that TCRs of the present invention can activate cytotoxic T-cell activity, e.g., IFN-γ release, through specific interaction with the MHC/MAG-003 complex.

Figure 8:
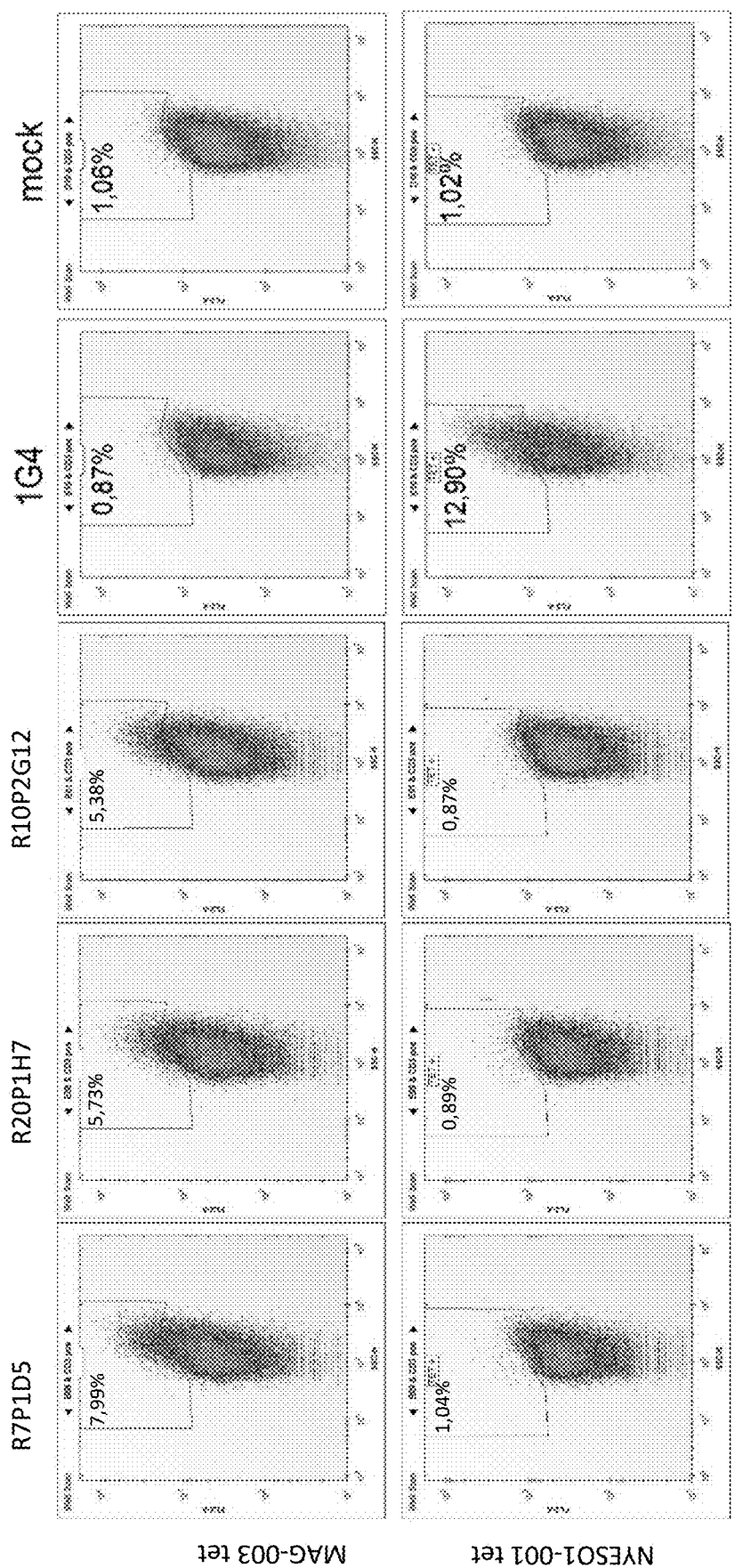
FIG. 8 show MHC/MAG-003 tetramer or MHC/NYESO1-001 tetramer staining of CD8+ T-cells electroporated with alpha and beta chain RNA of TCRs R7P1D5, R20P1H7 and R10P2G12 (Table 2), respectively. CD8+ T-cells electroporated with RNA of 1G4 TCR that specifically binds to MHC/NYESO1-001 complex and mock electroporated CD8+ T-cells served as controls.
Figure 9:
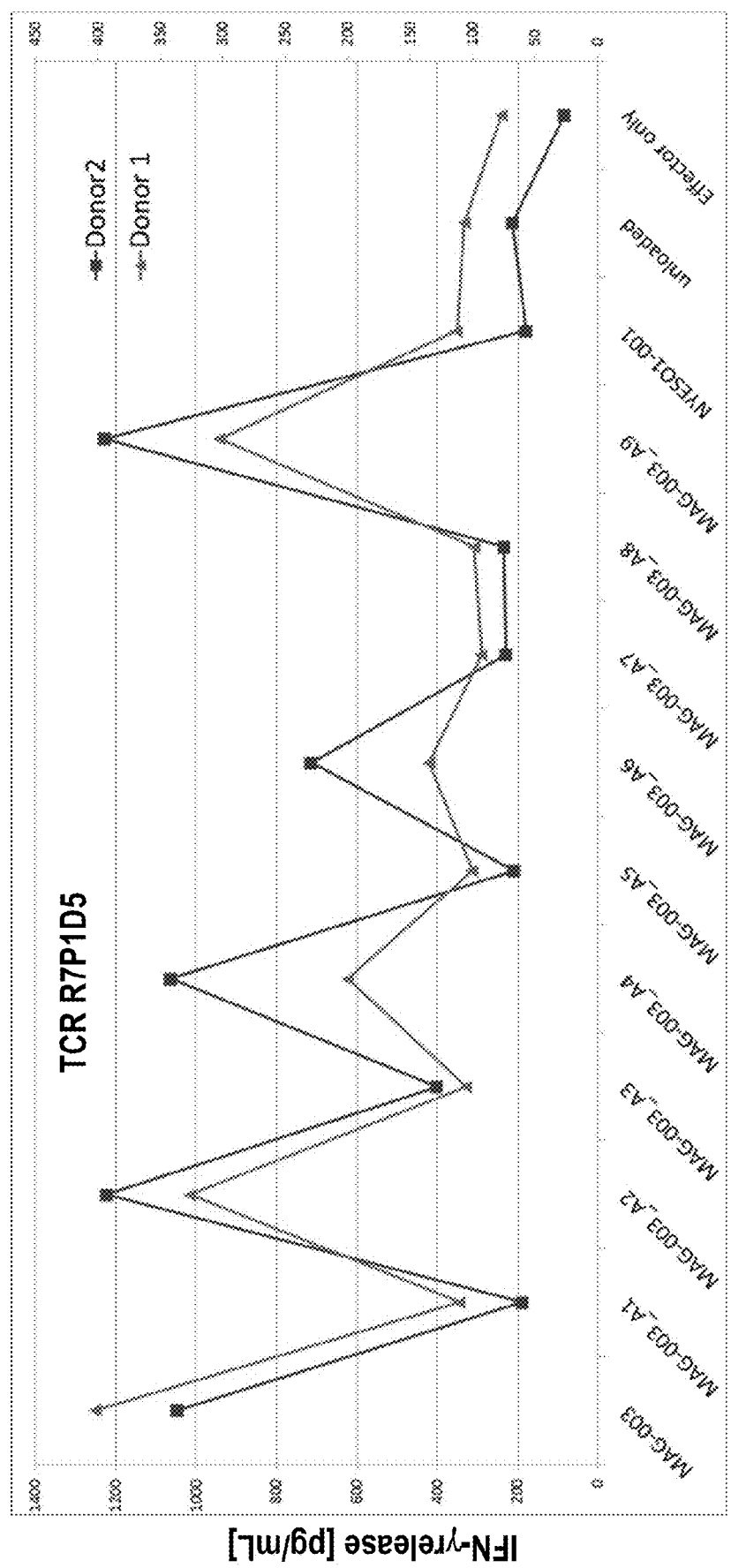
FIG. 9 shows IFNγ release from CD8+ T-cells electroporated with alpha and beta chain RNA of TCRs R7P1D5, R20P1H7 and R10P2G12 (Table 2), respectively, after co-incubation with target cells loaded with MAG-003 peptide (SEQ ID NO:1) or various MAG-003 alanine-substitution variants at positions 1-9 of SEQ ID NO:1. RNA-electroporated CD8+ T-cells alone or in co-incubation with target cells loaded with control peptide NYESO1-001 or unloaded target cells served as controls. IFNγ release data were obtained with CD8+ T-cells derived from two different donors (donor 1 on right X-axis, donor 2 on left X-axis).
Figure 10:
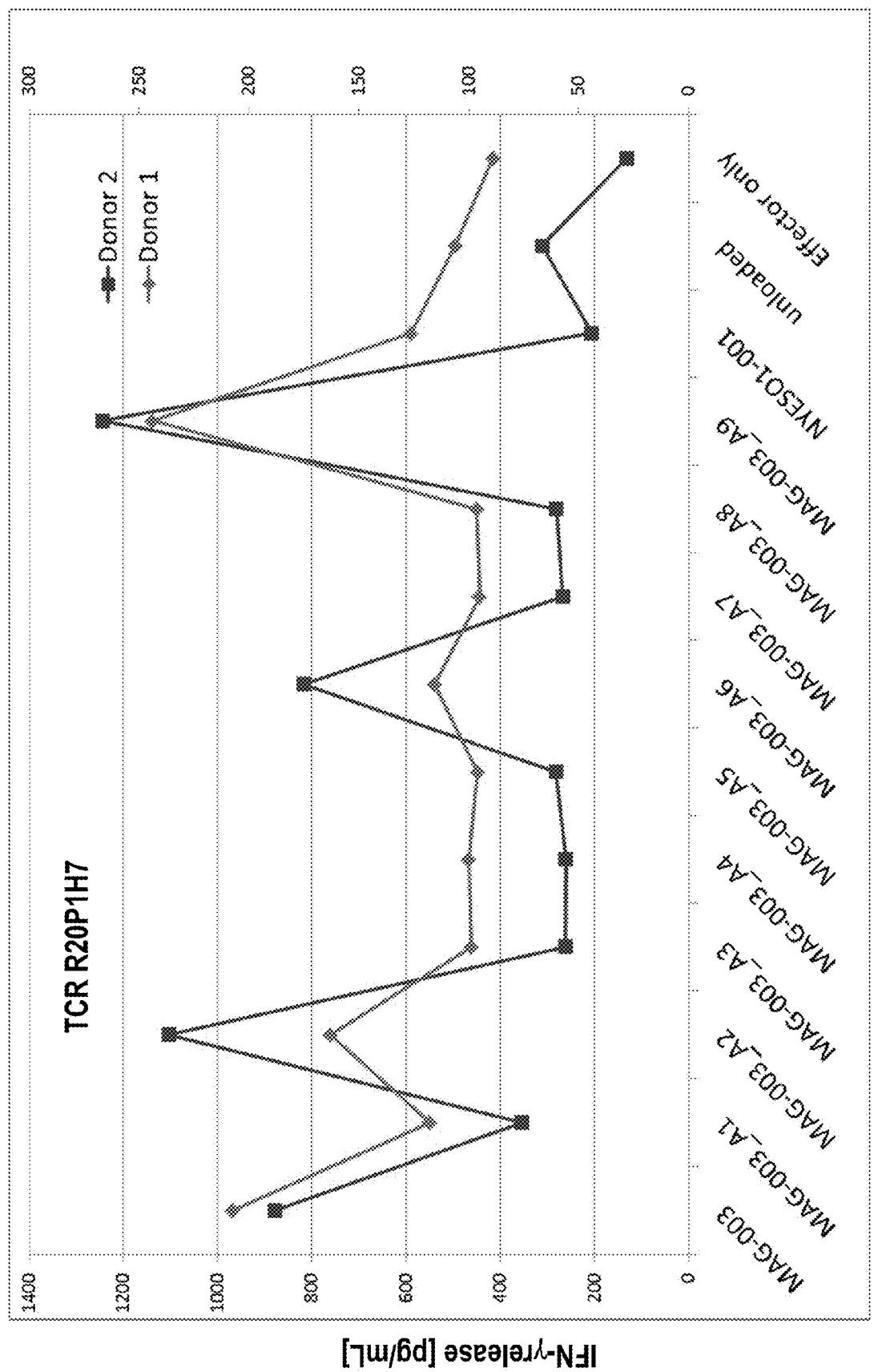
FIG. 10 shows IFNγ release from CD8+ T-cells electroporated with alpha and beta chain RNA of TCRs R7P1D5, R20P1H7 and R10P2G12 (Table 2), respectively, after co-incubation with target cells loaded with MAG-003 peptide (SEQ ID NO:1) or various MAG-003 alanine-substitution variants at positions 1-9 of SEQ ID NO:1. RNA-electroporated CD8+ T-cells alone or in co-incubation with target cells loaded with control peptide NYESO1-001 or unloaded target cells served as controls. IFNγ release data were obtained with CD8+ T-cells derived from two different donors (donor 1 on right X-axis, donor 2 on left X-axis).
Figure 11:
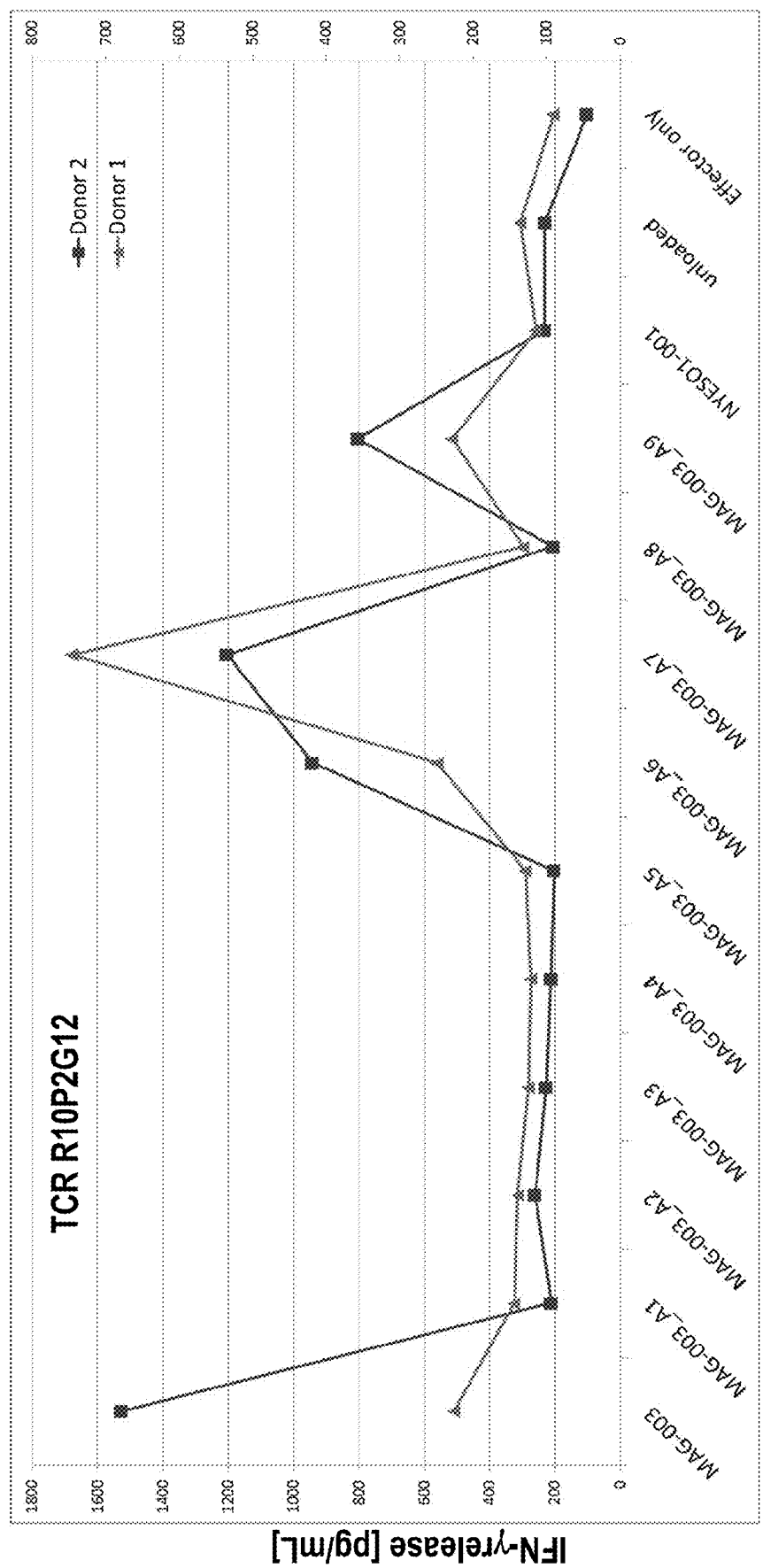
FIG. 11 shows IFNγ release from CD8+ T-cells electroporated with alpha and beta chain RNA of TCRs R7P1D5, R20P1H7 and R10P2G12 (Table 2), respectively, after co-incubation with target cells loaded with MAG-003 peptide (SEQ ID NO:1) or various MAG-003 alanine-substitution variants at positions 1-9 of SEQ ID NO:1. RNA-electroporated CD8+ T-cells alone or in co-incubation with target cells loaded with control peptide NYESO1-001 or unloaded target cells served as controls. IFNγ release data were obtained with CD8+ T-cells derived from two different donors (donor 1 on right X-axis, donor 2 on left X-axis).
Figure 12:
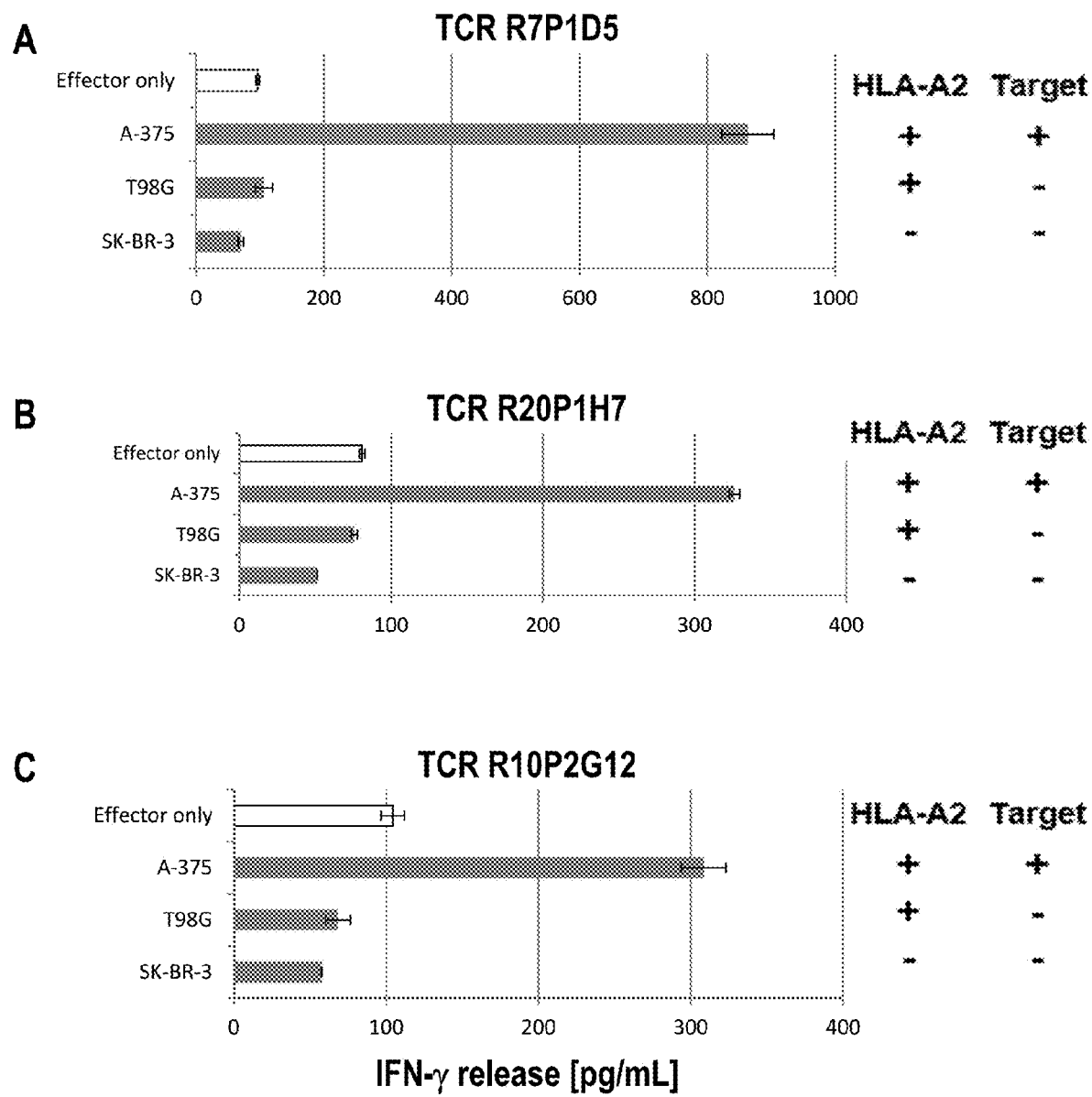
FIG. 12 IFNγ release from CD8+ T-cells electroporated with alpha and beta chain RNA of TCRs (A) R7P1D5, (B) R20P1H7, and (C) R10P2G12 after co-incubation with A-375 melanoma cell line, T98G glioblastoma cell line and SK-BR-3 breast cancer cell line, respectively. RNA-electroporated CD8+ T-cells alone served as a control.

T-cell activation was further confirmed using a tetramer staining technique to detect MHC/MAG-003-binding activated cytotoxic T-cells. As shown in FIG. 8 and Table 11, a higher percentage of TCR-expressing CD8+ T-cells were stained positive fluorescent-labeled MHC/MAG-003 tetramer than that with MHC/NYESO1-001 control tetramer or mock control. As a control, primary CD8+ T-cells transformed with TCRs, such as 1G4 TCR, which is known to bind specifically to MHC/NYESO1-001 complex, was readily activated by NYESO1-001-loaded target cells. The alpha and beta chains of TCR 1G4 are shown in SEQ ID NO:89 and 90, respectively:

```
1G4 alpha chain (SEQ ID NO: 89):
METLLGLLILWLQLQWVSSKQEVTQIPAALSVPEGENLVLNCSFTDSAIY

NLQWFRQDPGKGLTSLLLIQSSQREQTSGRLNASLDKSSGRSTLYIAASQ

PGDSATYLCAVRPTSGGSYIPTFGRGTSLIVHPYIQNPDPAVYQLRDSKS

SDKSVCLFTDFDSQTNVSQSKDSDVYITDKTVLDMRSMDFKSNSAVAWSN

KSDFACANAFNNSIIPEDTFFPSPESSCDVKLVEKSFETDTNLNFQNLSV

IGFRILLLKVAGFNLLMTLRLWSS

1G4 beta chain (SEQ ID NO: 90):
MSIGLLCCAALSLLWAGPVNAGVTQTPKFQVLKTGQSMTLQCAQDMNHEY

MSWYRQDPGMGLRLIHYSVGAGITDQGEVPNGYNVSRSTTEDFPLRLLSA

APSQTSVYFCASSYVGNTGELFFGEGSRLTVLEDLKNVFPPEVAVFEPSE

AEISHTQKATLVCLATGFYPDHVELSWWVNGKEVHSGVSTDPQPLKEQPA

LNDSRYCLSSRLRVSATFWQNPRNHFRCQVQFYGLSENDEWTQDRAKPVT

QIVSAEAWGRADCGFTSESYQQGVLSATILYEILLGKATLYAVLVSALVL

MAMVKRKDSRG
```

To determine the binding motif of the TCRs for the MAG-003/MHC complex, positional alanine scanning analysis was performed at each of the 9 amino acids of the MAG-003 peptide. Alanine-substituted MAG-003 peptides are shown in Table 12.

TABLE 12

| Position: | 1 | 2 | 3 | 4 | 5 | 6 | 7 | 8 | 9 |
|---|---|---|---|---|---|---|---|---|---|
| MAG-003 (SEQ ID NO:1) | K | V | L | E | H | V | V | R | V |
| MAG-003 A1 (SEQ ID NO:30) | A | V | L | E | H | V | V | R | V |
| MAG-003 A2 (SEQ ID NO:31) | K | A | L | E | H | V | V | R | V |
| MAG-003 A3 (SEQ ID NO:32) | K | V | A | E | H | V | V | R | V |
| MAG-003 A4 (SEQ ID NO:33) | K | V | L | A | H | V | V | R | V |
| MAG-003 A5 (SEQ ID NO:34) | K | V | L | E | A | V | V | R | V |
| MAG-003 A6 (SEQ ID NO:35) | K | V | L | E | H | A | V | R | V |
| MAG-003 A7 (SEQ ID NO:36) | K | V | L | E | H | V | A | R | V |
| MAG-003 A8 (SEQ ID NO:37) | K | V | L | E | H | V | V | A | V |
| MAG-003 A9 (SEQ ID NO:38) | K | V | L | E | H | V | V | R | A |

CD8+ T-cells electroporated with RNA encoding TCR of interest were co-incubated with target cells loaded with MAG-003, MAG-003-A1 to MAG-003-A9, or an unrelated NYESO1-001 peptide, followed by IFNγ release assay, as described above.

Results of positional alanine scanning analysis are shown in FIGS. 9-11 and summarized in Table 13.

TABLE 13

| TCR | MAG-003 positions enable TCR binding |
|---|---|
| R7P1D5 | 1, 3, 5, 7, 8 |
| R20P1H7 | 1, 3, 4, 5, 7, 8 |
| R10P2G12 | 1, 2, 3, 4, 5, 8 |

A genome-wide screen for A*02-binding peptides with an identical motif revealed no potentially cross-reactive peptides for the TCRs R20P1H7, R7P1D5 and R10P2G12, respectively. These results suggest that the TCRs described herein exhibit a very specific recognition pattern with a reduced risk of off-target effects.

To determine efficacy of T-cells expressing TCRs described herein, primary CD8+ T-cells electroporated with RNA of the TCRs R7P1D5, R20P1H7 and R10P2G12 were co-incubated with different human cancer cell lines, e.g., A-375 (human melanoma cell line, which is positive for HLA-A2 and MAG-003 expression), T98G (human glioblastoma cell line, which is HLA-A2-positive and MAG-003-negative), and SK-BR-3 (human breast cancer cell line, which is HLA-A2-negative and MAG-003-negative), followed by IFNγ release assay.

As shown in FIG. 12A-C, IFNγ release was observed in A-375 cells, which are HLA-A2-positive and MAG-003-positive, but not in T98G and SK-BR-3 cells, which have basal levels of IFNγ release that is comparable to that of effector cell only control. In addition, CD8+ T-cells transformed with TCR R7P1D5, but not controls, also exhibited increased IFNγ release when co-incubated with the human non-small cell cancer cell line, H1755 (data not shown). These results indicate that T-cells expressing TCRs R7P1D5, R20P1H7 and R10P2G12 can specifically induce cytotoxic activity targeting cancer cells in a HLA-A2/MAG-003 specific manner.

The present description provides TCRs that are useful in treating cancers/tumors, preferably melanoma and non-small cell lung cancer that over- or exclusively present MAG-003.

Example 5: Allogeneic T-Cell Engineering

Gamma delta (γδ) T cells, which are non-conventional T lymphocyte effectors implicated in the first line of defense against pathogens, can interact with and eradicate tumor cells in a MHC-independent manner through activating receptors, among others, TCR-gamma and TCR-delta chains. These γδ T cells display a preactivated phenotype that allows rapid cytokine production (IFN-γ, TNF-α) and strong cytotoxic response upon activation. These T-cells have anti-tumor activity against many cancers and suggest that γδ T cell-mediated immunotherapy is feasible and can induce objective tumor responses. (Braza et al. 2013).

Recent advances using immobilized antigens, agonistic monoclonal antibodies (mAbs), tumor-derived artificial antigen presenting cells (aAPC), or combinations of activating mAbs and aAPC have been successful in expanding gamma delta T-cells with oligoclonal or polyclonal TCR repertoires. For example, immobilized major histocompatibility complex Class-I chain-related A was a stimulus for γδ T-cells expressing TCRδ1 isotypes, and plate-bound activating antibodies have expanded Vδ1 and Vδ2 cells ex vivo. Clinically sufficient quantities of TCRδ1, TCRδ2, and TCRδ1$^{neg}$TCRδ2$^{neg}$ have been produced following co-culture on aAPC, and these subsets displayed differences in memory phenotype and reactivity to tumors in vitro and in vivo. (Deniger et al. 2014).

In addition, γδ T-cells are amenable to genetic modification as evidenced by introduction of TCR-alpha and TCR-beta chains. (Hiasa et al. 2009). Another aspect of the present description relates to production of γδ T-cells expressing TCR-alpha and TCR-beta that bind to MAG-003. To do so, γδ T-cells are expanded by methods described by Deniger et al. 2014, followed by transducing the recombinant viruses expressing the TCRs that bind to MAG-003 (as described in Example 3) into the expanded γδ T-cells. The virus-transduced γδ T-cells are then infused into the patient.

Example 6: Safety of MAG-003-Specific TCRs

Three MAG-003-specific TCRs (R7P1D5, R10P2G12, R20P1H7, see Table 2), each encoding tumor specific TCR-alpha and TCR-beta chains, were isolated and amplified from T-cells of healthy donors. Cells from healthy donors were in vitro stimulated according to a method previously described (Walter et al., 2003 J Immunol., November 15; 171(10):4974-8) and target-specific cells were single-cell sorted using HLA-A*02 multimers and then used for subsequent TCR isolation. TCR sequences were isolated via 5' RACE by standard methods as described by e.g. Molecular Cloning a laboratory manual fourth edition by Green and Sambrook. The alpha and beta variable regions of TCRs R7P1D5, R10P2G12 and R20P1H7 were sequenced and cloned for further functional characterization. TCRs R7P1D5, R10P2G12 and R20P1H7 are derived from a HLA-A*02 positive donor.

TABLE 13

Target Cell Types

| Cell type | Abbrevation | source |
|---|---|---|
| Normal Human Dermal Fibroblasts | NHDF | Primary cells |
| Human Coronary Artery Smooth Muscle Cells | HCASMC | Primary cells |
| Human Bronchial Smooth Muscle Cells | HBSMC | Primary cells |
| Human Renal Epithelial Cells | HREpC | Primary cells |
| Human Cardiomyocytes | HCM | Primary cells |
| Human Cardiac Microvascular Endothelial Cells | HCMEC | Primary cells |
| Human Hepatocytes | HH | Primary cells |
| Human Astrocytes | HA | Primary cells |
| Human Perineural Cells | HPC | Primary cells |
| Human Meningeal Cells | HMC | Primary cells |
| Human Neurons | HN | iPSC-derived cells |

TCRs of interest were expressed in human T cells via RNA electroporation and the T cells were assessed for IFN-γ release after co-culture with different target cells, such as T2 cells loaded with different peptides as well as tumor cell lines and primary cells from healthy tissues. T-cell activation data are shown in absolute IFN-γ levels or a normalized way as indicated below.

Efficacy of CD8+ T cells expressing TCRs R7P1D5, R10P2G12 and R20P1H7 was determined by T cell activation studies (IFN-γ release) using different tumor cell lines as target cells. The characterization of the safety profile of TCRs of interest was approached by testing the potential activation of TCR-expressing T cells upon co-culture with isolated primary cell types from healthy tissues and induced pluripotent stem cell (iPSC)-derived cell types from HLA-A*02-positive donors (Table 13). Cell types were selected in a manner to cover most of the critical organs like e.g. brain, heart and liver and different cell types as epithelium, endothelium or smooth muscle. Tumor cell lines were analyzed sideby-side as positive and negative controls.

Normalization method for IFNγ release:

$$\text{Mean}_{norm(TCRoi;co)} = [\text{mean}_{(TCRoi;co)} - \text{mean}_{(TCRoi;effector\ only)}] - [\text{mean}_{(mock;co)} - \text{mean}_{(mock;effector\ only)}]$$

Figure 13:
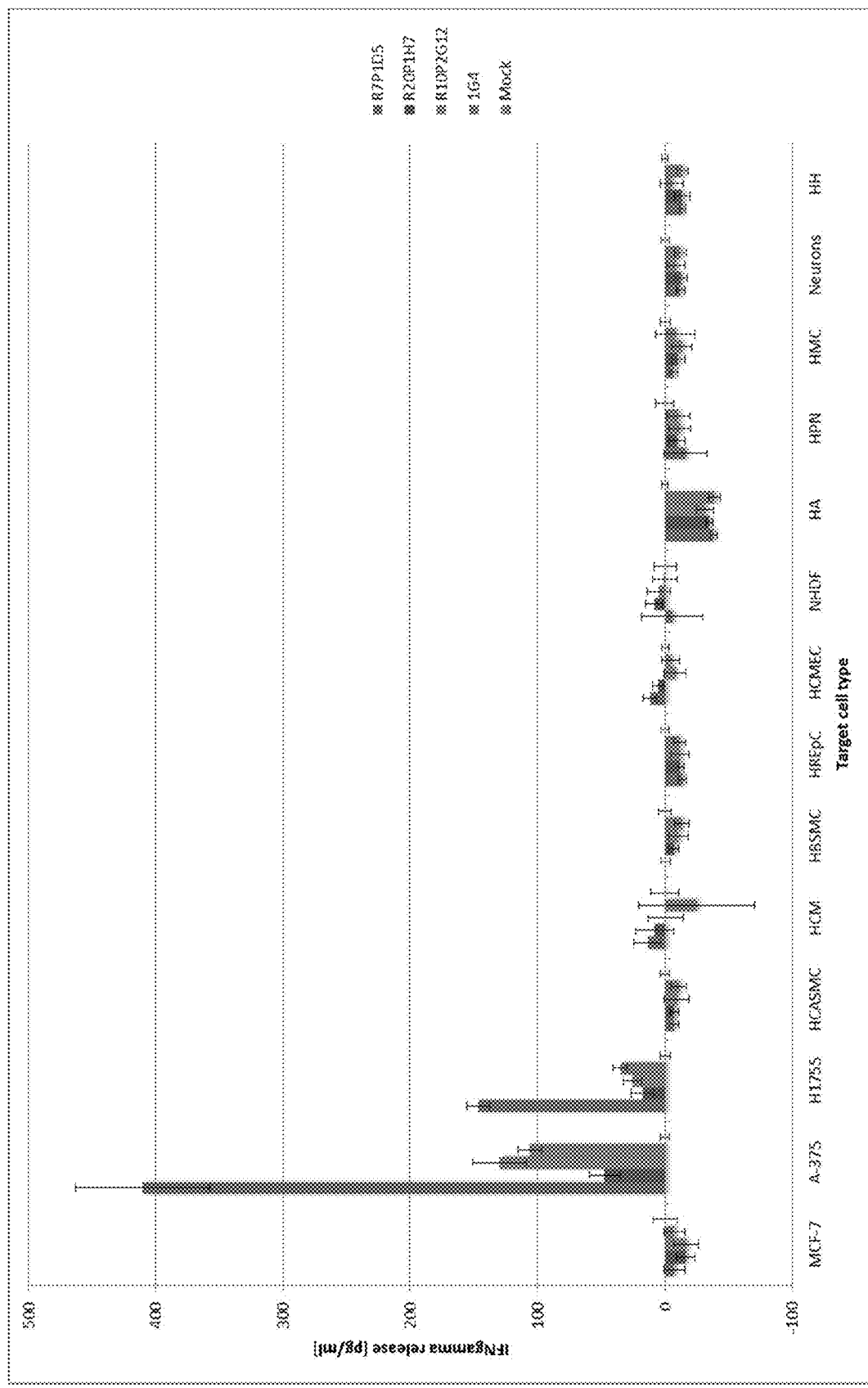
FIG. 13 T cells transfected with RNA coding for TCR R7P1D5, R10P2G12, R20P1H7, mock or the control TCR 1G4 (SEQ ID NO:X) were co-cultured with different primary human healthy tissue cells (see table 13 for abbreviations), the target negative tumor cell line MCF-7 and the MAGEA4—and NY-ESO1-positive cell lines A-375 and NCI-H1755. TCRs R7P1D5, R10P2G12, R20P1H7 and 1G4 expression in T cells was achieved by electroporation using an RNA vector. Human healthy tissue cell cultures did not lead to significant TCR-mediated recognition and T-cell activation for TCR R7P1D5, R10P2G12 or R20P1H7. E:T ratio 1:1, 20,000 cells each, mean of IFN-γ release after 20 h from replicates is shown as measured by ELISA. Error bars indicate standard deviations. Results were normalized by subtraction of IFN-γ release from TCR-transfected T cells only and IFN-γ release due to co-culture of Target cells and T cells not expressing TCR of interest.

The respective $CV_{norm}$ was calculated:

$$CV_{norm(TCRoi;co)} = [CV_{(TCRoi;co)}^2 + CV_{(TCRoi;effector\ only)}^2 + CV_{(mock;co)}^2 + $$
T-cells alone served as controls. IFN-γ secretion from CD8+ T-cells is indicative of T-cell activation with cytotoxic activity. $CV_{(mock;effector\ only)}^2]^{[1/2]}$ TCRoi=effector cells expressing TCR of interest
Mock=effector cells without exogenous TCR expression
Co=effector cells co-cultured with target cells
Effector only=effector cells not co-cultured
Mean$_{(norm)}$=mean IFNγ release (normalized)
CV$_{(norm)}$=coefficient of variation (normalized)
Results:

For CD8+ T cells expressing TCR R7P1D5, R10P2G12 or R20P1H7, no activation was observed upon co-culture with HLA-A*02 positive cell types from healthy tissues (see FIG. 13), while there was a activity towards the tumor cell lines A-375 and NCI-H1755 expressing HLA-A*02 and MAGEA4 as source gene for MAG-003 peptide. A similar pattern of reactivity was observed with CD8+ T cells expressing the NYESO1-specific TCR 1G4, which were found to be reactive towards NYESO1 expressing HLA-A*02 positive tumor cell lines but not towards the indicated panel of healthy tissue cells.

T-cell activation upon co-culture with cell lines expressing HLA-A*02 and MAGEA4 reflects the recognition of endogenously expressed and processed target pHLA by TCRs R7P1D5, R10P2G12 and R20P1H7.

The safety analysis indicates the absence of un-expected cross-reactivity or potential alloreactivity of TCR R7P1D5, R10P2G12 and R20P1H7 towards healthy tissue primary cells. This is noteworthy as the tested primary cell types represent thousands of normal HLA ligands in the context of HLA-A*02 and likely also represent additional allogeneic HLA alleles that vary from normal cell type to normal cell type.

Example 7: Lentiviral Expression of TCR of the Invention

T cell products were generated starting from bulk total Peripheral Blood Mononuclear Cells (PBMCs) isolated from healthy donors following a small scale ACTengine manufacturing process. The lentiviral vector backbone expressing R7P1D5 TCR of the invention for manufacturing ACTengine T cells was designed based on previous studies and multiple clinical trials (Porter et al., 2011; Kalos et al., 2011; and others) Briefly, thawed and rested PBMCs were activated with CD3/CD28 antibodies and transduced with concentrated viral supernatants manufactured using various lentiviral vectors carrying R7P1D5 TCR transgene with different orientations of α and β chains and various combinations of promotors and enhancer sequences (constructs were denoted as R71-R78). Two of the 8 constructs (R74, R75) were eliminated due to low titers and/or poor productivity. Cells transduced with the remaining 6 viral supernatants were expanded and evaluated for transgene expression by flow cytometry.

Orientations were as follows: Alpha-beta: R71, R72, 75, 76; beta-alpha: R73, R74, R77, 78, IG4.

Figure 14:
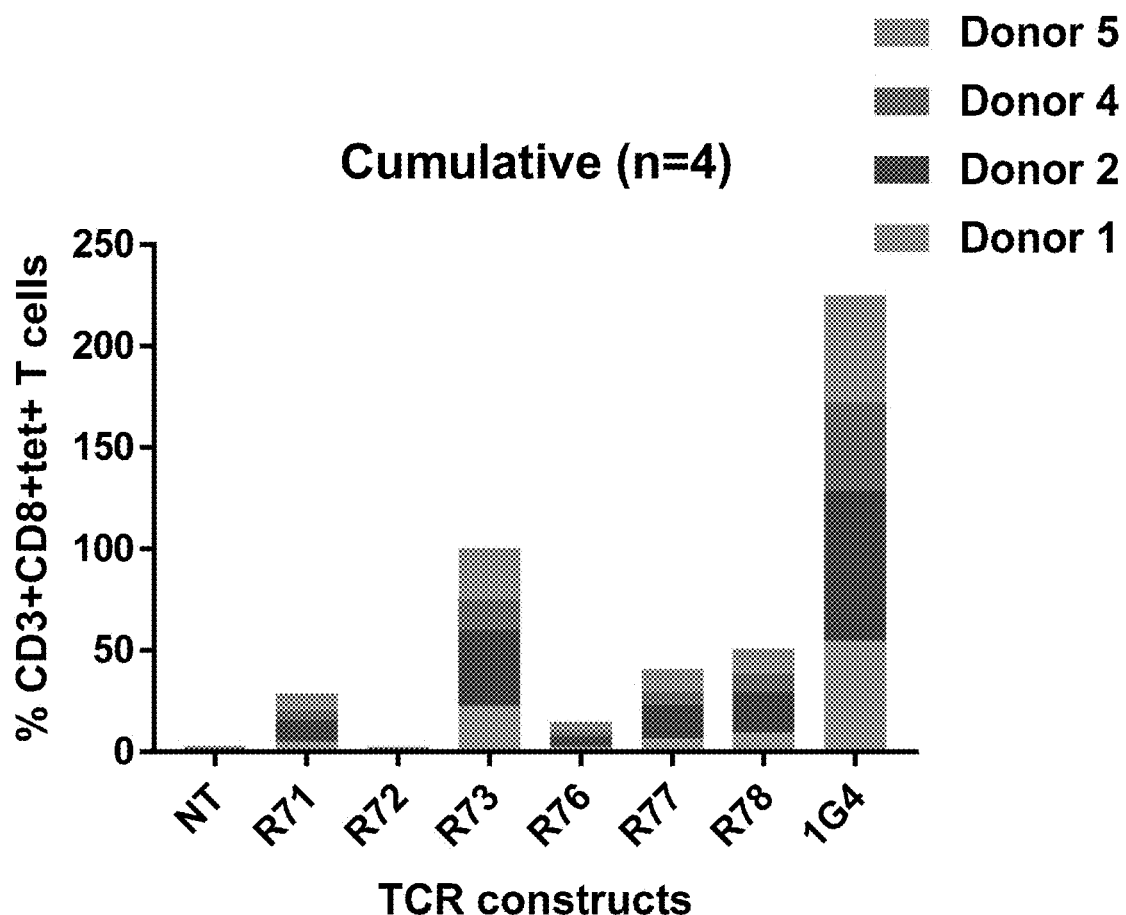
FIG. 14 shows cumulative data from 4 donors screened for R7P1D5 TCR transgene expression after transduction with 6 different lentiviral constructs (R71-R78). CD3+/CD8+ T-cells were analyzed by flow cytometry for proportion of MHC/MAG-003 tetramer binding cells at 96 hours post transduction. Non-transduced T-cells (NT) stained MHC/MAG-003 tetramer and 1G4 (NY-ESO1) TCR transduced T-cells stained with MHC/NYESO1-001 tetramer were used as negative and positive control, respectively. Cells were gated on Live CD3+/CD8+ population.

All T cell products showed comparable viability, percentage of lymphocytes as well as CD3+ T-cells. Percentage of CD4+ and CD8+ T-cells varied among the donors. No differences were observed in terms of toxicity among all 6 viral supernatants. R7P1D5 TCR lentiviral construct R73 consistently induced higher TCR expression as detected on the surface by tetramer binding. Based on transgene expression lentiviral constructs follow the order: R73>R78>R77>R71>R76>R72 (FIG. 14).

Figure 15A:
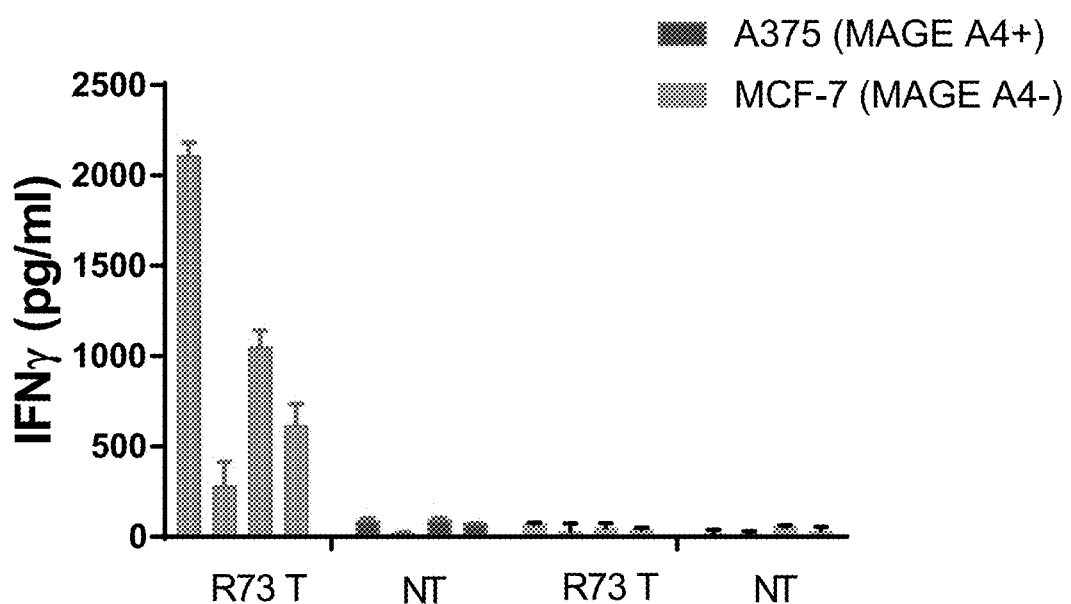
FIG. 15A shows effector response of R7P1D5 TCR transduced T-cells measured by means of IFNγ production upon co-culture MAGEA4 expressing tumor cell line A375 and MAGEA4 negative tumor cell line MCF-7. T-cells transduced with concentrated supernatant of R73 lentivirus encoding R7P1D5 TCR were compared with non-transduced cells (NT) both derived from PBMCs of 4 healthy donors. Results are presented as mean±SEM of triplicates.
Figure 15B:
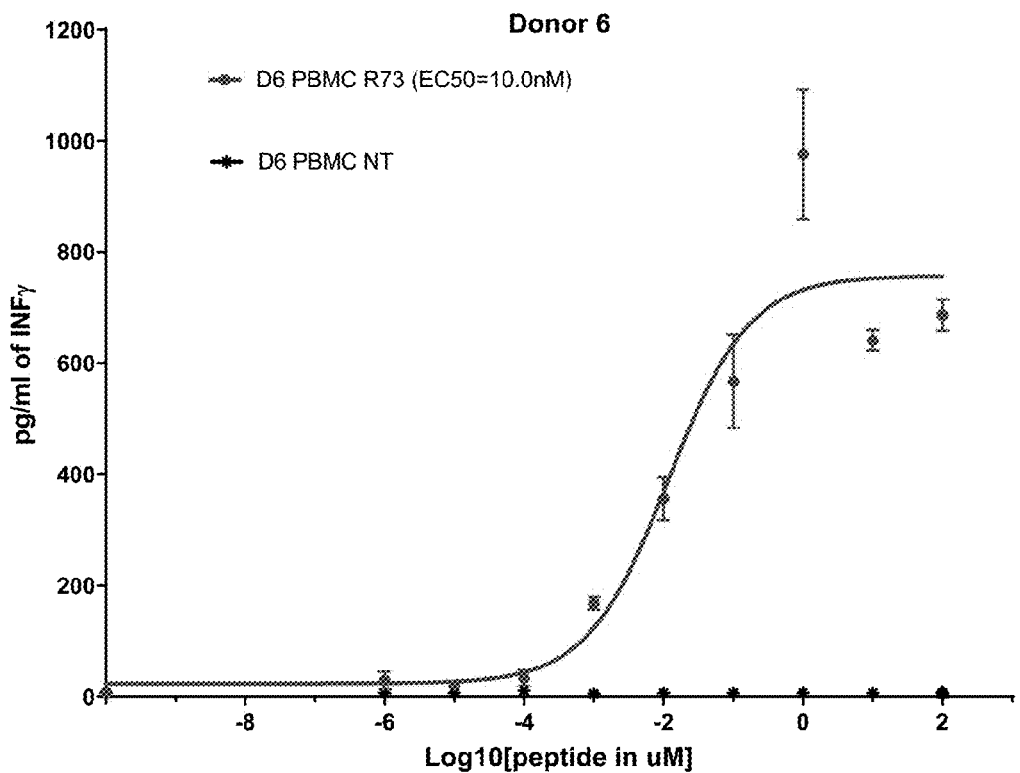
FIG. 15B shows IFNγ response of R7P1D5 TCR transduced (R73 lentivirus) T-cells from PBMC of 2 healthy donors (Donor 6 and 7) upon co-incubation with T2 target cells pulsed with decreasing concentrations of MAG-003 peptide. Results are presented as mean±SEM of triplicates measured 96 hours after transduction.
Figure 15B:
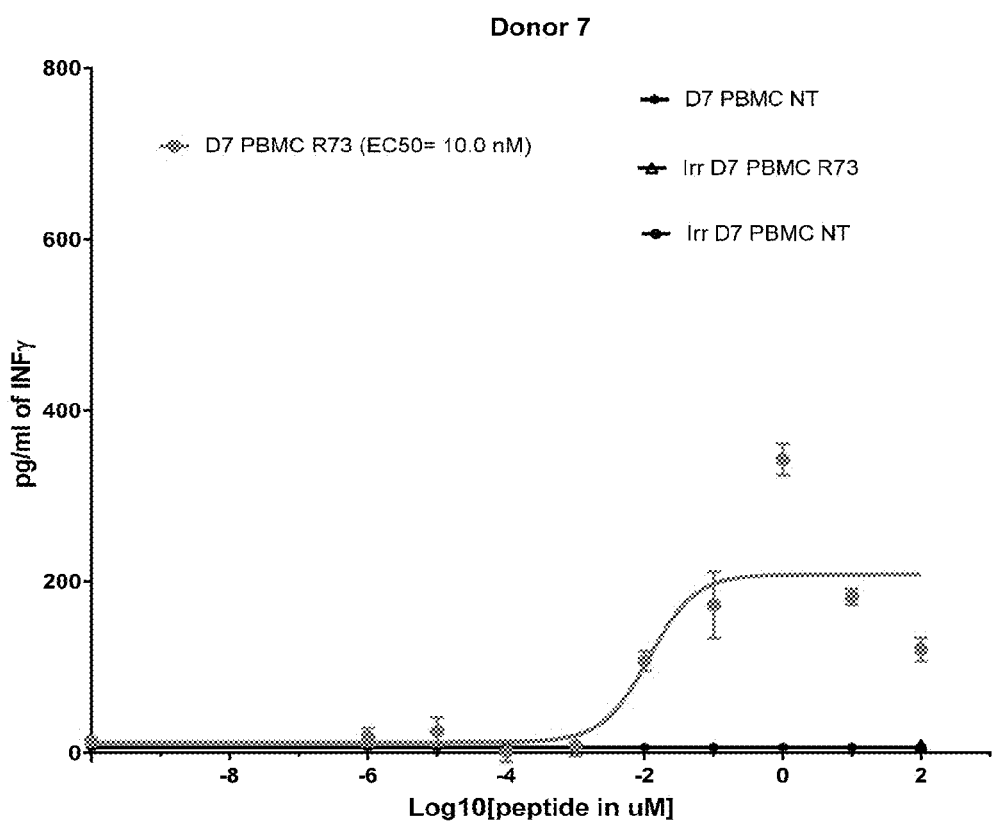

Additional experiments with 2 new donors were done to confirm the transducibility of the R7P1D5 TCR R73 virus. Transduced cell from all experiments were tested for functional evaluation in cytokine release and killing assays. In all donors tested, R73 transduced T cells derived from whole PBMCs of four donors exhibited significantly higher IFNγ production upon co-culturing with A375 cells expressing MAGE-A4 antigen as compared to non-transduced T cells (FIG. 15A). IFNγ response was strictly antigen specific as induction in presence of MCF-7 cells lacking MAGE-A4 expression was below background levels. In addition, $EC_{50}$ value derived from T2 titration curves representing IFNγ quantities detected in response to decreasing concentration of MAG-003 peptide was 10.0 nM in both donors (FIG. 15B).

Figure 16:
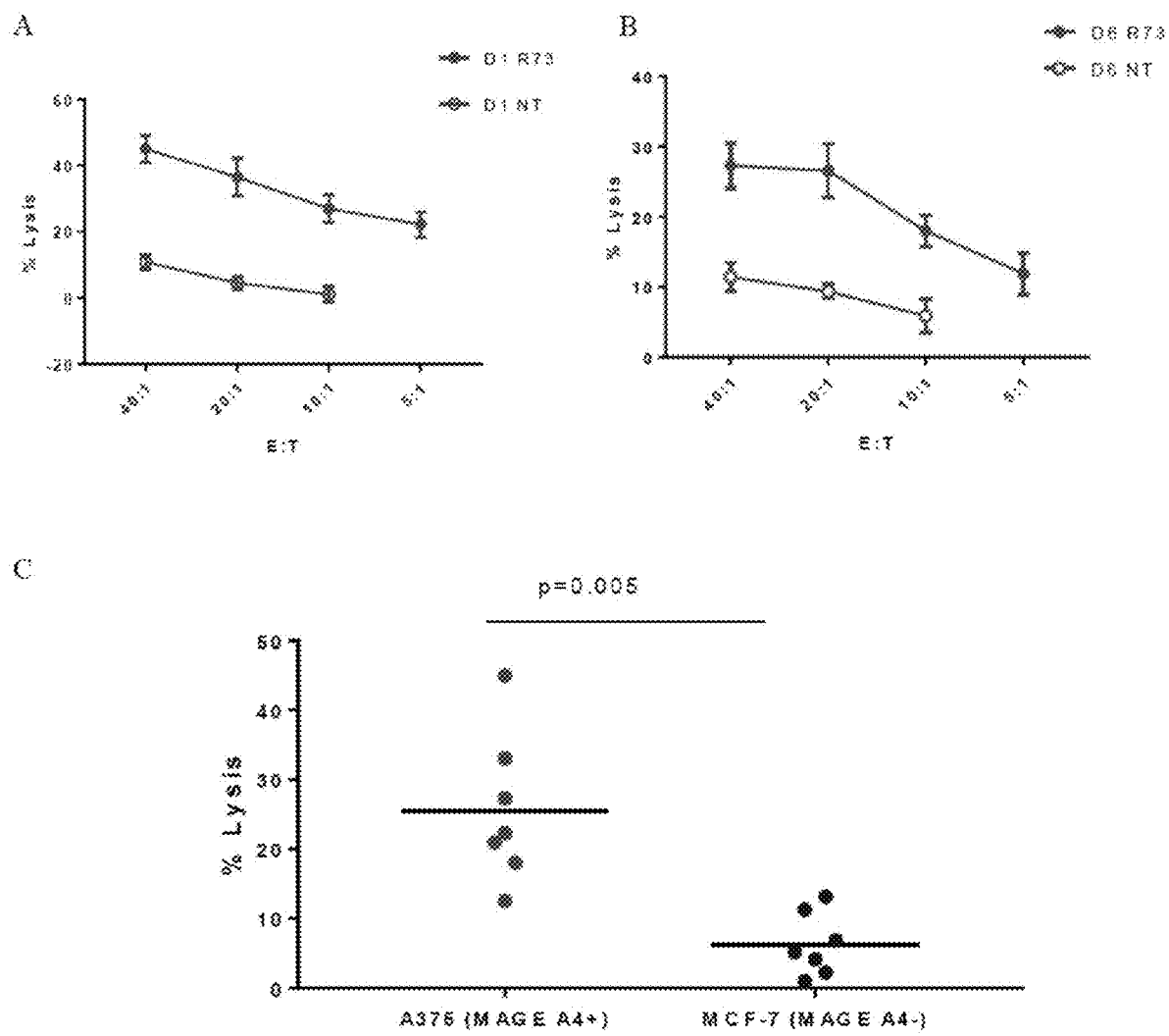
FIG. 16 shows cytotoxic response of R7P1D5 TCR (R73 lentivirus) transduced and non-transduced T-cells (NT) measured against MAGEA4 expressing tumor cell line A375 at different E:T ratios in a 4h Cr51 release assay. Results are presented as mean±SEM of 3-4 replicates. (C) Combined data from 7 R7P1D5 TCR (R73 lentivirus) transduced T-cell products generated from 5 donors showing antigen specific killing of MAGEA4 expressing (A375) and MAGEA4-negative (MCF-7) tumor targets at E:T ration of 40:1.

In addition to cytokine release, R7P1D5 TCR (R73 virus) transduced T cell products were tested in a 4 hour Cr51 release killing assay. Recognition and lysis of MAGE-A4+ A375 tumor cells presenting endogenously processed MAG003MAG-003 peptide were evaluated. LVR73 transduced T cells displayed increased killing over NT non-transduced cells at all E:T ratios (FIG. 16A, B). Cytotoxic effects seen with R73 transduced cells were mediated in antigen specific manner as percentage lysis observed with MAGE-A4+ targets was significantly higher than observed with MAGE-MAGEA-A4-negative target cells (FIG. 16C).

REFERENCE LIST

Adair S J, Hogan K T (2009). Treatment of ovarian cancer cell lines with 5-aza-2'-deoxycytidine upregulates the expression of cancer-testis antigens and class I major histocompatibility complex-encoded molecules. Cancer Immunol. Immunother. 58, 589-601.

Alves P M, Levy N, Bouzourene H, Viatte S, Bricard G, Ayyoub M, Vuilleumier H, Givel J C, Halkic N, Speiser D E, Romero P, Levy F (2007). Molecular and immunological evaluation of the expression of cancer/testis gene products in human colorectal cancer. Cancer Immunol. Immunother. 56, 839-847.

Andrade V C, Vettore A L, Felix R S, Almeida M S, Carvalho F, Oliveira J S, Chauffaille M L, Andriolo A, Caballero O L, Zago M A, Colleoni G W (2008). Prognostic impact of cancer/testis antigen expression in advanced stage multiple myeloma patients. Cancer Immun. 8, 2.

Aubry F, Satie A P, Rioux-Leclercq N, Rajpert-De M E, Spagnoli G C, Chomez P, De B O, Jegou B, Samson M (2001). MAGE-A4, a germ cell specific marker, is expressed differentially in testicular tumors. Cancer 92, 2778-2785.

Barrow C, Browning J, MacGregor D, Davis I D, Sturrock S, Jungbluth A A, Cebon J (2006). Tumor antigen expression in melanoma varies according to antigen and stage. Clin Cancer Res 12, 764-771.

Bellati F, Napoletano C, Tarquini E, Palaia I, Landi R, Manci N, Spagnoli G, Rughetti A, Panici P B, Nuti M (2007). Cancer testis antigen expression in primary and recurrent vulvar cancer: association with prognostic factors. Eur. J Cancer 43, 2621-2627.

Bergeron A, Picard V, LaRue H, Harel F, Hovington H, Lacombe L, Fradet Y (2009). High frequency of MAGE-A4 and MAGE-A9 expression in high-risk bladder cancer. Int. J Cancer 125, 1365-1371.

Bhan S, Chuang A, Negi S S, Glazer C A, Califano J A (2012). MAGEA4 induces growth in normal oral keratinocytes by inhibiting growth arrest and apoptosis. Oncol Rep. 28, 1498-1502.

Bode P K, Thielken A, Brandt S, Barghorn A, Lohe B, Knuth A, Moch H (2014). Cancer testis antigen expression in testicular germ cell tumorigenesis. Mod. Pathol. 27, 899-905.

Cabezon T, Gromova I, Gromov P, Serizawa R, Timmermans W, V, Kroman N, Celis J E, Moreira J M (2013). Proteomic profiling of triple-negative breast carcinomas in combination with a three-tier orthogonal technology approach identifies Mage-A4 as potential therapeutic target in estrogen receptor negative breast cancer. Mol. Cell Proteomics. 12, 381-394.

Cesson V, Rivals J P, Escher A, Piotet E, Thielemans K, Posevitz V, Dojcinovic D, Monnier P, Speiser D, Bron L, Romero P (2011). MAGE-A3 and MAGE-A4 specific CD4(+) T-cells in head and neck cancer patients: detection of naturally acquired responses and identification of new epitopes. Cancer Immunol. Immunother. 60, 23-35.

Chambost H, Van B N, Brasseur F, Godelaine D, Xerri L, Landi S J, Theate I, Plumas J, Spagnoli G C, Michel G, Coulie P G, Olive D (2000). Expression of gene MAGE-A4 in ReedSternberg cells. Blood 95, 3530-3533.

Chitale D A, Jungbluth A A, Marshall D S, Leitao M M, Hedvat C V, Kolb D, Spagnoli G C, Iversen K, Soslow R A (2005). Expression of cancer-testis antigens in endometrial carcinomas using a tissue microarray. Mod. Pathol. 18, 119-126.

Coral S, Parisi G, Nicolay H J, Colizzi F, Danielli R, Fratta E, Covre A, Taverna P, Sigalotti L, Maio M (2013). Immunomodulatory activity of SGI-110, a 5-aza-2'-deoxycytidine-containing demethylating dinucleotide. Cancer Immunol. Immunother. 62, 605-614.

Cruz C R, Gerdemann U, Leen A M, Shafer J A, Ku S, Tzou B, Horton T M, Sheehan A, Copeland A, Younes A, Rooney C M, Heslop H E, Bollard C M (2011). Improving T-cell therapy for relapsed EBV-negative Hodgkin lymphoma by targeting upregulated MAGE-A4. Clin Cancer Res 17, 7058-7066.

Cuffel C, Rivals J P, Zaugg Y, Salvi S, Seelentag W, Speiser D E, Lienard D, Monnier P, Romero P, Bron L, Rimoldi D (2011). Pattern and clinical significance of cancer-testis gene expression in head and neck squamous cell carcinoma. Int. J Cancer 128, 2625-2634.

Daudi S, Eng K H, Mhawech-Fauceglia P, Morrison C, Miliotto A, Beck A, Matsuzaki J, Tsuji T, Groman A, Gnjatic S, Spagnoli G, Lele S, Odunsi K (2014). Expression and immune responses to MAGE antigens predict survival in epithelial ovarian cancer. PLoS. ONE. 9, e104099.

Duffour M T, Chaux P, Lurquin C, Cornelis G, Boon T, van der Bruggen P (1999). A MAGE-A4 peptide presented by HLA-A2 is recognized by cytolytic T lymphocytes. Eur. J Immunol. 29, 3329-3337.

Forghanifard M M, Gholamin M, Farshchian M, Moaven O, Memar B, Forghani M N, Dadkhah E, Naseh H, Moghbeli M, Raeisossadati R, Abbaszadegan M R (2011). Cancer-testis gene expression profiling in esophageal squamous cell carcinoma: identification of specific tumor marker and potential targets for immunotherapy. Cancer Biol Ther. 12, 191-197.

Gerdemann U, Katari U, Christin A S, Cruz C R, Tripic T, Rousseau A, Gottschalk S M, Savoldo B, Vera J F, Heslop H E, Brenner M K, Bollard C M, Rooney C M, Leen A M (2011). Cytotoxic T lymphocytes simultaneously targeting multiple tumor-associated antigens to treat EBV negative lymphoma. Mol. Ther. 19, 2258-2268.

Gunda V, Cogdill A P, Bernasconi M J, Wargo J A, Parangi S (2013). Potential role of 5-aza2'-deoxycytidine induced MAGE-A4 expression in immunotherapy for anaplastic thyroid cancer. Surgery 154, 1456-1462.

Gure A O, Chua R, Williamson B, Gonen M, Ferrera C A, Gnjatic S, Ritter G, Simpson A J, Chen Y T, Old L J, Altorki N K (2005). Cancer-testis genes are coordinately expressed and are markers of poor outcome in non-small cell lung cancer. Clin Cancer Res 11, 8055-8062.

Hartmann S, Meyer T J, Brands R C, Haubitz I R, Linz C, Seher A, Kubler A C, Muller-Richter U D (2015). MAGE-A expression clusters and antineoplastic treatment in head and neck cancer. Int. J Mol. Med. 35, 1675-1682.

Hussein Y M, Morad F E, Gameel M A, Emam W A, El Sawy W H, El Tarhouny S A, Bayomy E S, Raafat N (2012). MAGE-4 gene m-RNA and TGF in blood as potential biochemical markers for HCC in HCV-infected patients. Med. Oncol 29, 3055-3062.

Jacobs J F, Grauer O M, Brasseur F, Hoogerbrugge P M, Wesseling P, Gidding C E, van de Rakt M W, Figdor C G, Coulie P G, de Vries I J, Adema G J (2008). Selective cancer-germline gene expression in pediatric brain tumors. J Neurooncol. 88, 273-280.

Jia Z C, Ni B, Huang Z M, Tian Y, Tang J, Wang J X, Fu X L, Wu Y Z (2010). Identification of two novel HLA-A*0201-restricted CTL epitopes derived from MAGE-A4. Clin Dev. Immunol. 2010, 567594.

Kageyama S, Ikeda H, Miyahara Y, Imai N, Ishihara M, Saito K, Sugino S, Ueda S, Ishikawa T, Kokura S, Naota H, Ohishi K, Shiraishi T, Inoue N, Tanabe M, Kidokoro T, Yoshioka H, Tomura D, Nukaya I, Mineno J, Takesako K, Katayama N, Shiku H (2015). Adoptive Transfer of MAGE-A4 T-cell Receptor Gene-Transduced Lymphocytes in Patients with Recurrent Esophageal Cancer. Clin. Cancer Res.

Kang J, Lee H J, Kim J, Lee J J, Maeng L S (2015). Dysregulation of X chromosome inactivation in high grade ovarian serous adenocarcinoma. PLoS. ONE. 10, e0118927.

Kawagoe H, Yamada A, Matsumoto H, Ito M, Ushijima K, Nishida T, Yakushiji M, Itoh K (2000). Serum MAGE-4 protein in ovarian cancer patients. Gynecol. Oncol 76, 336-339.

Kim K, Cho Y M, Park B H, Lee J L, Ro J Y, Go H, Shim J W (2015). Histological and immunohistochemical markers for progression prediction in transurethrally resected high-grade nonmuscle invasive bladder cancer. Int. J Clin Exp. Pathol. 8, 743-750.

Kobayashi T, Lonchay C, Colau D, Demotte N, Boon T, van der Bruggen P (2003). New MAGE-4 antigenic peptide recognized by cytolytic T lymphocytes on HLA-A1 tumor cells. Tissue Antigens 62, 426-432.

Kocher T, Zheng M, Bolli M, Simon R, Forster T, Schultz-Thater E, Remmel E, Noppen C, Schmid U, Ackermann D, Mihatsch M J, Gasser T, Heberer M, Sauter G, Spagnoli G C (2002). Prognostic relevance of MAGE-A4 tumor antigen expression in transitional cell carcinoma of the urinary bladder: a tissue microarray study. Int. J Cancer 100, 702-705.

Kubuschok B, Xie X, Jesnowski R, Preuss K D, Romeike B F, Neumann F, Regitz E, Pistorius G, Schilling M, Scheunemann P, Izbicki J R, Lohr J M, Pfreundschuh M (2004). Expression of cancer testis antigens in pancreatic carcinoma cell lines, pancreatic adenocarcinoma and chronic pancreatitis. Int. J Cancer 109, 568-575.

Li J, Yang Y, Fujie T, Tanaka F, Mimori K, Haraguchi M, Ueo H, Mori M, Akiyoshi T (1997). Expression of the MAGE gene family in human gastric carcinoma. Anticancer Res 17, 3559-3563.

Li M, Yuan Y H, Han Y, Liu Y X, Yan L, Wang Y, Gu J (2005). Expression profile of cancer-testis genes in 121 human colorectal cancer tissue and adjacent normal tissue. Clin Cancer Res 11, 1809-1814.

Lifantseva N, Koltsova A, Krylova T, Yakovleva T, Poljanskaya G, Gordeeva 0 (2011). Expression patterns of cancer-testis antigens in human embryonic stem cells and their cell derivatives indicate lineage tracks. Stem Cells Int. 2011, 795239.

Luftl M, Schuler G, Jungbluth A A (2004). Melanoma or not? Cancer testis antigens may help. Br. J Dermatol. 151, 1213-1218.

Melo D H, Mamede R C, Neder L, Saggioro F P, Figueiredo D L, da Silva WAJ, Jungbluth A A, Zago M A (2011). Expression of MAGE-A4 and MAGE-C1 tumor-associated antigen in benign and malignant thyroid diseases. Head Neck 33, 1426-1432.

Mischo A, Kubuschok B, Ertan K, Preuss K D, Romeike B, Regitz E, Schormann C, de B D, Wadle A, Neumann F, Schmidt W, Renner C, Pfreundschuh M (2006). Prospective study on the expression of cancer testis genes and antibody responses in 100 consecutive patients with primary breast cancer. Int. J Cancer 118, 696-703.

Mitchell R T, Camacho-Moll E, MacDonald J, Anderson R A, Kelnar C J, O'Donnell M, Sharpe R M, Smith L B, Grigor K M, Wallace W H, Stoop H, Wolffenbuttel K P, Donat R, Saunders P T, Looijenga L H (2014). Intratubular germ cell neoplasia of the human testis: heterogeneous protein expression and relation to invasive potential. Mod. Pathol. 27, 1255-1266.

Miyahara Y, Naota H, Wang L, Hiasa A, Goto M, Watanabe M, Kitano S, Okumura S, Takem itsu T, Yuta A, Majima Y, Lemonnier F A, Boon T, Shiku H (2005). Determination of cellularly processed HLA-A2402-restricted novel CTL epitopes derived from two cancer germ line genes, MAGE-A4 and SAGE. Clin Cancer Res 11, 5581-5589.

Montoro J R, Mamede R C, Neder S L, Saggioro F P, Figueiredo D L, Silva W A, Jr., Jungbluth A A, Spagnoli G C, Zago M A (2012). Expression of cancer-testis antigens MAGE-A4 and MAGE-C1 in oral squamous cell carcinoma. Head Neck 34, 1123-1128.

Nagao T, Higashitsuji H, Nonoguchi K, Sakurai T, Dawson S, Mayer R J, Itoh K, Fujita J (2003). MAGE-A4 interacts with the liver oncoprotein gankyrin and suppresses its tumorigenic activity. J Biol Chem 278, 10668-10674.

Naota H, Miyahara Y, Okumura S, Kuzushima K, Akatsuka Y, Hiasa A, Kitano S, Takahashi T, Yuta A, Majima Y, Shiku H (2006). Generation of peptide-specific CD8+ T-cells by phytohemagglutinin-stimulated antigen-mRNA-transduced CD4+ T-cells. J Immunol. Methods 314, 54-66.

Nishikawa H, Maeda Y, Ishida T, Gnjatic S, Sato E, Mori F, Sugiyama D, Ito A, Fukumori Y, Utsunomiya A, Inagaki H, Old L J, Ueda R, Sakaguchi S (2012). Cancer/testis antigens are novel targets of immunotherapy for adult T-cell leukemia/lymphoma. Blood 119, 3097-3104.

Oba-Shinjo S M, Caballero O L, Jungbluth A A, Rosenberg S, Old L J, Simpson A J, Marie S K (2008). Cancer-testis (C T) antigen expression in medulloblastoma. Cancer Immun. 8, 7.

Ohkuri T, Wakita D, Chamoto K, Togashi Y, Kitamura H, Nishimura T (2009). Identification of novel helper epitopes of MAGE-A4 tumour antigen: useful tool for the propagation of Th1 cells. Br. J Cancer 100, 1135-1143.

Ottaviani S, Colau D, van der Bruggen P, van der Bruggen P (2006). A new MAGE-4 antigenic peptide recognized by cytolytic T lymphocytes on HLA-A24 carcinoma cells. Cancer Immunol. Immunother. 55, 867-872.

Otte M, Zafrakas M, Riethdorf L, Pichlmeier U, Loning T, Janicke F, Pantel K (2001). MAGE-A gene expression pattern in primary breast cancer. Cancer Res 61, 6682-6687.

Peikert T, Specks U, Farver C, Erzurum S C, Comhair S A (2006). Melanoma antigen A4 is expressed in non-small cell lung cancers and promotes apoptosis. Cancer Res 66, 4693-4700.

Peng J R, Chen H S, Mou D C, Cao J, Cong X, Qin L L, Wei L, Leng X S, Wang Y, Chen W F (2005). Expression of cancer/testis (C T) antigens in Chinese hepatocellular carcinoma and its correlation with clinical parameters. Cancer Lett. 219, 223-232.

Perez D, Herrmann T, Jungbluth A A, Samartzis P, Spagnoli G, Demartines N, Clavien P A, Marino S, Seifert B, Jaeger D (2008). Cancer testis antigen expression in gastrointestinal stromal tumors: new markers for early recurrence. Int. J Cancer 123, 1551-1555.

Prasad M L, Jungbluth A A, Patel S G, Iversen K, Hoshaw-Woodard S, Busam K J (2004). Expression and significance of cancer testis antigens in primary mucosal melanoma of the head and neck. Head Neck 26, 1053-1057.

Quillien V, Raoul J L, Heresbach D, Collet B, Toujas L, Brasseur F (1997). Expression of MAGE genes in esophageal squamous-cell carcinoma. Anticancer Res. 17, 387-391.

Rammensee H G, Bachmann J, Emmerich N P, Bachor O A, Stevanovic S (1999). SYFPEITHI: database for MHC ligands and peptide motifs. Immunogenetics 50, 213-219.

Rammensee H G, Bachmann J, Stevanovic S (1997). MHC Ligands and Peptide Motifs. (Heidelberg, Germany: Springer-Verlag).

Resnick M B, Sabo E, Kondratev S, Kerner H, Spagnoli G C, Yakirevich E (2002). Cancer-testis antigen expression in uterine malignancies with an emphasis on carcinosarcomas and papillary serous carcinomas. Int. J Cancer 101, 190-195.

Ries J, Schultze-Mosgau S, Neukam F, Diebel E, Wiltfang J (2005). Investigation of the expression of melanoma antigen-encoding genes (MAGE-A1 to -A6) in oral squamous cell carcinomas to determine potential targets for gene-based cancer immunotherapy. Int. J Oncol. 26, 817-824.

Saito T, Wada H, Yamasaki M, Miyata H, Nishikawa H, Sato E, Kageyama S, Shiku H, Mori M, Doki Y (2014). High expression of MAGE-A4 and MHC class I antigens in tumor cells and induction of MAGE-A4 immune responses are prognostic markers of CHP-MAGE-A4 cancer vaccine. Vaccine 32, 5901-5907.

Sakurai T, Itoh K, Higashitsuji H, Nagao T, Nonoguchi K, Chiba T, Fujita J (2004). A cleaved form of MAGE-A4 binds to Miz-1 and induces apoptosis in human cells. J Biol Chem 279, 15505-15514.

Sarcevic B, Spagnoli G C, Terracciano L, Schultz-Thater E, Heberer M, Gamulin M, Krajina Z, Oresic T, Separovic R, Juretic A (2003). Expression of cancer/testis tumor associated antigens in cervical squamous cell carcinoma. Oncology 64, 443-449.

Schirmer U, Fiegl H, Pfeifer M, Zeimet A G, Muller-Holzner E, Bode P K, Tischler V, Altevogt P (2013). Epigenetic regulation of L1CAM in endometrial carcinoma: comparison to cancer-testis (CT-X) antigens. BMC. Cancer 13, 156.

Shafer J A, Cruz C R, Leen A M, Ku S, Lu A, Rousseau A, Heslop H E, Rooney C M, Bollard C M, Foster A E (2010). Antigen-specific cytotoxic T lymphocytes can target chemoresistant side-population tumor cells in Hodgkin lymphoma. Leuk. Lymphoma 51, 870-880.

Sharma P, Shen Y, Wen S, Bajorin D F, Reuter V E, Old L J, Jungbluth A A (2006). Cancer-testis antigens: expression and correlation with survival in human urothelial carcinoma. Clin Cancer Res 12, 5442-5447.

Shichijo S, Hoshino T, Koufuji K, Hayashi A, Kawamoto M, Kikuchi M, Higuchi T, Ichiki M, Oizumi K, Itoh K (1997). Detection of MAGE-4 protein in sera of lung cancer patients. Jpn. J Cancer Res 88, 414-419.

Shigematsu Y, Hanagiri T, Shiota H, Kuroda K, Baba T, Mizukami M, So T, Ichiki Y, Yasuda M, So T, Takenoyama M, Yasumoto K (2010). Clinical significance of cancer/testis antigens expression in patients with non-small cell lung cancer. Lung Cancer 68, 105-110.

Shirakura Y, Mizuno Y, Wang L, Imai N, Amaike C, Sato E, Ito M, Nukaya I, Mineno J, Takesako K, Ikeda H, Shiku H (2012). T-cell receptor gene therapy targeting melanoma-associated antigen-A4 inhibits human tumor growth in non-obese diabetic/SCID/gammacnull mice. Cancer Sci. 103, 17-25.

Soga N, Hori Y, Yamakado K, Ikeda H, Imai N, Kageyama S, Nakase K, Yuta A, Hayashi N, Shiku H, Sugimura Y (2013). Limited expression of cancer-testis antigens in renal cell carcinoma patients. Mol. Clin Oncol 1, 326-330.

Su C, Xu Y, Li X, Ren S, Zhao C, Hou L, Ye Z, Zhou C (2015). Predictive and prognostic effect of CD133 and cancer-testis antigens in stage Ib-IIIA non-small cell lung cancer. Int. J Clin Exp. Pathol. 8, 5509-5518.

Takahashi N, Ohkuri T, Homma S, Ohtake J, Wakita D, Togashi Y, Kitamura H, Todo S, Nishimura T (2012). First clinical trial of cancer vaccine therapy with artificially synthesized helper/killer-hybrid epitope long peptide of MAGE-A4 cancer antigen. Cancer Sci. 103, 150-153.

Tanaka F, Mori M, Li J, Fujie T, Mimori K, Haraguchi M, Tanaka Y, Mafune K, Akiyoshi T (1997). High frequency of the expression of the MAGE gene family in human esophageal carcinoma. Int. J Oncol 10, 1113-1117.

Tsuzurahara S, Sata M, Iwamoto O, Shichijo S, Kojiro M, Tanikawa K, Itoh K (1997). Detection of MAGE-4 protein in the sera of patients with hepatitis-C virus-associated hepatocellular carcinoma and liver cirrhosis. Jpn. J Cancer Res 88, 915-918.

Walter S, Herrgen L, Schoor O, Jung G, Wernet D, BUhring H J, Rammensee H G, Stevanovio S. (2003). Cutting edge: predetermined avidity of human CD8 T cells expanded on calibrated MHC/anti-CD28-coated microspheres. J Immunol. 171(10), 4974-8

Wang M, Li J, Wang L, Chen X, Zhang Z, Yue D, Ping Y, Shi X, Huang L, Zhang T, Yang L, Zhao Y, Ma X, Li D, Fan Z, Zhao L, Tang Z, Zhai W, Zhang B, Zhang Y (2015). Combined cancer testis antigens enhanced prediction accuracy for prognosis of patients with hepatocellular carcinoma. Int. J Clin Exp. Pathol. 8, 3513-3528.

Wu Z Y, Gao Y F, Wu Y H, Liu W, Sun M, Zhai M X, Qi Y M, Ye Y (2011). Identification of a novel CD8+ T-cell epitope derived from cancer-testis antigen MAGE-4 in oesophageal carcinoma. Scand. J Immunol. 74, 561-567.

Yakirevich E, Sabo E, Lavie O, Mazareb S, Spagnoli G C, Resnick M B (2003). Expression of the MAGE-A4 and N Y-ESO-1 cancer-testis antigens in serous ovarian neoplasms. Clin Cancer Res 9, 6453-6460.

Yamada R, Takahashi A, Torigoe T, Morita R, Tamura Y, Tsukahara T, Kanaseki T, Kubo T, Watarai K, Kondo T, Hirohashi Y, Sato N (2013). Preferential expression of cancer/testis genes in cancer stem-like cells: proposal of a novel sub-category, cancer/testis/stem gene. Tissue Antigens 81, 428-434.

Yoshida N, Abe H, Ohkuri T, Wakita D, Sato M, Noguchi D, Miyamoto M, Morikawa T, Kondo S, Ikeda H, Nishimura T (2006). Expression of the MAGE-A4 and N Y-ESO-1 cancer-testis antigens and T-cell infiltration in non-small cell lung carcinoma and their prognostic significance. Int. J Oncol 28, 1089-1098.

Zhang Y, Stroobant V, Russo V, Boon T, van der Bruggen P (2002). A MAGE-A4 peptide presented by HLA-B37 is recognized on human tumors by cytolytic T lymphocytes. Tissue Antigens 60, 365-371.

Zimmermann A K, Imig J, Klar A, Renner C, Korol D, Fink D, Stadlmann S, Singer G, Knuth A, Moch H, Caduff R (2013). Expression of MAGE-C1/CT7 and selected cancer/testis antigens in ovarian borderline tumours and primary and recurrent ovarian carcinomas. Virchows Arch. 462, 565-574.

The invention claimed is:

1. A method of treating a patient who has cancer that presents a peptide consisting of the amino acid sequence of KVLEHVVRV (SEQ ID NO: 1) in a complex with HLA-A*02, comprising administering to the patient a population of transformed CD8+ T cells expressing at least one vector encoding a T cell receptor (TCR),
    wherein the TCR comprises SEQ ID NO: 42, SEQ ID NO: 43, SEQ ID NO: 44, SEQ ID NO: 50, SEQ ID NO: 51, and SEQ ID NO: 52,
    wherein the TCR is capable of binding to a peptide consisting of the amino acid sequence of KVLEHVVRV (SEQ ID NO: 1) in a complex with HLA-A*02, and
    wherein the cancer is selected from non-small cell lung cancer (NSCLC), melanoma, and ovarian cancer (OC).

2. The method of claim 1, wherein the population of transformed cells are produced by a method comprising
    isolating a cell from a subject,
    transforming the cell with at least one vector encoding the TCR to produce a transformed cell, and
    expanding the transformed cell to produce the population of transformed cells.

3. The method of claim 2, wherein the subject is the patient.

4. The method of claim 2, wherein the subject is a healthy donor.

5. The method of claim 1, wherein the TCR comprises
    an α chain comprising the amino acid sequence of SEQ ID NO: 39 and a β chain comprising the amino acid sequence of SEQ ID NO: 47.

6. The method of claim 1, wherein the population of transformed cells are administered in the form of a pharmaceutical composition.

7. The method of claim 6, wherein the pharmaceutical composition comprises a chemotherapeutic agent selected from the group consisting of asparaginase, busulfan, carboplatin, cisplatin, daunorubicin, doxorubicin, fluorouracil, gemcitabine, hydroxyurea, methotrexate, paclitaxel, rituximab, vinblastine, and vincristine.

8. The method of claim 1, wherein the TCR comprises:
    a CDR1α chain comprising the amino acid sequence of SEQ ID NO: 42,
    a CDR2α chain comprising the amino acid sequence of SEQ ID NO: 43,
    a CDR3α chain comprising the amino acid sequence of SEQ ID NO: 44,
    a CDR1β chain comprising the amino acid sequences of SEQ ID NO: 50,
    a CDR2β chain comprising the amino acid sequence of SEQ ID NO: 51, and
    a CDR3β chain comprising the amino acid sequence of SEQ ID NO: 52.

9. The method of claim 1, wherein the TCR comprises
    a CDR1α chain consisting of the amino acid sequence of SEQ ID NO: 42,
    a CDR2α chain comprising the amino acid sequence of SEQ ID NO: 43,
    a CDR3α chain consisting of the amino acid sequence of SEQ ID NO: 44,
    a CDR1β chain consisting of the amino acid sequence of SEQ ID NO: 50,
    a CDR2β chain comprising the amino acid sequence of SEQ ID NO: 51, and
    a CDR3β chain consisting of the amino acid sequence of SEQ ID NO: 52.

10. The method of claim 1, wherein the TCR comprises
    a CDR1α chain consisting of the amino acid sequence of SEQ ID NO: 42,
    a CDR2α chain consisting of the amino acid sequence of SEQ ID NO: 43,
    a CDR3α chain comprising the amino acid sequence of SEQ ID NO: 44,
    a CDR1β chain consisting of the amino acid sequence of SEQ ID NO: 50,
    a CDR2β chain consisting of the amino acid sequence of SEQ ID NO: 51, and
    a CDR3β chain comprising the amino acid sequence of SEQ ID NO: 52.

11. The method of claim 1, wherein the TCR comprises
    a CDR1α chain consisting of the amino acid sequence of SEQ ID NO: 42,
    a CDR2α chain consisting of the amino acid sequence of SEQ ID NO: 43,
    a CDR3α chain consisting of the amino acid sequence of SEQ ID NO: 44,
    a CDR1β chain consisting of the amino acid sequence of SEQ ID NO: 50,
    a CDR2β chain consisting of the amino acid sequence of SEQ ID NO: 51, and
    a CDR3β chain consisting of the amino acid sequence of SEQ ID NO: 52.

12. The method of claim 1, wherein the cancer is ovarian cancer.

13. The method of claim 1, wherein the cancer is non-small cell lung cancer.

14. The method of claim 1, wherein the binding affinity ($K_D$) for the TCR binding to a peptide consisting of the amino acid sequence of KVLEHVVRV (SEQ ID NO: 1) in a complex with an MHC class I molecule is about 100 μM or less.

15. The method of claim 11, wherein the binding affinity ($K_D$) for the TCR binding to a peptide consisting of the amino acid sequence of KVLEHVVRV (SEQ ID NO: 1) in a complex with an MHC class I molecule is about 100 μM or less.

16. The method of claim 1, wherein the TCR comprises
a CDR1α chain comprising the amino acid sequence of SEQ ID NO: 42,
a CDR2α chain consisting of the amino acid sequence of SEQ ID NO: 43,
a CDR3α chain consisting of the amino acid sequence of SEQ ID NO: 44,
a CDR1β chain comprising the amino acid sequence of SEQ ID NO: 50,
a CDR2β chain consisting of the amino acid sequence of SEQ ID NO: 51, and
a CDR3β chain consisting of the amino acid sequence of SEQ ID NO: 52.

17. The method of claim 1, wherein the TCR comprises
a CDR1α chain comprising the amino acid sequence of SEQ ID NO: 42,
a CDR2α chain comprising the amino acid sequence of SEQ ID NO: 43,
a CDR3α chain consisting of the amino acid sequence of SEQ ID NO: 44,
a CDR1β chain comprising the amino acid sequence of SEQ ID NO: 50,
a CDR2β chain comprising the amino acid sequence of SEQ ID NO: 51, and
a CDR3β chain consisting of the amino acid sequence of SEQ ID NO: 52.

18. The method of claim 1, wherein the TCR comprises
a CDR1α chain comprising the amino acid sequence of SEQ ID NO: 42,
a CDR2α chain consisting of the amino acid sequence of SEQ ID NO: 43,
a CDR3α chain comprising the amino acid sequence of SEQ ID NO: 44,
a CDR1β chain comprising the amino acid sequence of SEQ ID NO: 50,
a CDR2β chain consisting of the amino acid sequence of SEQ ID NO: 51, and
a CDR3β chain comprising the amino acid sequence of SEQ ID NO: 52.

19. The method of claim 1, wherein the TCR comprises
a CDR1α chain consisting of the amino acid sequence of SEQ ID NO: 42,
a CDR2α chain comprising the amino acid sequence of SEQ ID NO: 43,
a CDR3α chain comprising the amino acid sequence of SEQ ID NO: 44,
a CDR1β chain consisting of the amino acid sequence of SEQ ID NO: 50,
a CDR2β chain comprising the amino acid sequence of SEQ ID NO: 51, and
a CDR3β chain comprising the amino acid sequence of SEQ ID NO: 52.

20. The method of claim 1, wherein the cancer is melanoma.

* * * * *